(12) United States Patent
Jayol

(10) Patent No.: US 11,623,074 B2
(45) Date of Patent: *Apr. 11, 2023

(54) GIRTH ADJUSTABLE DEVICE

(71) Applicant: Benjamin Ernest Heloïs Jayol, Los Angeles, CA (US)

(72) Inventor: Benjamin Ernest Heloïs Jayol, Los Angeles, CA (US)

( * ) Notice: Subject to any disclaimer, the term of this patent is extended or adjusted under 35 U.S.C. 154(b) by 301 days.

This patent is subject to a terminal disclaimer.

(21) Appl. No.: 16/976,466

(22) PCT Filed: Feb. 28, 2019

(86) PCT No.: PCT/US2019/019920
§ 371 (c)(1),
(2) Date: Aug. 27, 2020

(87) PCT Pub. No.: WO2019/169056
PCT Pub. Date: Sep. 6, 2019

(65) Prior Publication Data
US 2021/0008357 A1 Jan. 14, 2021

Related U.S. Application Data

(60) Provisional application No. 62/636,240, filed on Feb. 28, 2018.

(51) Int. Cl.
*A61M 29/00* (2006.01)
*A61H 19/00* (2006.01)

(52) U.S. Cl.
CPC ............ *A61M 29/00* (2013.01); *A61H 19/32* (2013.01); *A61H 19/44* (2013.01); *A61M 2205/582* (2013.01); *A61M 2205/583* (2013.01); *A61M 2205/586* (2013.01); *A61M 2205/80* (2013.01); *A61M 2210/1475* (2013.01); *A61M 2210/167* (2013.01); *A61M 2230/06* (2013.01)

(58) Field of Classification Search
CPC ............ A61M 29/00; A61M 2205/582; A61M 2205/583; A61M 2205/586; A61M 2205/80; A61M 2210/1475; A61M 2210/167; A61H 19/32; A61H 19/44; A61B 1/32
See application file for complete search history.

(56) References Cited

U.S. PATENT DOCUMENTS

| | | | | |
|---|---|---|---|---|
| 5,785,648 A * | 7/1998 | Min | ........................ | A61B 1/32 600/206 |
| 5,795,289 A * | 8/1998 | Wyttenbach | ............. | A61B 1/32 606/198 |
| 9,533,080 B1 * | 1/2017 | Carrier | .................... | A61M 1/86 |
| 11,247,031 B2 * | 2/2022 | Jayol | ........................ | A61B 1/32 |
| 2018/0193619 A1 * | 7/2018 | Juravic | .................. | A61B 17/42 |

* cited by examiner

*Primary Examiner* — Steven O Douglas

(57) ABSTRACT

A girth adjustable device for dilation and stretch of body orifices for medical applications, massage, body orifice improvement and activities pleasurable to the body, that can repeatedly, gradually increase and decrease a uniform and sustainable pressure against the entire lateral surface area of body orifices. The girth adjustable device comprises at least one controller, a housing, at least one threaded shaft, at least one module, a plurality of shaft members and at least one sheath. The part of the girth adjustable device that has to be inserted into body orifices is the shaft. In a body orifice, the user increases and decreases the girth size of the shaft via the controller.

127 Claims, 56 Drawing Sheets

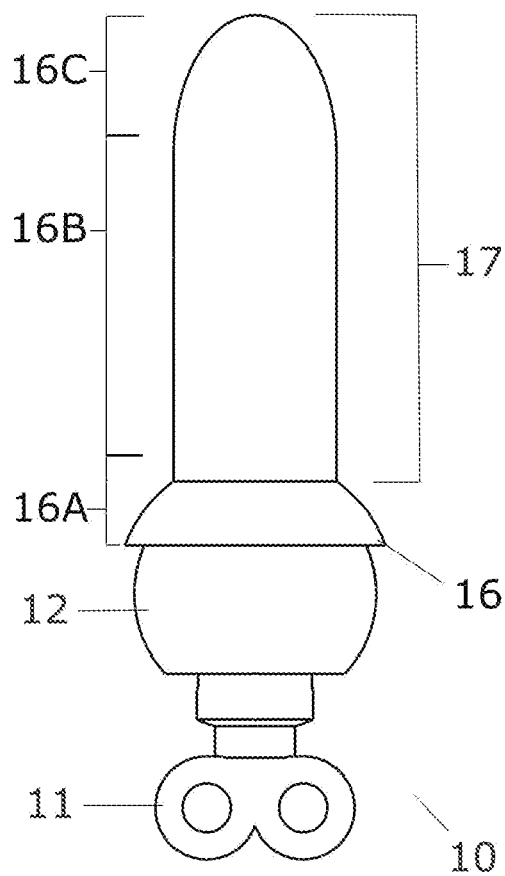
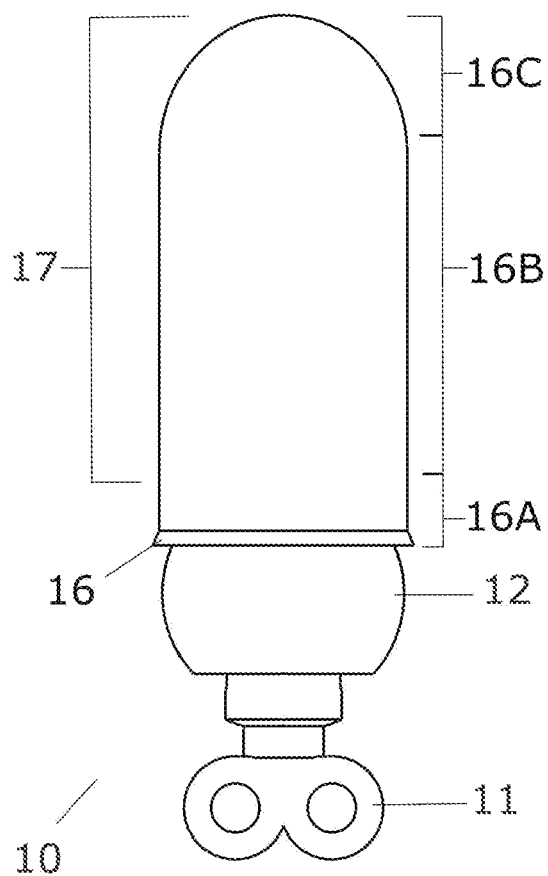
FIG. 1A
FIG. 1B
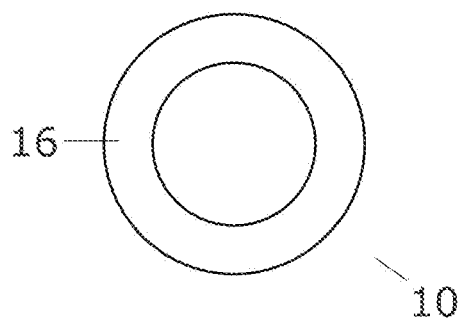
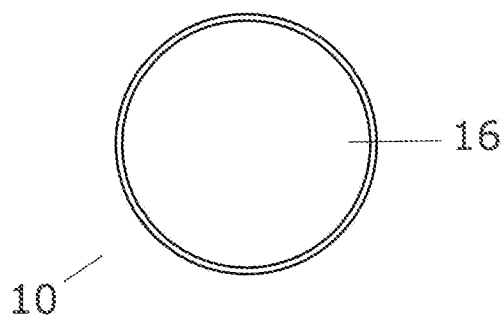
FIG. 1C
FIG. 1D

FIG. 18
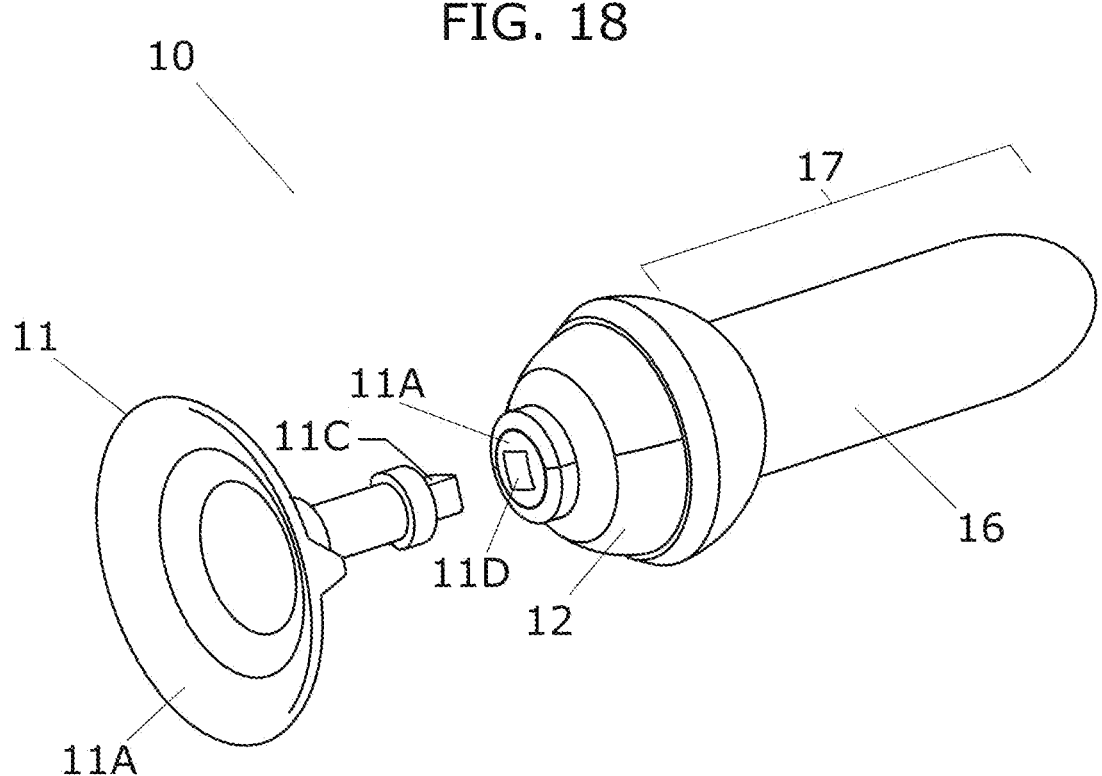
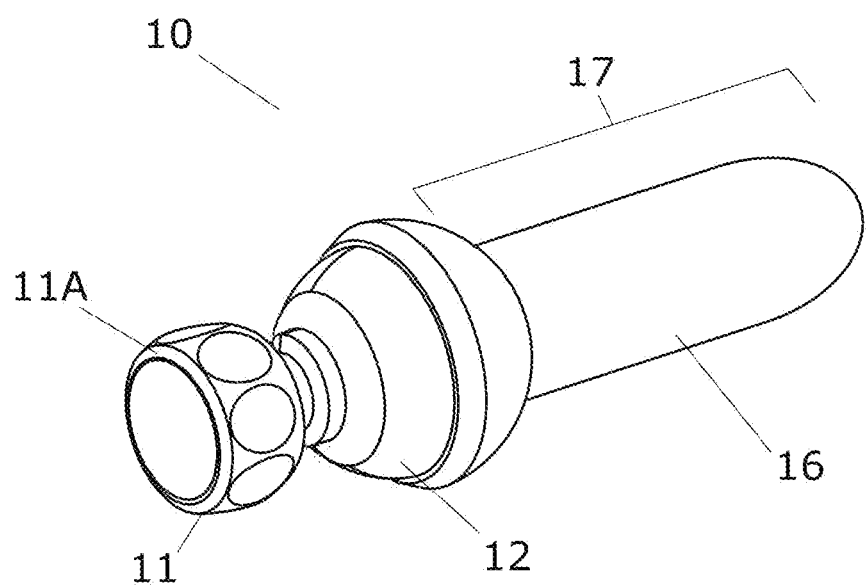
FIG. 19A

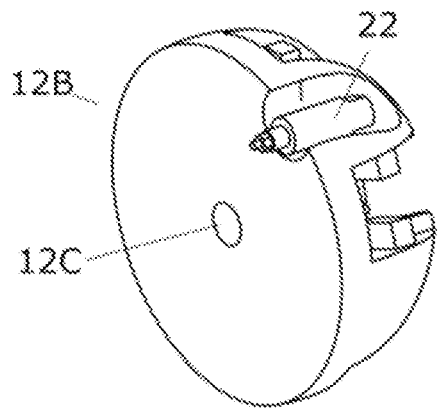
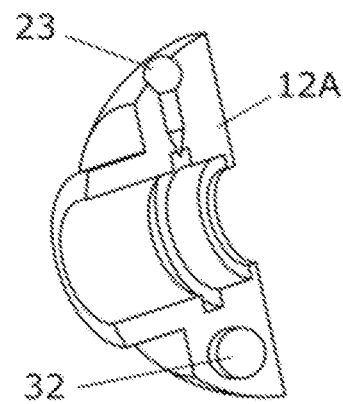
FIG. 29A　　　　FIG. 29B
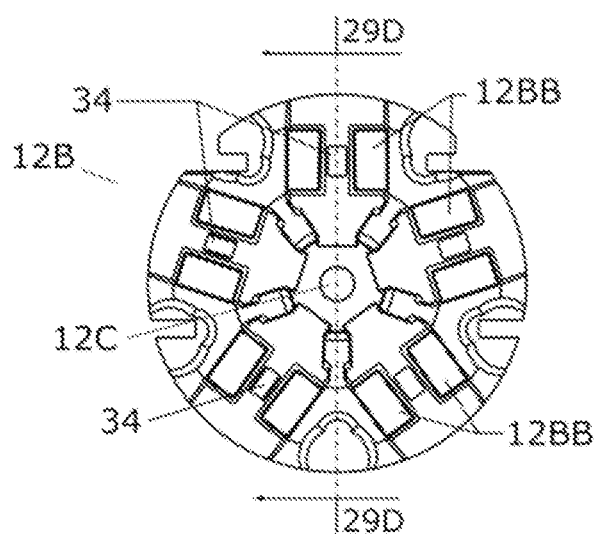
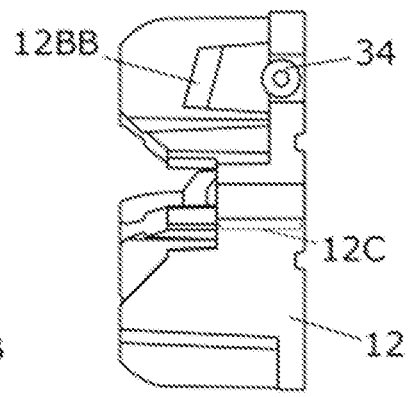
FIG. 29C　　　　FIG. 29D

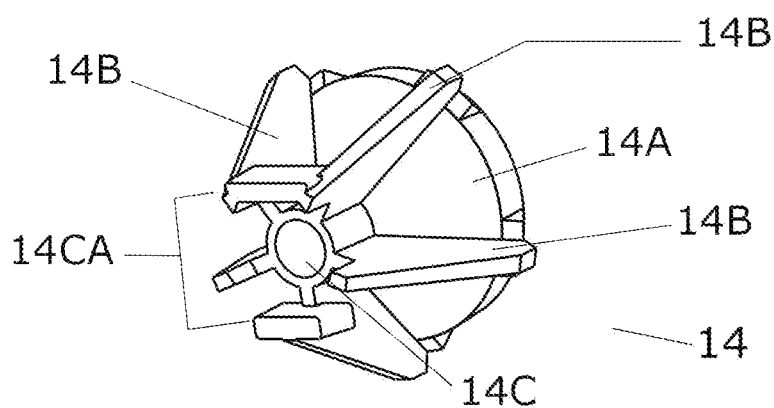
FIG. 30E
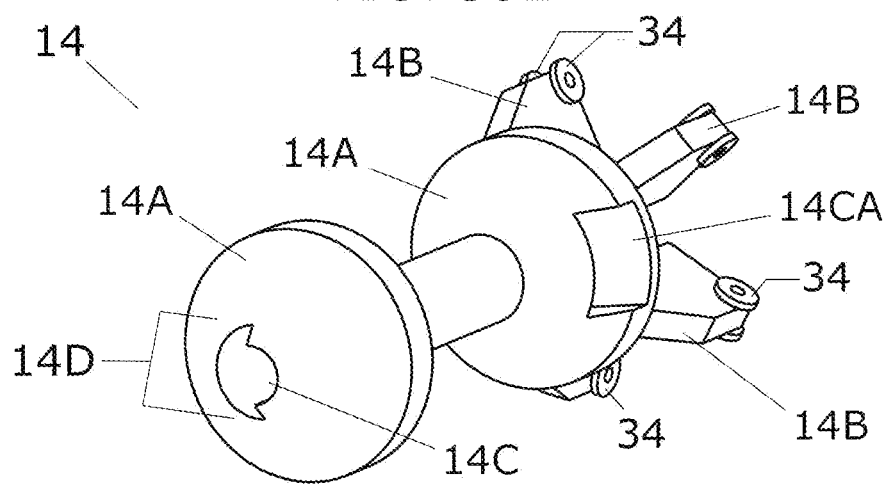
FIG. 30F
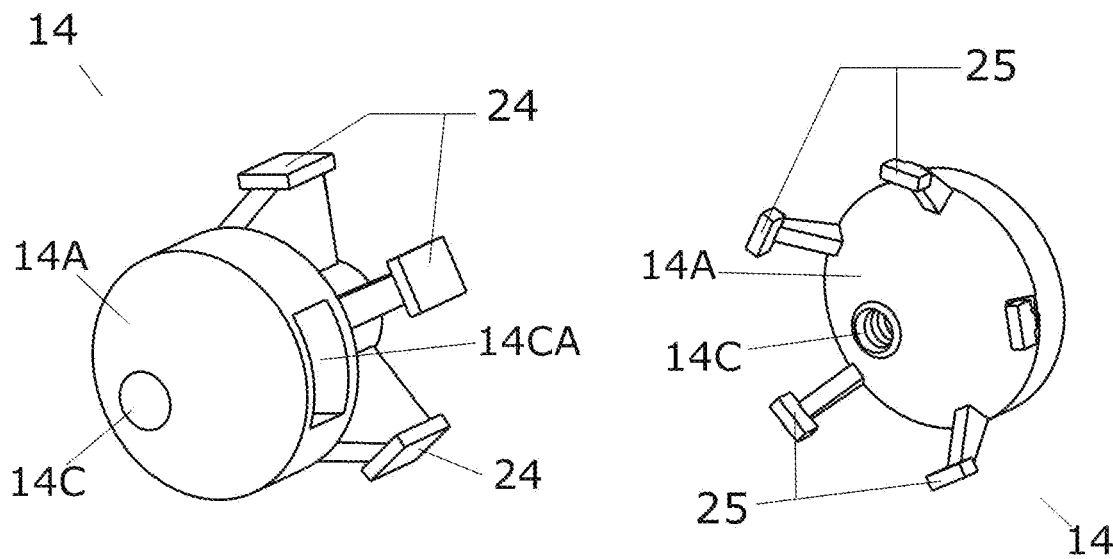
FIG. 30G
FIG. 30H

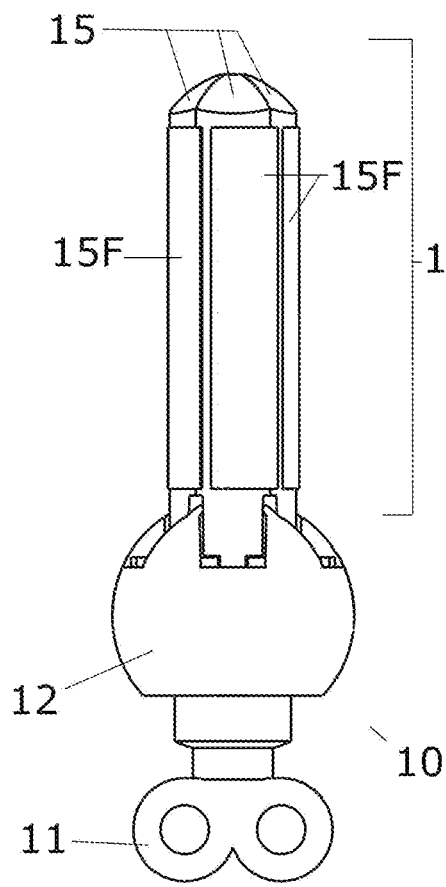
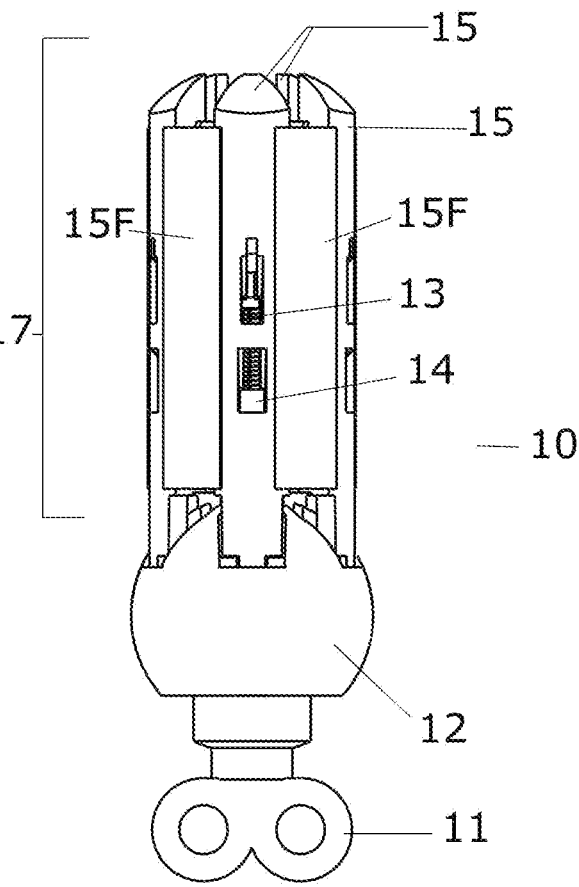
FIG. 35A  FIG. 35B
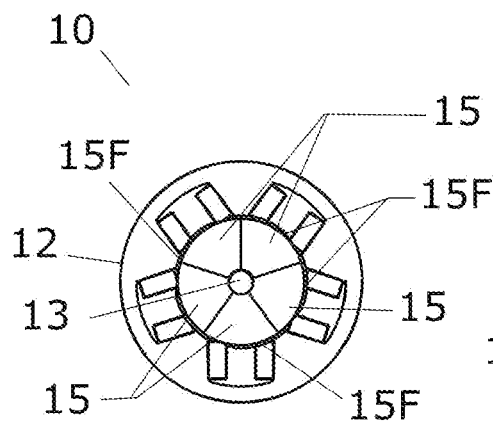
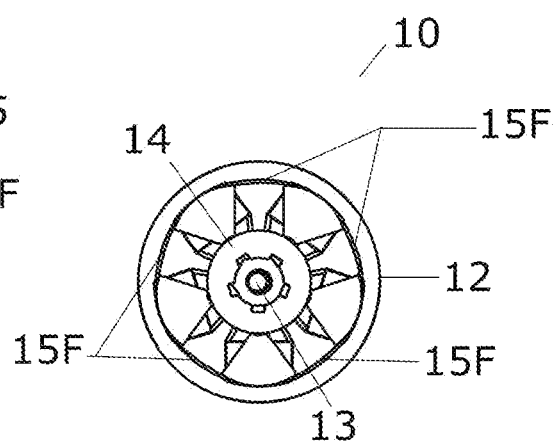
FIG. 35C  FIG. 35D

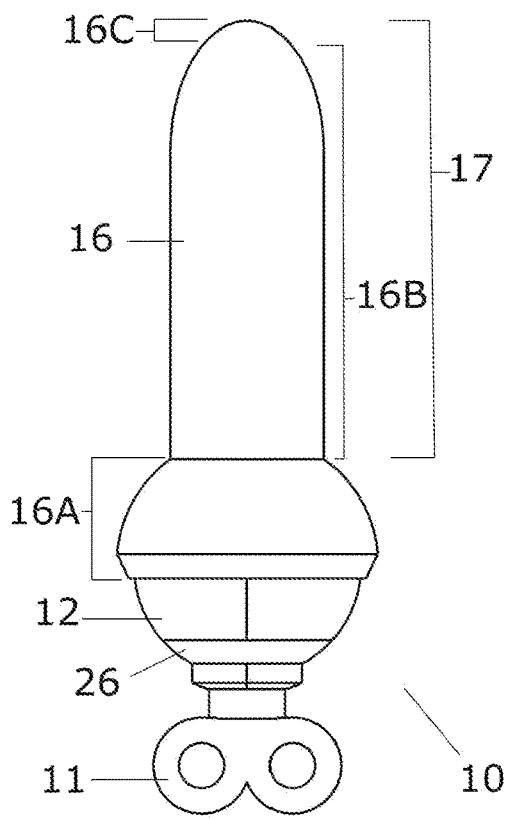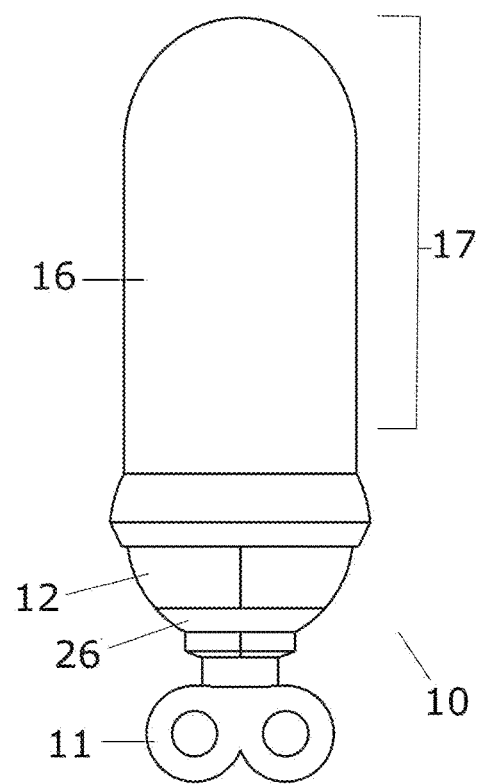
FIG. 39A
FIG. 39B
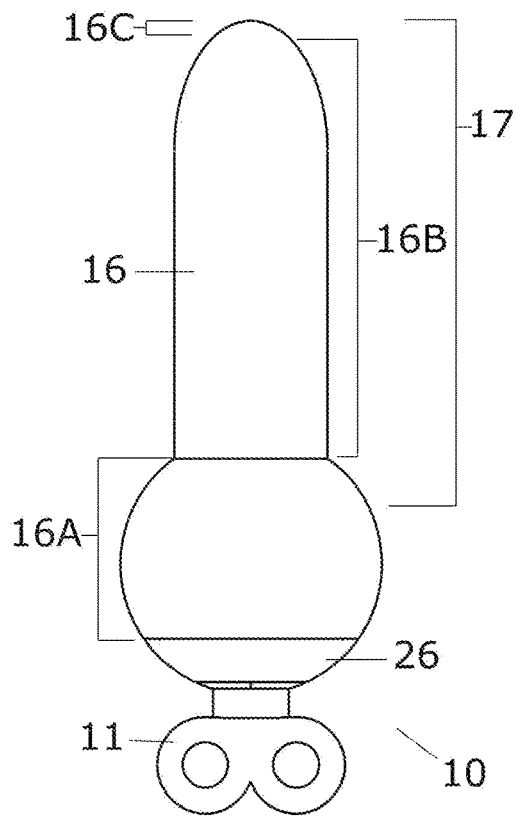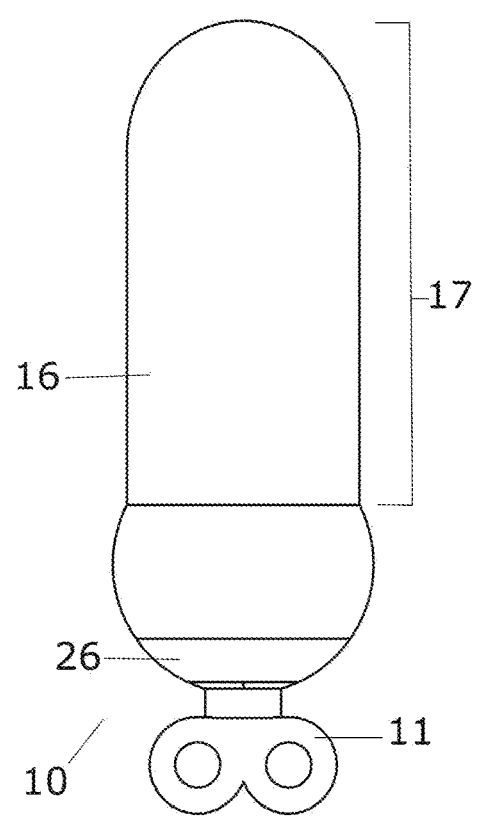
FIG. 39C
FIG. 39D

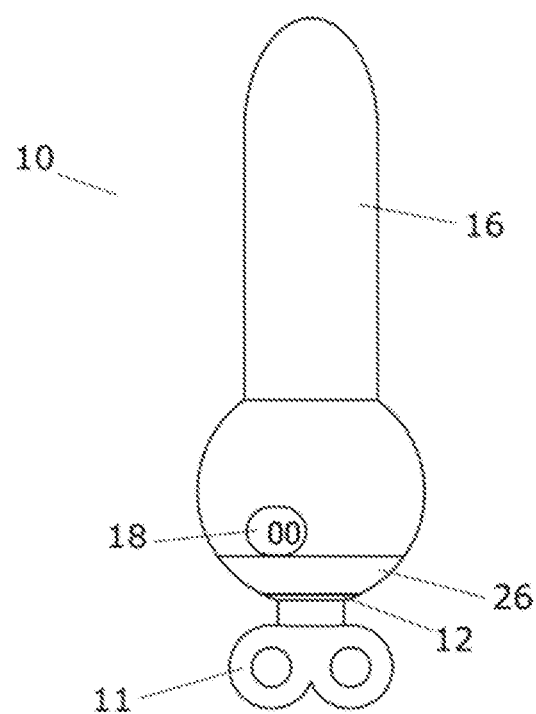
FIG. 51
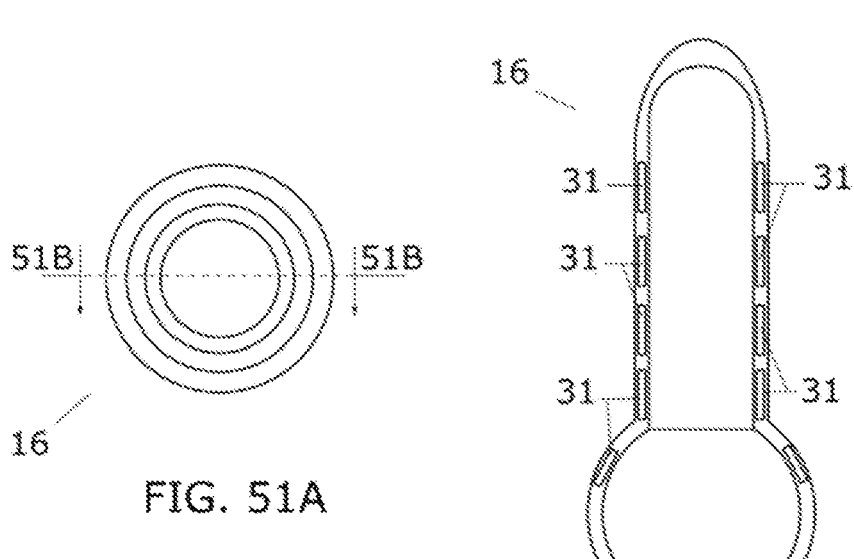
FIG. 51A
FIG. 51B

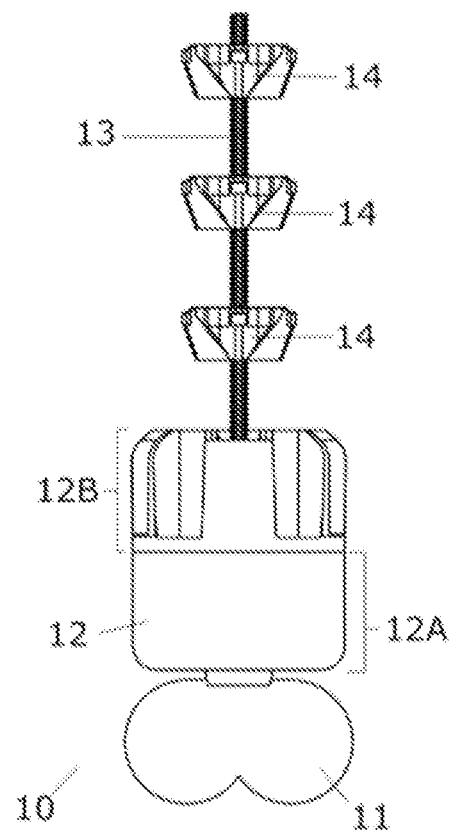
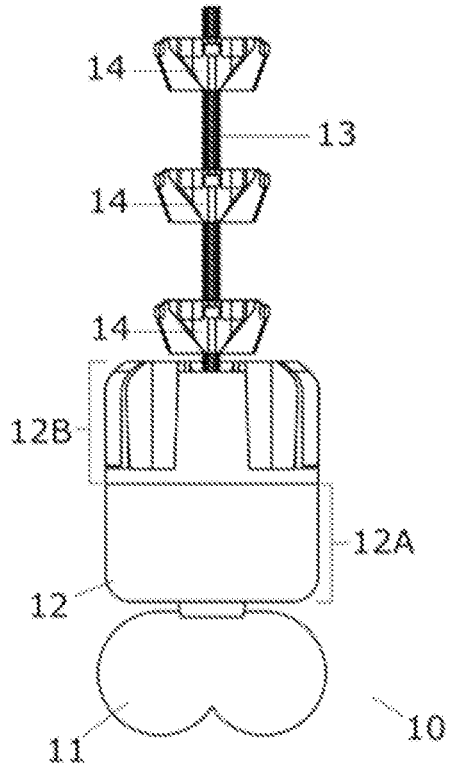
FIG. 57A    FIG. 57B
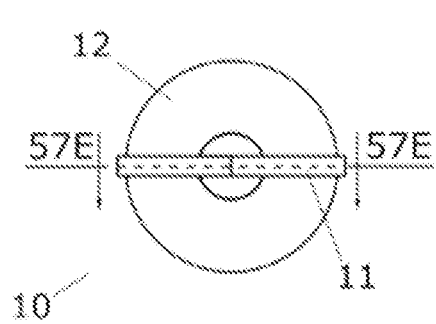
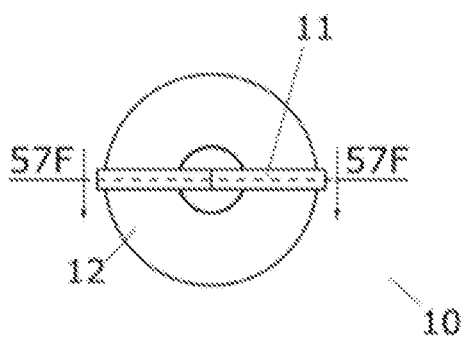
FIG. 57C    FIG. 57D

GIRTH ADJUSTABLE DEVICE

CROSS REFERENCE TO RELATED APPLICATION

This application claims the benefit of U.S. Provisional application No. 62/636,240, filed on Feb. 28, 2018 and the U.S. Nonprovisional application Ser. No. 16/005,679, filed on Jun. 12, 2018.

BACKGROUND OF THE INVENTION

Field of Invention

The present invention relates to a physical therapy apparatus and more specifically it relates to a girth adjustable device for the dilation and stretch of body orifices.

Description of Related Art

Devices like vaginal or rectal dilators for body orifice dilation and stretch have been a growing area of interest mainly for the following medical applications: gynecology, oncology, gastroenterology, and in some cases for some applications such as: body orifice improvement and activities pleasurable to the body. It concerns male and female.

A body orifice such as a vagina or an anus is a tubular body part. The body orifice shape can be considered as a hollow cylinder which means that a body orifice has a center, a diameter, a lateral surface area and a length. An efficient way to dilate and stretch a body orifice is to use a device that can repeatedly, gradually generate a uniform and sustainable pressure against the entire lateral surface area of a body orifice. The pressure should go from the center toward the lateral surface area of the body orifice.

As the body orifice can be considered as a sensitive body part, such devices should provide a safe, gradual and precise control of the pressure.

As the dilation and stretch of body orifices is a procedure that requires time, the user may prefer to keep such device in their body orifice and be able to freely do other activities, therefore such devices should be lightweight (which can be considered as non-motorized) and also be as compact as possible.

Currently, none of the devices on the market provide a girth adjustable device with a non-motorized version, a version with a removable controller, a version providing other features to enhance the body dilation procedure related to physical therapy and/or body orifice stimulation and a version that dilates and stretches two body orifices at the same time, wherein the user can repeatedly, safely, gradually, precisely and comfortably, generate a uniform and sustainable pressure against the entire lateral surface area of a body orifice.

Some of devices propose a set of fixed girth devices. For example, the document US 2007/0043388 discloses a set of a series of colored dilator devices to indicate the difference in girth size. The usage of such dilator set is confusing as the user has to manage several devices. The pressure generated against the lateral surface area of the body orifice is not gradual as each device has a fixed girth.

Other devices commonly referred to as inflatable devices have several drawbacks. Their design is commonly made of a fixed pump and a pipe that can be considered bulky by the user. The air-chamber used in those devices cannot provide a sustainable and precise pressure against the lateral surface area of the body orifice and have the risk of over-filling the device and rupturing in the body orifice.

BRIEF SUMMARY OF THE INVENTION

The present invention is a girth adjustable device, hereinafter referred to as «the device», for the dilation and stretch of body orifices, wherein the same can be utilized for such as but not limited to: medical applications, massage, body orifice improvement and activities pleasurable to the body (for example: body orifice stimulation and sexual stimulation).

The device preferably comprises a controller, a housing, a threaded shaft, at least two modules having at least one conical section with a slant height or at least one module having at least two conical sections with a slant height, a plurality of shaft members and a sheath. Attention being called to the fact that the device in its preferred embodiment is an assembly of only ten parts (or only eleven parts when configured with two modules having at least one conical section with a slant height, or only twelve parts when configured with three modules having at least one conical section with a slant height) which is a significant benefit in term of production and assembly.

The part of the device that can be inserted into a body orifice and whose girth size can be repeatedly adjusted safely, gradually, precisely and comfortably to generate a uniform and sustainable pressure against the entire lateral surface area of the body orifice, is referred to hereinafter as «the shaft».

The user via the controller can increase and decrease the girth size of the shaft of the device, which means adjust the girth size of the shaft at any size to perform the dilation and stretch procedure. The increase or decrease by the user via the controller of the girth size of the shaft is referred hereinafter to as «the adjustment». The user performs the adjustment. The adjustment has the following characteristics: repeatable, safe, gradual, precise, and comfortable for the user in which the device is inserted. Those characteristics of the adjustment are referred hereinafter to «the specific characteristics».

Therefore, attention being called to the fact that the device is such that when the user via the controller increases the girth size of the shaft in a body orifice, the device generates a safe, gradual, sustainable, and substantially uniform pressure against the entire lateral surface area of the body orifice. When the user via the controller decreases the girth size of the shaft, the pressure against the entire lateral surface area of the body orifice is reduced safely, gradually and uniformly. This performance is feasible partially due to the longitudinal and uniform configuration of a plurality of shaft members included into the device (five or six shaft members in the preferred embodiments of the device). The specific characteristics of the adjustment of the device allow the user to effectively perform the dilation and stretch of body orifices.

Attention being called to the fact that the device in its preferred embodiment is non-motorized and therefore it ensures a lightweight, compact and substantially noiseless device for an optimum utilization by the user.

There has thus been outlined, rather broadly, the more important features of the invention in order that the detailed description thereof may be better understood. There are additional features of the invention that will be described hereinafter and that will form the subject matter of the claims appended hereto.

It is to be understood that the device is not limited in its application to the details of construction and to the arrangements of the components set forth in the following description or illustrated in the drawings. The invention is capable of other embodiments and of being practiced and carried out in various ways. Also, it is to be understood that the phraseology and terminology employed hereinafter are for the purpose of the description and should not be regarded as limiting.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

FIG. 1A illustrates a front view of the device 10 with the shaft 17 at its minimum girth size according to a preferred embodiment of the device 10. FIG. 1B illustrates a front view of the device 10 with the shaft 17 at its maximum girth size according to a preferred embodiment of the device 10. FIG. 1C illustrates a top view of the device 10 with the shaft 17 at its minimum girth size according to a preferred embodiment of the device 10. FIG. 1D illustrates a front view of the device 10 with the shaft 17 at its maximum girth size according to a preferred embodiment of the device 10.

FIG. 18 illustrates a perspective view of the device 10 with the shaft 17 at its minimum girth size according to an embodiment of the device 10.

FIG. 19A illustrates a perspective view of the device 10 with the shaft 17 at its minimum girth size according to an embodiment of the device 10.

FIG. 29A illustrates a perspective view of a part of the housing 12 according to an embodiment of the device 10. FIG. 29B illustrates a perspective view of a part of the housing 12 according to an embodiment of the device 10. FIG. 29C illustrates a top view of a part of the housing 12 according to an embodiment. FIG. 29D illustrates a section view of FIG. 29C.

FIG. 30E illustrates a perspective view of a module 14 according to an embodiment. FIG. 30F illustrates a perspective view of a module 14 according to an embodiment. FIG. 30G illustrates a perspective view of a module 14 according to an embodiment. FIG. 30H illustrates a perspective view of a module 14 according to an embodiment.

FIG. 35A illustrates a front view of the device 10 with the shaft 17 at its minimum girth size according to an embodiment of the device 10 (sheath 16 not illustrated). FIG. 35B illustrates a front view of the device 10 with the shaft 17 at its maximum girth size according to an embodiment of the device 10 (sheath 16 not illustrated). FIG. 35C illustrates a top view of the device 10 with the shaft 17 at its minimum girth size according to an embodiment of the device 10 (sheath 16 not illustrated). FIG. 35D illustrates a top view of the device 10 with the shaft 17 at its maximum girth size according to an embodiment of the device 10 (sheath not illustrated).

FIG. 39A is a front view of the device 10 with the shaft 17 at its minimum girth size according to a preferred embodiment of the device 10. FIG. 39B is a front view of the device 10 with the shaft 17 at its maximum girth size according to a preferred embodiment of the device 10. FIG. 39C is a front view of the device 10 with the shaft 17 at its minimum girth size according to a preferred embodiment of the device 10. FIG. 39D is a front view of the device 10 with the shaft 17 at its maximum girth size according to a preferred embodiment of the device 10.

FIG. 50 illustrates a front view of the device 10 with the shaft 17 at its minimum girth size according to an embodiment of the device 10.

FIG. 51A illustrates a bottom view of the sheath 16 according to an embodiment. FIG. 51B illustrates a section view of FIG. 51A.

FIG. 57A illustrates a front view of the device 10 with the shaft 17 at its minimum girth size according to an embodiment of the device 10 (plurality of shaft members 15 and sheath 16 not illustrated). FIG. 57B illustrates a front view of the device 10 with the shaft 17 at its maximum girth size according to an embodiment of the device 10 (plurality of shaft members 15 and sheath 16 not illustrated). FIG. 57C illustrates a bottom view of FIG. 57A. FIG. 57D illustrates a bottom view of FIG. 57B.

DETAILED DESCRIPTION OF THE INVENTION

Figure 2A:
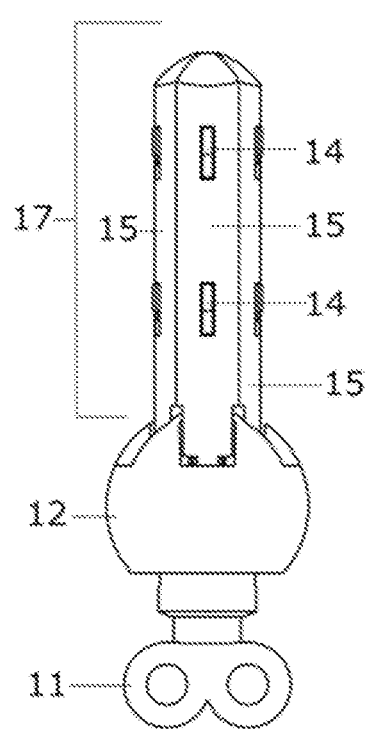
FIG. 2A illustrates a front view of the device 10 with the shaft 17 at its minimum girth size according to a preferred embodiment of the device 10 (sheath 16 not illustrated).
Figure 2B:
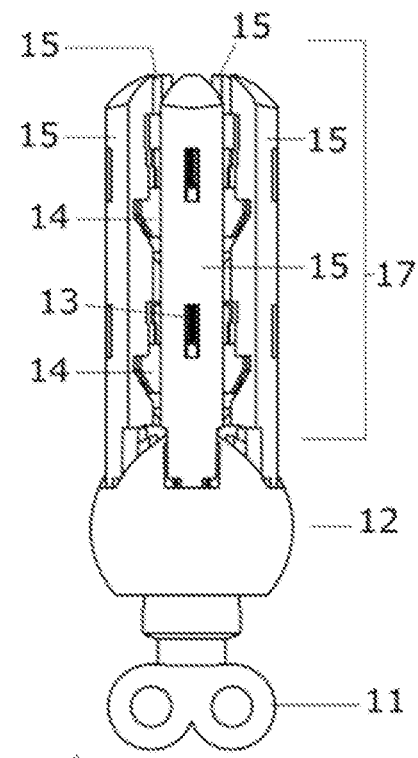
FIG. 2B illustrates a front view of the device 10 with the shaft 17 at its maximum girth size according to a preferred embodiment of the device 10 (sheath 16 not illustrated).
Figure 2C:
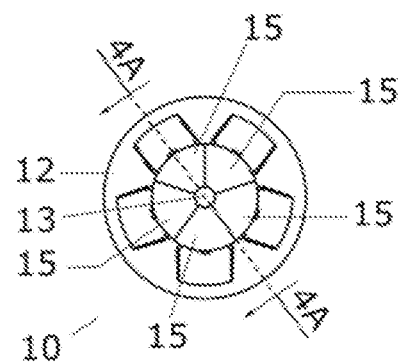
FIG. 2C illustrates a top view of the device 10 with the shaft 17 at its minimum girth size according to a preferred embodiment of the device 10 (sheath 16 not illustrated).
Figure 2D:
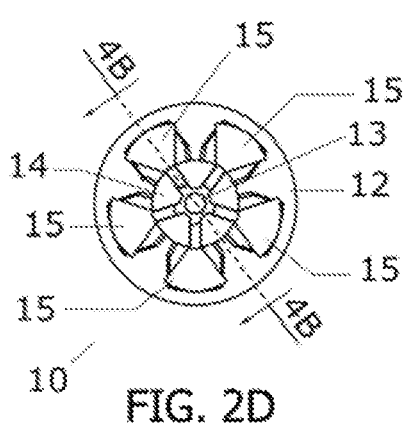
FIG. 2D illustrates a top view of the device 10 with the shaft 17 at its maximum girth size according to a preferred embodiment of the device 10 (sheath 16 not illustrated).
Figure 3A:
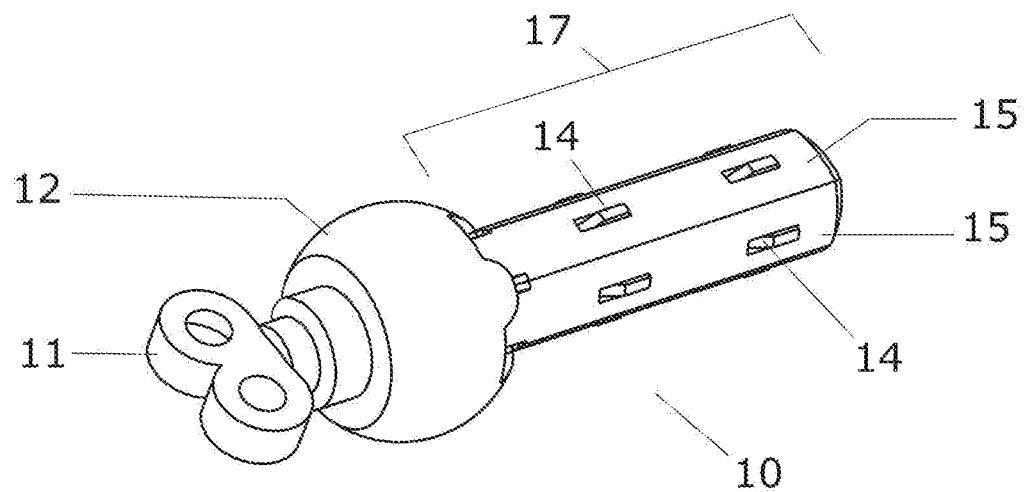
FIG. 3A illustrates a perspective view of the device 10 with the shaft 17 at its minimum girth size according to a preferred embodiment of the device 10 (sheath 16 not illustrated).
Figure 3B:
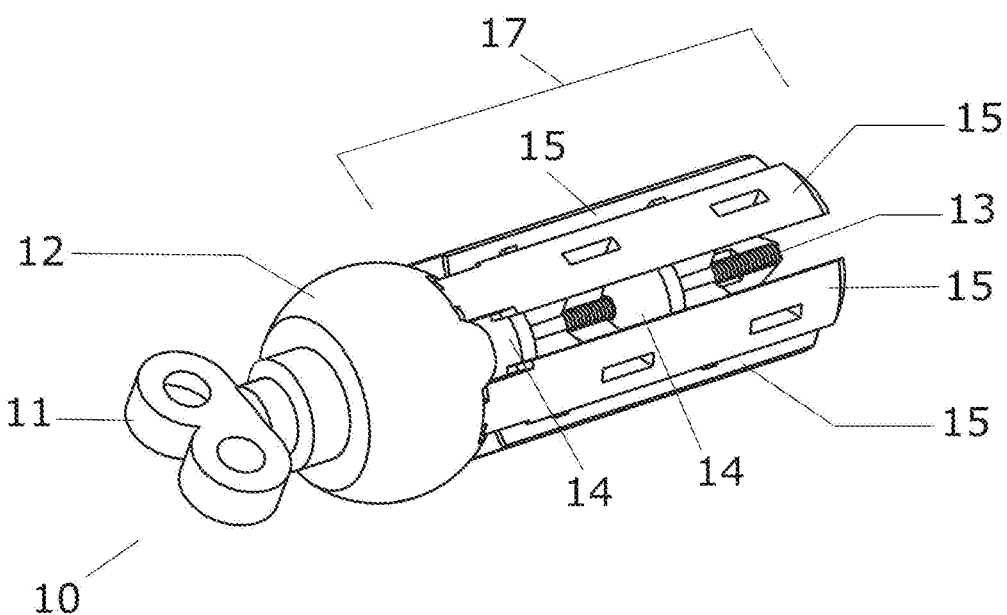
FIG. 3B illustrates a perspective view of the device 10 with the shaft 17 at its maximum girth size according to a preferred embodiment of the device 10 (sheath 16 not illustrated).
Figure 4A:
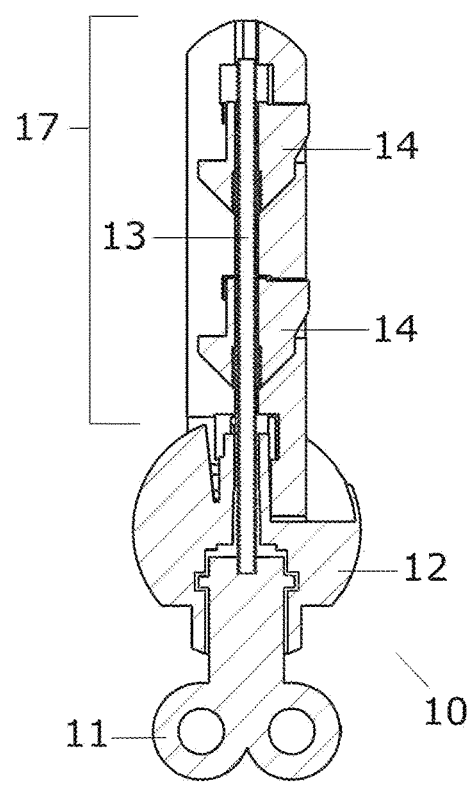
FIG. 4A illustrates a section view of FIG. 2C.
Figure 4B:
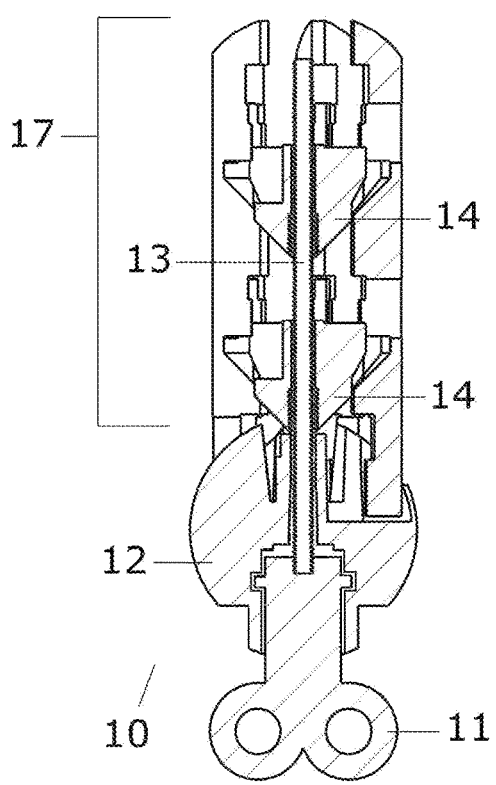
FIG. 4B illustrates a section view of FIG. 2D.
Figure 4C:
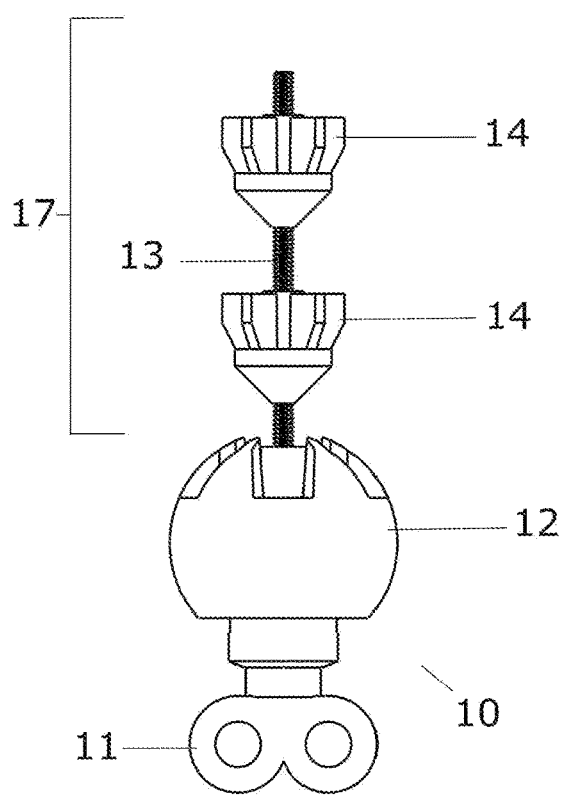
FIG. 4C illustrates a front view of the device 10 with the shaft 17 at its minimum girth size according to a preferred embodiment of the device 10 (sheath 16 and plurality of shaft members 15 not illustrated).
Figure 4D:
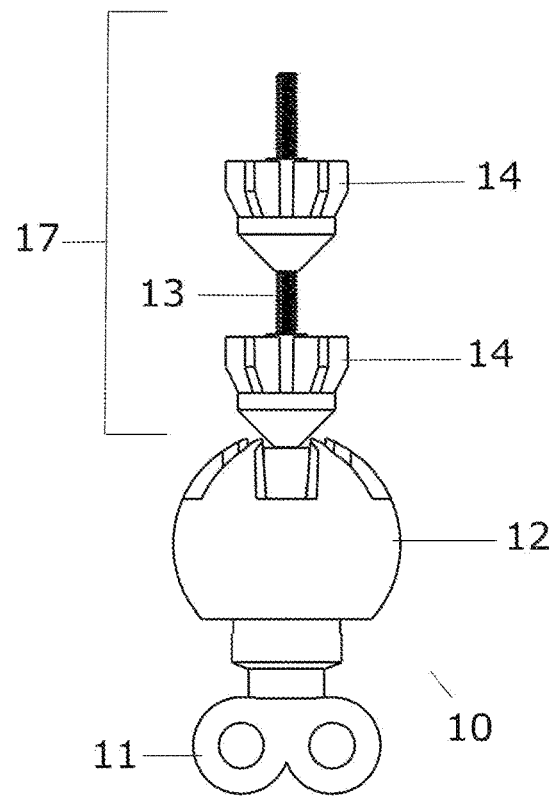
FIG. 4D illustrates a front view of the device 10 with the shaft 17 at its maximum girth size according to a preferred embodiment of the device 10 (sheath 16 and plurality of shaft members 15 not illustrated).

As used herein, the term «and/or» includes any and all combinations of one or more of the associated listed items. As used herein, the singular forms «a», «an», «and» and «the» are intended to include the plural forms as well as the singular forms, unless the context clearly indicates otherwise. It will be further understood that the terms, «has», «having», «configured», «is (or are) configured», «may be configured», «comprise», «comprises» and/or «comprising», when used in this specification, specify the presence of stated features, members, parts, elements, and/or components, but do not preclude the presence or addition of one or more other features, members, parts, elements, component, and/or groups thereof.

The term «plastic» means a material made predominantly of plastic and includes the combination of plastic with another plastic, material and/or element. The terms «metal» means a material made predominantly of metal and includes the combination of metal with another metal, material and/or element. The term «silicone» means a material made predominantly of silicone and includes the combination of silicone with another silicone, material and/or element. The term «rubber» means a material made predominantly of rubber and includes the combination of rubber with another rubber, material and/or element. The term «wood» means a material made predominantly of wood and includes the combination of wood with another wood, material and/or element. The term «leather» means a material made predominantly of leather and includes the combination of leather with another leather, material and/or element. The term «glass» means a material made predominantly of glass and includes the combination of glass with another glass, material and/or element. The term «rigid material» means a material predominantly rigid and includes the combination of rigid material with another material. The term «semi-rigid material» means a material predominantly semi-rigid and includes the combination of semi-rigid material with another material. The term «soft material» means a material predominantly soft and includes the combination of soft material with another material. The term «secured to» means: attached, fixed or fastened so as not to give way, become loose, or be lost.

Turning now descriptively to the drawings, in which similar reference characters denote similar elements through the several views.

Preferred Embodiment of the Device

FIG. 1, FIG. 2, FIG. 3, and FIG. 4 illustrate the device 10, which preferably comprises a controller 11, a housing 12, a threaded shaft 13 (illustrated in FIG. 2, FIG. 3 and FIG. 4), at least two modules 14 having at least one conical section with a slant height (illustrated in FIG. 2, FIG. 3, and FIG. 4) or at least one module 14 having at least 405 two conical sections with a slant height (not illustrated in FIG. 1, FIG. 2, FIG. 3, and FIG. 4), at least five shaft members 15 and a sheath 16 (illustrated in FIG. 1). As illustrated in FIG. 1A and FIG. 1B, the shaft 17 of the device 10 is going from the tip end 16C of the sheath 16 to the closest edge at the perimeter of the housing 12. FIG. 1A illustrates a front view of the device 10 with the shaft 17 at its minimum girth size according to a preferred embodiment of the device 10. FIG. 1B illustrates a front view of the device 10 with the shaft 17 at its maximum girth size according to a preferred embodiment of the device 10. FIG. 1C illustrates a top view of the device 10 with the shaft 17 at its minimum girth size according to a preferred embodiment of the device 10. FIG. 1D illustrates a top view of the device 10 with the shaft 17 at its maximum girth size according to a preferred embodiment of the device 10. The girth size of the shaft 17 is adjustable to any size from its minimum girth size to its maximum girth size, which means that the adjustment results to any size of the girth size of the shaft 17, from its minimum girth size to its maximum girth size and from its maximum girth size to its minimum girth size. The increments of increase and decrease of the girth size of the shaft 17 depends on the rotation of the controller 11 and the quantity of threads per inch of the threaded shaft 13. For a better understanding of the mechanism of the device 10, the sheath 16 is not illustrated in FIG. 2 and FIG. 3. FIG. 2A illustrates a front view of the device 10 with the shaft 17 at its minimum girth size according to a preferred embodiment of the device 10. FIG. 2B illustrates a front view of the device 10 with the shaft 17 at its maximum girth size according to a preferred embodiment of the device 10. FIG. 2C illustrates a top view of the device 10 with the shaft 17 at its minimum girth size according to a preferred embodiment of the device 10. FIG. 2D illustrates a top view of the device 10 with the shaft 17 at its maximum girth size according to a preferred embodiment of the device 10. FIG. 3A illustrates a perspective view of the device 10 with the shaft 17 at its minimum girth size according to a preferred embodiment of the device 10. FIG. 3B illustrates a perspective view of the device 10 with the shaft 17 at its maximum girth size according to a preferred embodiment of the device 10. For a better understanding of the mechanism of the device 10, the sheath 16 and the plurality of shaft members 15 are not illustrated in FIG. 40 and FIG. 4D. FIG. 4C illustrates a front view of the device 10 with the shaft 17 at its minimum girth size according to a preferred embodiment of the device 10 (sheath 16 and plurality of shaft members 15 not illustrated). FIG. 4D illustrates a front view of the device 10 with the shaft 17 at its maximum girth size according to a preferred embodiment of the device 10 (sheath 16 and plurality of shaft members 15 not illustrated).

The threaded shaft 13 (illustrated in FIG. 5B) has a first end 13A, a middle section 13B and a second end 13C. The direction of orientation going from the first end 13A to the second end 13C or from the second end 130 to the first end 13A of the threaded shaft 13 is referred hereinafter to as "the longitudinal axis of the threaded shaft". A shaft member 15 (illustrated in FIG. 31) has a first end 15A having at least one housing groove 15AA, a middle section 15B, at least one module cavity 150 with a sloped edge 15CA, at least one module connector groove 15D, and a tip end 15E. The direction of orientation going from the first end 15A to the tip end 15E or from the tip end 15E to the first end 15A of the shaft member 15 is referred hereinafter to as "the longitudinal axis of the shaft member".

The controller 11 is connected to the threaded shaft 13 inside the housing 12, the module 14 (or a plurality of modules 14) receives the threaded shaft 13, the module 14 (or a plurality of modules 14) is slidably connected to the plurality of shaft members 15, the plurality of shaft members 15 is slidably connected to the housing 12, the plurality of shaft members 15 surrounds the module 14 (or a plurality of modules 14), each longitudinal axis of each shaft member 15 is approximatively or exactly parallel with the longitudinal axis of the threaded shaft 13, the sheath 16 is connected to the plurality of shaft members 15 or to the plurality of shaft members 15 and the housing 12, the sheath 16 surrounds the plurality of shaft members 15 or the plurality of shaft members 15 and the housing 12. In a preferred embodiment, the assembly of the controller 11, the housing 12, the threaded shaft 13, the module 14 (or a plurality of modules 14), the plurality of shaft members 15 and the sheath 16 characterized the device 10, such that when the user rotates the controller 11 clockwise, the threaded shaft 13 rotates clockwise, making the module 14 (or a plurality of modules 14) prevented from rotating around the longitudinal axis of the threaded shaft 13, travel along the threaded shaft 13 in the direction of the housing 12, making each shaft member 15 travel perpendicularly to the longitudinal axis of the threaded shaft 13 in the opposite direction of the longitudinal axis of the threaded shaft 13, each longitudinal axis of each shaft member 15 is maintained approximatively or exactly parallel with the longitudinal axis of the threaded shaft 13, the sheath 16 made of a resilient material, deforms elastically from its original shape, the girth size of the shaft 17 increases, until the controller 11 is no longer rotated clockwise by the user, meaning that the user reached the desired girth size of the shaft 17, meaning that the threaded shaft 13 is no longer rotated, the module 14 (or a plurality of modules 14) no longer travels along the threaded shaft 13, each shaft member 15 no longer travels perpendicularly to the longitudinal axis of the threaded shaft 13 in the opposite direction of the longitudinal axis of the threaded shaft 13, the sheath 16 no longer deforms elastically, the girth size of the shaft 17 is stopped from increasing. The girth size of the shaft 17 is sustained at this size. Then, when the user rotates counter-clockwise the controller 11, the threaded shaft 13 rotates counter-clockwise, making the module 14 (or a plurality of modules 14) prevented from rotating around the longitudinal axis of the threaded shaft 13, travel back along the threaded shaft 13 in the opposite direction of the housing 12, the sheath retrieves its original shape, making each shaft member 15 travel back perpendicularly to the longitudinal axis of the threaded shaft 13 in the direction of the longitudinal axis of the threaded shaft 13, each longitudinal axis of each shaft member 15 is maintained approximatively or exactly parallel with the longitudinal axis of the threaded shaft 13, the girth size of the shaft 17 decreases, until the controller 11 is no longer rotated counter-clockwise by the user, meaning that the user reached the desired girth size of the shaft 17, meaning that the threaded shaft 13 is no longer rotated, the module 14 (or a plurality of modules 14) no longer travels along the threaded shaft 13, each shaft member 15 no longer travels perpendicularly to the longitudinal axis of the threaded shaft 13 in the direction of the longitudinal axis of the threaded shaft 13, the sheath 16 no longer retrieves its original shape, the girth size of the shaft 17 is stopped from decreasing. The girth size of the shaft 17 is sustained at this size, until the user rotates again the controller 11 clockwise or counter-clockwise.

The controller 11 can no longer be rotated when the user reached the maximum girth size of the shaft 17 offered by the device 10, meaning that the threaded shaft 13 can no longer be rotated due to the fact that at least one module 14 is stopped from traveling along the threaded shaft 13 by pressing against at least one edge of the housing 12, and/or by pressing against at least one maximum translation stopper 13E (preferred embodiment illustrated in FIG. 22A), and/or by pressing against at least one edge of the module connector groove 15D (module connector groove 15D illustrated in FIG. 31) of at least one shaft member 15, and/or that at least one shaft member 15 is stopped from traveling perpendicularly to the longitudinal axis of the threaded shaft 13 in the opposite direction of the longitudinal axis of the threaded shaft 13 by pressing against at least one edge of the housing 12.

Figure 22A:
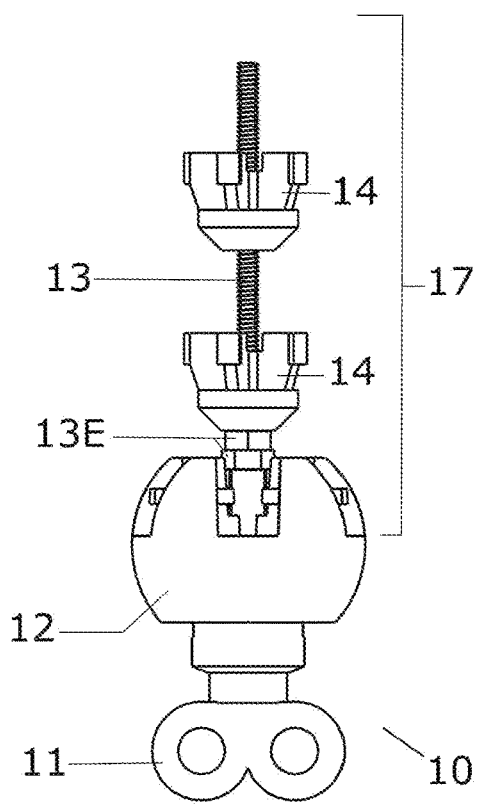
FIG. 22A illustrates a front view of the device 10 with the shaft 17 at its maximum girth size according to an embodiment of the device 10 (sheath 16 and plurality of shaft members 15 not illustrated).
Figure 22B:
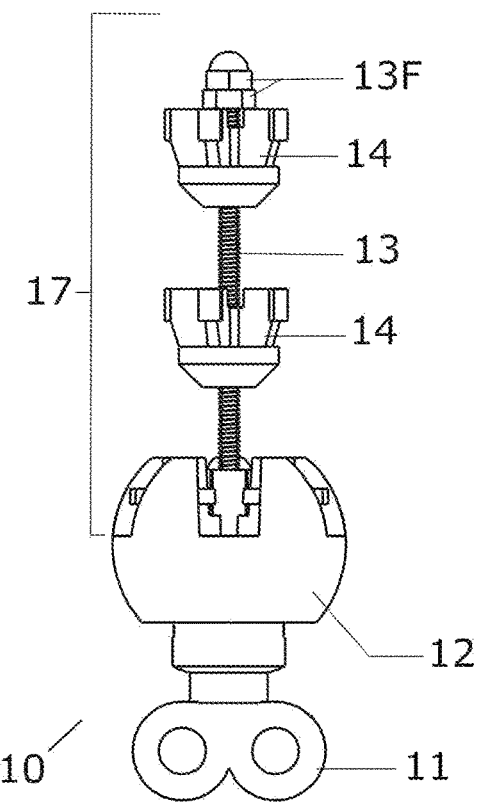
FIG. 22B illustrates a front view of the device 10 with the shaft 17 at its minimum girth size according to an embodiment of the device 10 (sheath 16 and plurality of shaft members 15 not illustrated).

The controller 11 can no longer be rotated when the user reached the minimum girth size of the shaft 17 offered by the device 10, meaning that the threaded shaft 13 can no longer be rotated due to the fact that at least one module 14 is stopped from traveling along the threaded shaft 13 by pressing against at least one edge of the module cavity 15C of at least one shaft member 15 (module cavity 15C illustrated in FIG. 31) and/or in another preferred embodiment illustrated in FIG. 22B, by pressing against at least one minimum translation stopper 13F.

Controller

The controller 11 is characterized by its function to control the clockwise and counter-clockwise rotation of the threaded shaft 13. In a preferred embodiment the device 10 comprises one controller 11. In a preferred embodiment of the device 10, the controller 11 is directly operated by the user, meaning that the user using at least one hand, rotates clockwise or counter-clockwise the controller 11, however, in another embodiment, the controller 11 may be operated by the user via an electronic part 18 (electronic part 18 described in the Electronic part section), when the controller 11 is connected to an enclosed electric motor 19 (enclosed electric motor 19 described in Enclosed electric motor section).

Figure 5B:
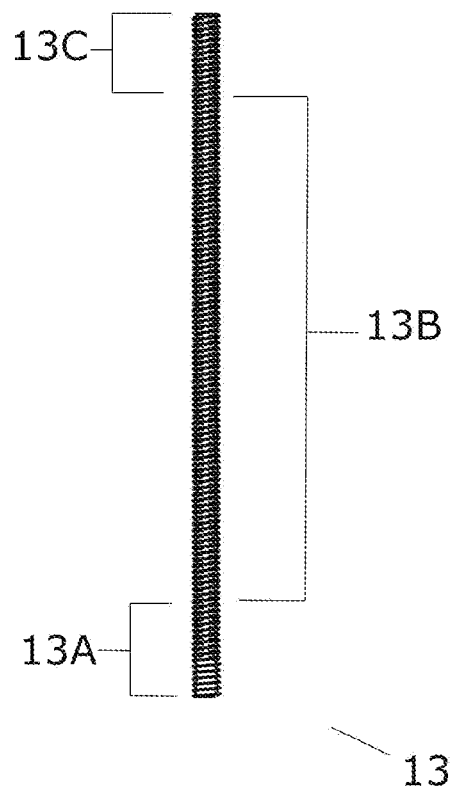
FIG. 5B illustrates a front view of the threaded shaft 13 according to a preferred embodiment of the device 10.
Figure 5C:
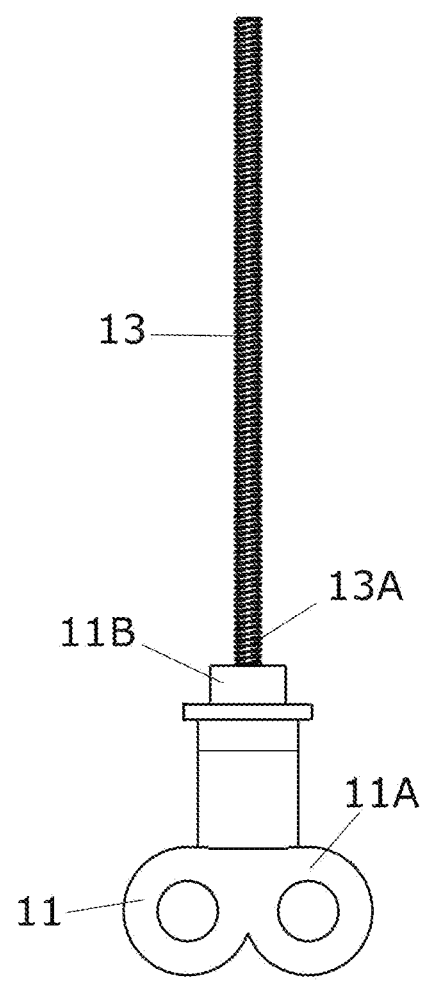
FIG. 5C illustrates a front view of the controller 11 connected to the threaded shaft 13 according to a preferred embodiment of the device 10.
Figure 5A:
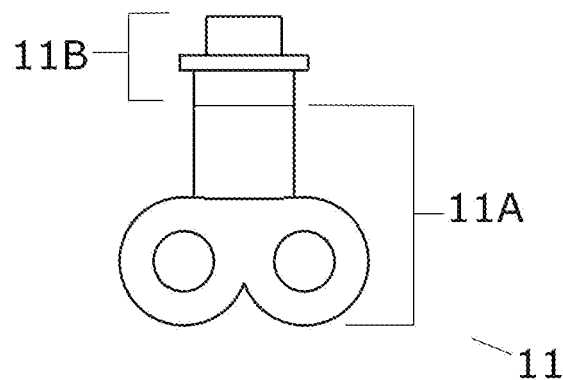
FIG. 5A illustrates a front view of the controller 11 according to a preferred embodiment of the device 10.
Figure 5D:
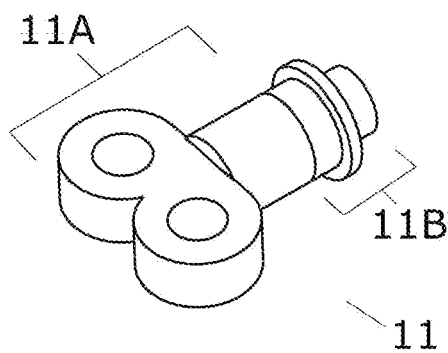
FIG. 5D illustrates a perspective view of the controller 11 according to a preferred embodiment of the device 10.
Figure 6A:
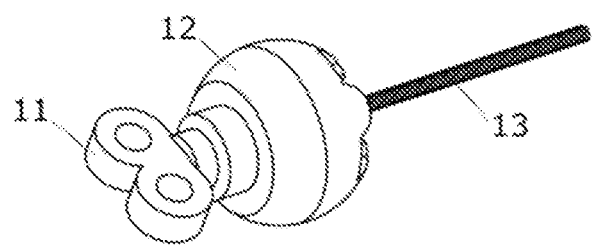
FIG. 6A illustrates a perspective view of the controller 11 connected to the threaded shaft 13 inside the housing 12 according to a preferred embodiment of the device 10.
Figure 6B:
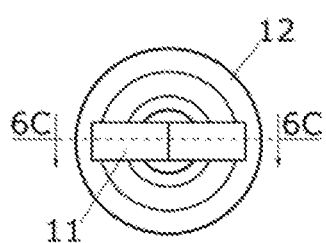
FIG. 6B illustrates a bottom view of the controller 11 connected to the threaded shaft 13 inside the housing 12 according to a preferred embodiment of the device 10.
Figure 6C:
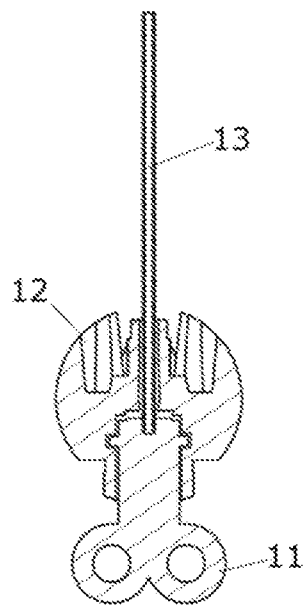
FIG. 6C illustrates a section view of FIG. 6B.
Figure 7A:
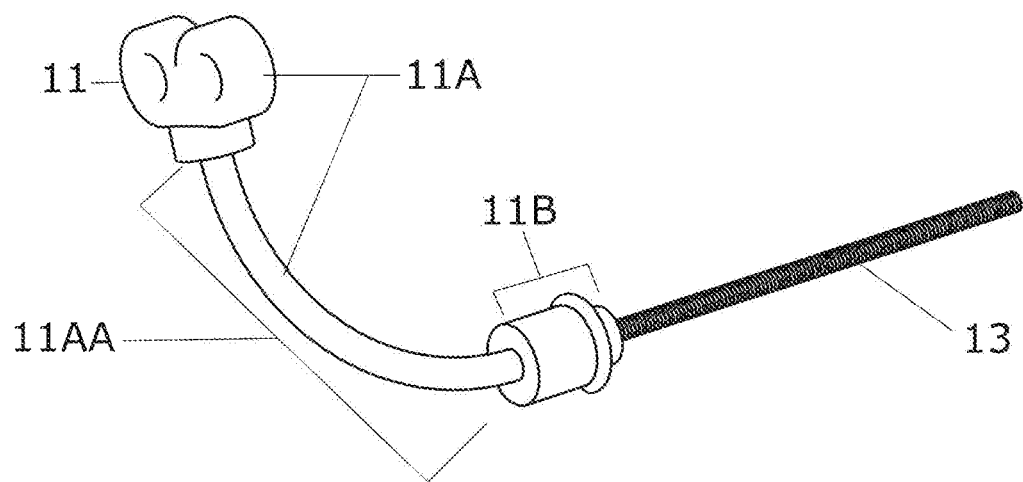
FIG. 7A illustrates a perspective view of the controller 11 connected to the threaded shaft 13 according to an embodiment of the device 10.
Figure 7B:
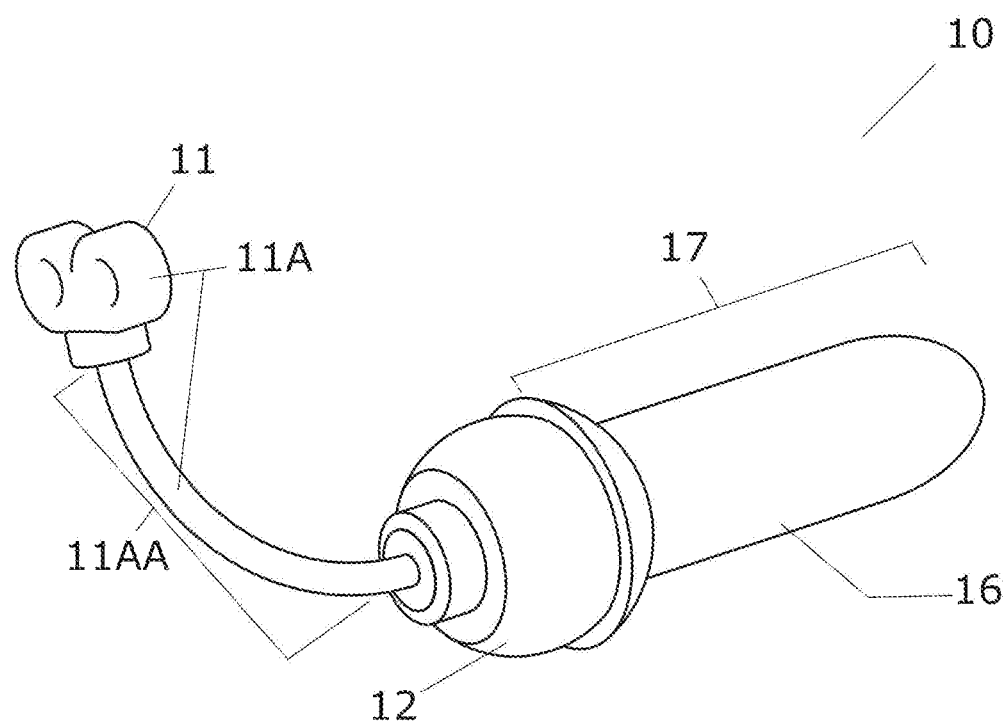
FIG. 7B illustrates a perspective view of the device 10 with the shaft 17 at its minimum girth size according to an embodiment of the device 10.

In a preferred embodiment illustrated in FIG. 5A and FIG. 5D, the controller 11 has a first end 11A and a second end 11B. Preferably, the controller first end 11A is connected to the second end 11B such that when the first end 11A is rotated by the user, the second end 11B rotates following the rotation of the first end 11A. As illustrated in FIG. 5C, the second end 11B connects the first end 13A of the threaded shaft 13 (illustrated in FIG. 5B), such that when the second end 11B rotates, the threaded shaft 13 rotates following the rotation of the second end 11B. As illustrated in FIG. 6, the second end 11B of the controller 11 and the first end 13A of the threaded shaft 13 are configured to fit inside the housing 12, wherein the second end 11B of the controller 11 and the first end 13A of the threaded shaft 13 can only rotate clockwise and counter-clockwise around the longitudinal axis of the threaded shaft 13. Preferably, the first end 11A of the controller 11 is configured with an ergonomic shape that facilitates its control by the user, with one or both hands. Preferably, the controller 11 is made with at least one coloration additive, however, the controller 11 may be made with no coloration additive. Preferably, the first end 11A of the controller 11 is configured in a geometric shape approximately or exactly, such as but not limited to: a key shape, a suction cup shape (as illustrated in FIG. 18), a knob shape (as illustrated in FIG. 19A), a cylinder shape, a heart shape, an animal tail shape, a knuckle punch shape, a polyhedron shape, a gemstone shape, a human face shape, an animal face shape, and/or a potatoid shape. The first end 11A of the controller 11 may be configured as such as but not limited to: a coupling nut, a motor shaft coupler, and a crank (foldable or not). Preferably, the controller 11 is made of a rigid material such as but not limited to: plastic, hard rubber, metal, glass and/or wood, however, the controller 11 may be made of a semi-rigid material such as but not limited to: plastic, silicone, and/or rubber, or the controller 11 may be made of a rigid material in combination with a semi-rigid and/or a soft material such as but not limited to: silicone, leather, and/or rubber. The controller 11 when made of metal, may be magnetized to increase the blood flow, relaxes muscles and ligaments of the body orifice region and therefore enhance the dilation and stretch of the body orifice during the utilization of the device 10. The first end 11A may be configured with a flexible shaft 11AA as illustrated in FIG. 7, such that when the first end 11A configured with a flexible shaft 11AA is rotated clockwise or counter-clockwise by the user, the second end 11B and the threaded shaft 13 rotate following the rotation of the first end 11A configured with a flexible shaft 11AA. The flexible shaft 11AA may be such as but not limited to: a wire rope, a flexible snake drill shaft and/or a flexible coil. The flexible shaft 11AA may comprise a covering, which bends but does not rotate. The flexible shaft 11AA may comprise a covering with a handle. The controller 11 may be configured with at least one color code and/or at least one serial number to distinguish a device 10 from another device 10 to facilitate the utilization for the user of several devices 10 (having or not the same features). The controller 11 may be configured with at least one visual and/or tactile indication to indicate to the user how to use the device 10.

Figure 8:
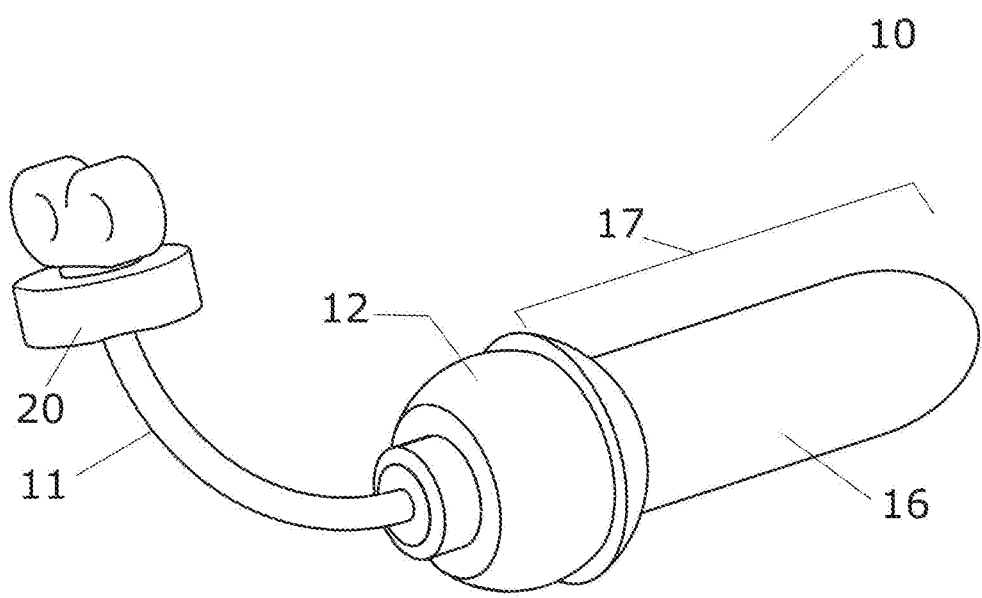
FIG. 8 illustrates a perspective view of the device 10 with the shaft 17 at its minimum girth size according to an embodiment of the device 10.

In another embodiment, as illustrated in FIG. 8, the controller 11 may comprise at least one handle having a bearing 20. Preferably, the handle having a bearing 20 comprises at least one such as but not limited to: a plain bearing and/or a rolling-element bearing. This embodiment is an alternative for the utilization of the controller 11, as the user with one hand can hold a handle having a bearing 20 and with the other hand can rotate the first end 11A of the controller 11 to perform the adjustment of the device 10.

Figure 9:
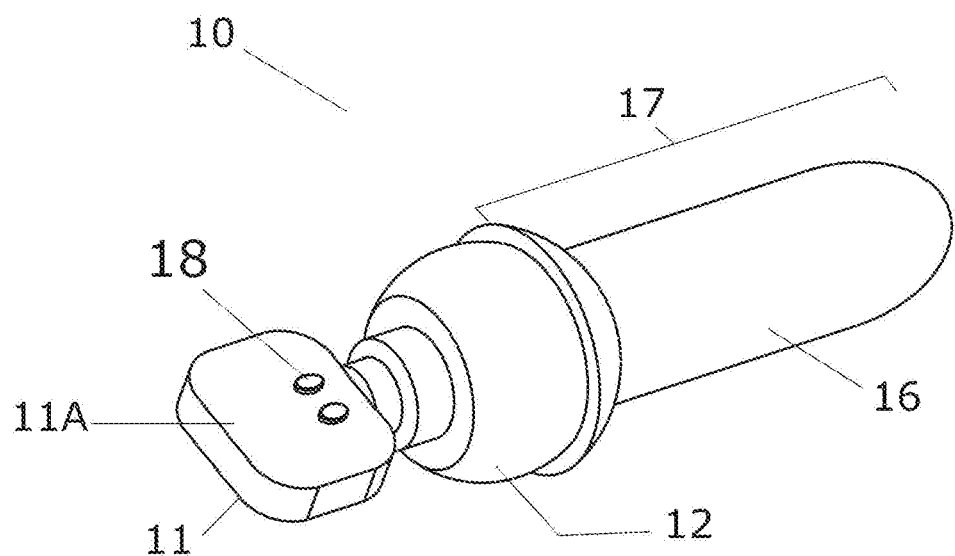
FIG. 9 illustrates a perspective view of the device 10 with the shaft 17 at its minimum girth size according to an embodiment of the device 10.

In another embodiment as illustrated in FIG. 9, the controller 11 may comprise at least one electronic part 18 (electronic part 18 described in Electronic part section).

Figure 10A:
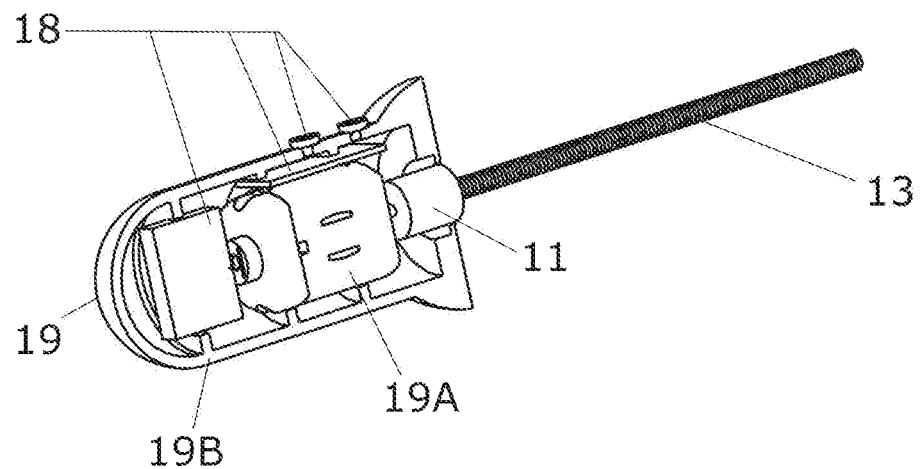
FIG. 10A illustrates a perspective view of the enclosed electric motor 19 (only one part of the motor housing 19B is illustrated) connected to the controller 11, which is connected to the threaded shaft 13 according to an embodiment of the device 10.
Figure 10B:
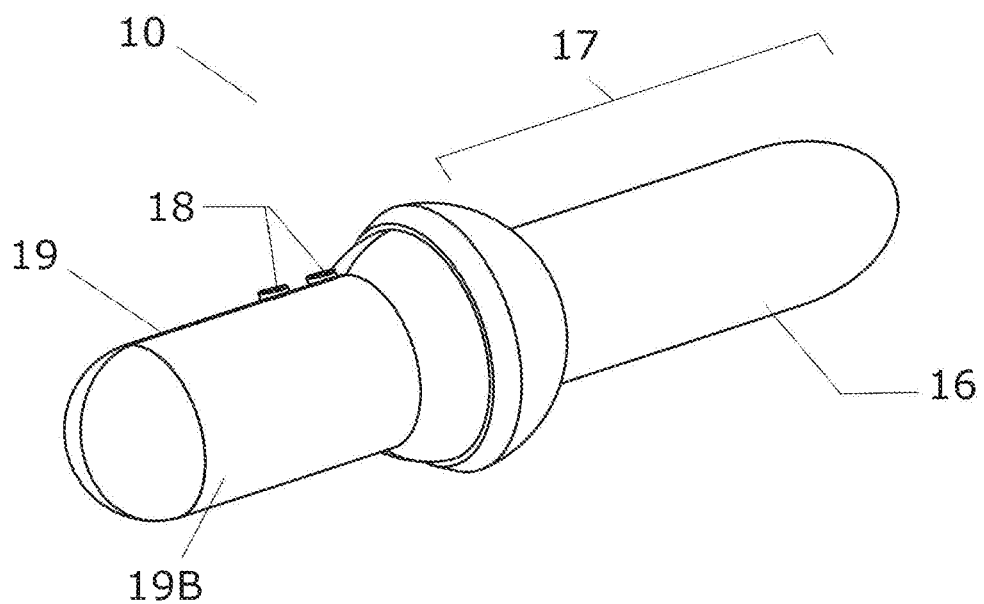
FIG. 10B illustrates a perspective view of the device 10 with the shaft 17 at its 155 minimum girth size according to an embodiment of the device 10.
Figure 11:
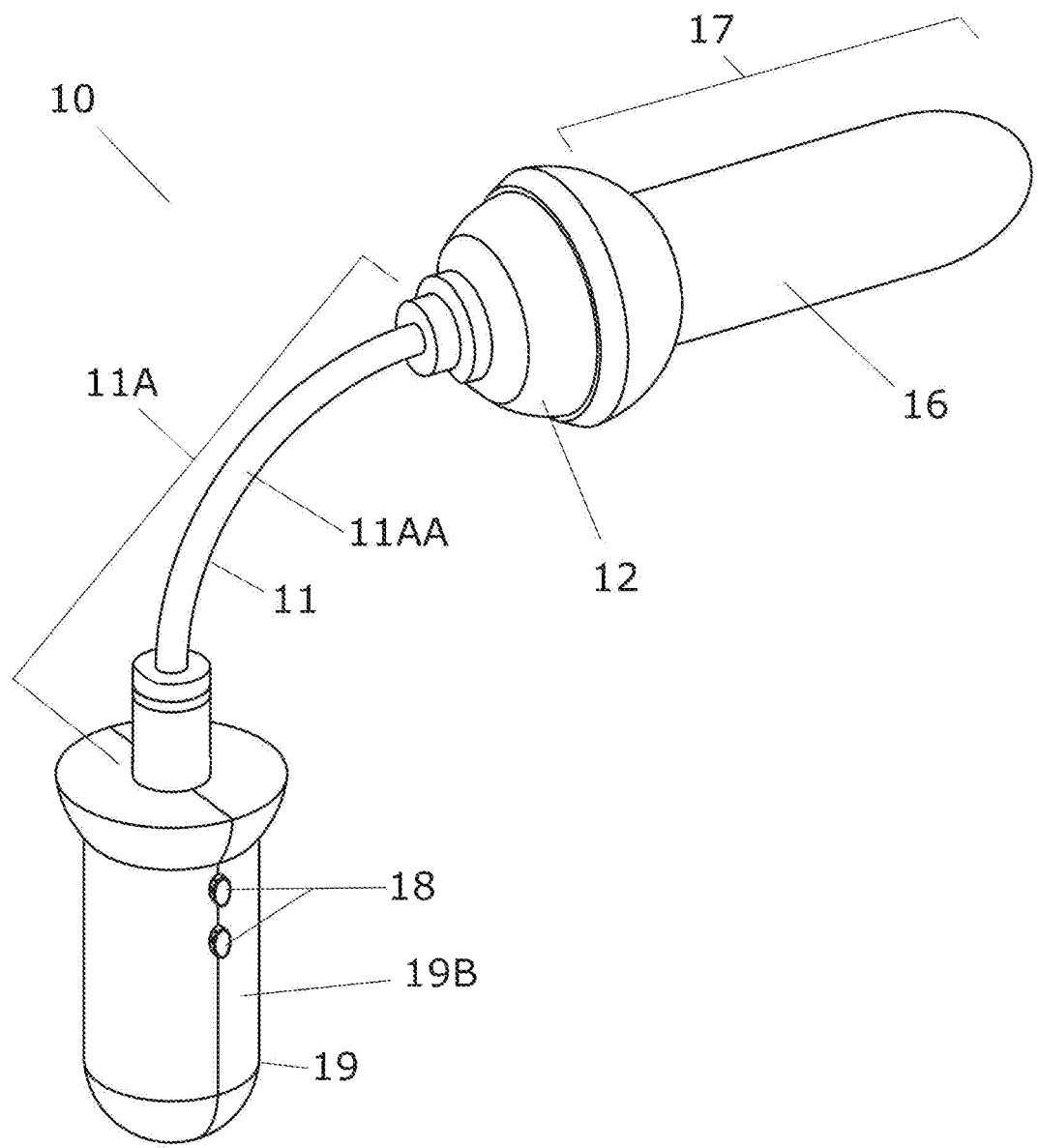
FIG. 11 illustrates a perspective view of the device 10 with the shaft 17 at its minimum girth size according to an embodiment of the device 10.

In another embodiment, as illustrated in FIG. 10 and FIG. 11, the device 10 may comprise at least one enclosed electric motor 19 and at least one electronic part 18 (enclosed electric motor 19 described in Enclosed electric motor section). In the embodiment illustrated in FIG. 10, the motor housing 19B of the enclosed electric motor 19 is connected to the housing 12, the motor shaft of the motor having a motor shaft 19A of the enclosed electric motor 19 is connected to the first end 11A of the controller 11, such that when the motor shaft of the motor having a motor shaft 19A is rotated clockwise or counter-clockwise by the user via an electronic part 18, the first end 11A and the second end 11B of the controller 11, rotate following the rotation of the motor shaft of the motor having a motor shaft 19A of the enclosed electric motor 19. The second end 11B of the controller 11 is connected to threaded shaft 13, such that when the second end 11B of the controller 11 rotates, the threaded shaft 13 rotates following the rotation of the second end 11B of the controller 11. In the embodiment illustrated in FIG. 11, the enclosed electric motor 19 is connected to the first end 11A configured with a flexible shaft 11AA of the controller 11, such that when the motor shaft of the motor having a motor shaft 19A of the enclosed electric motor 19 is rotated clockwise or counter-clockwise by the user via an electronic part 18, the first end 11A configured with a flexible shaft 11AA, and the second end 11B of the controller 11 rotate following the rotation of the motor shaft of the motor having a motor shaft 19A of the enclosed electric motor 19. The second end 11B of the controller 11 is connected to threaded shaft 13, such that when the second end 11B of the controller 11 rotates, the threaded shaft 13 rotates following the rotation of the second end 11B of the controller 11.

Figure 12A:
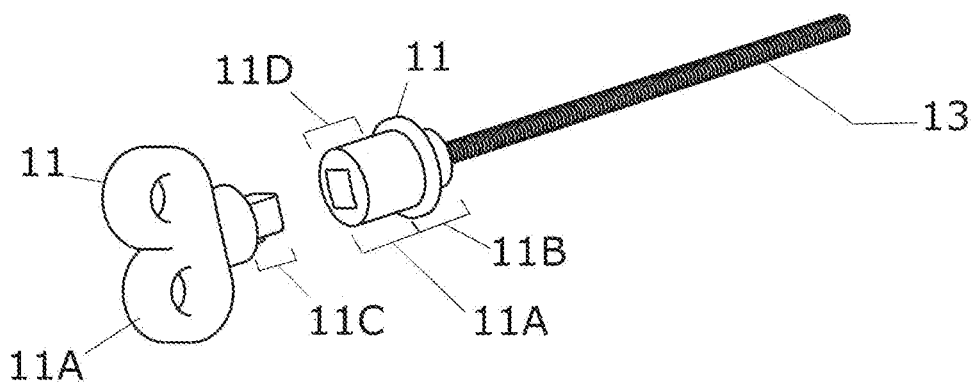
FIG. 12A illustrates a perspective view of the controller 11 connected to the threaded shaft 13 according to an embodiment of the device 10.
Figure 12B:
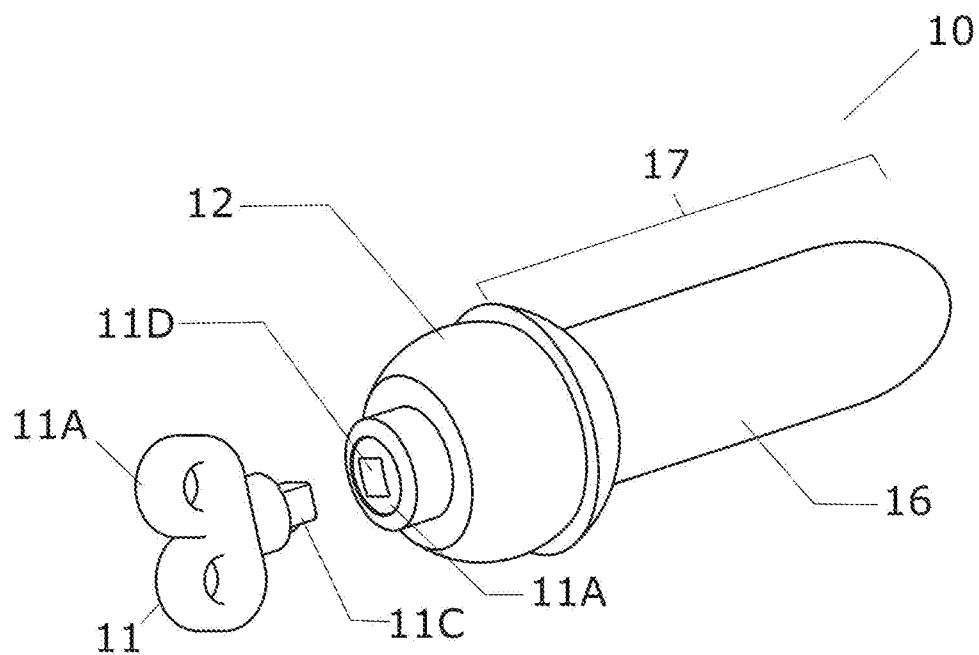
FIG. 12B illustrates a perspective view of the device 10 with the shaft 17 at its minimum girth size according to an embodiment of the device 10.
Figure 13A:
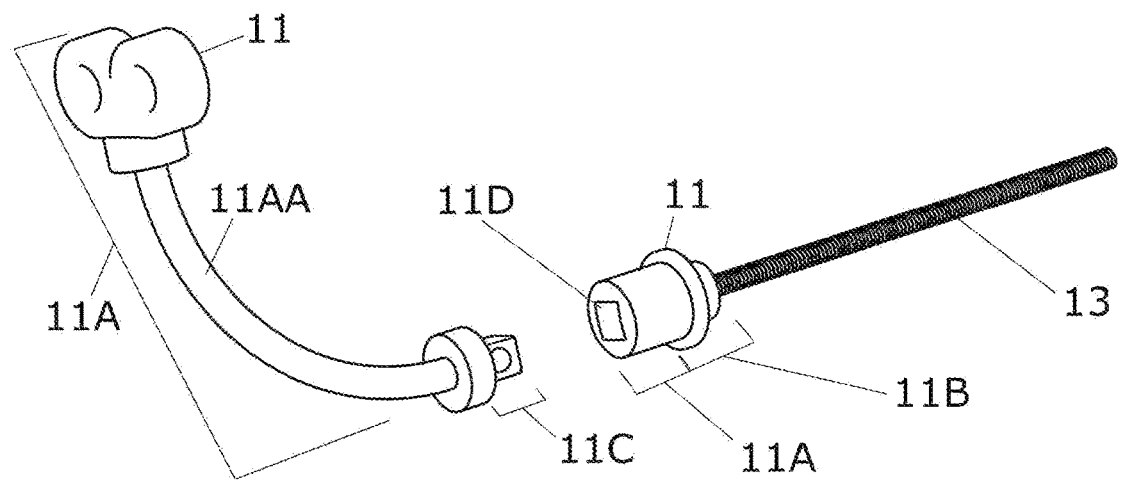
FIG. 13A illustrates a perspective view of the controller 11 connected to the threaded shaft 13 according to an embodiment of the device 10.
Figure 13B:
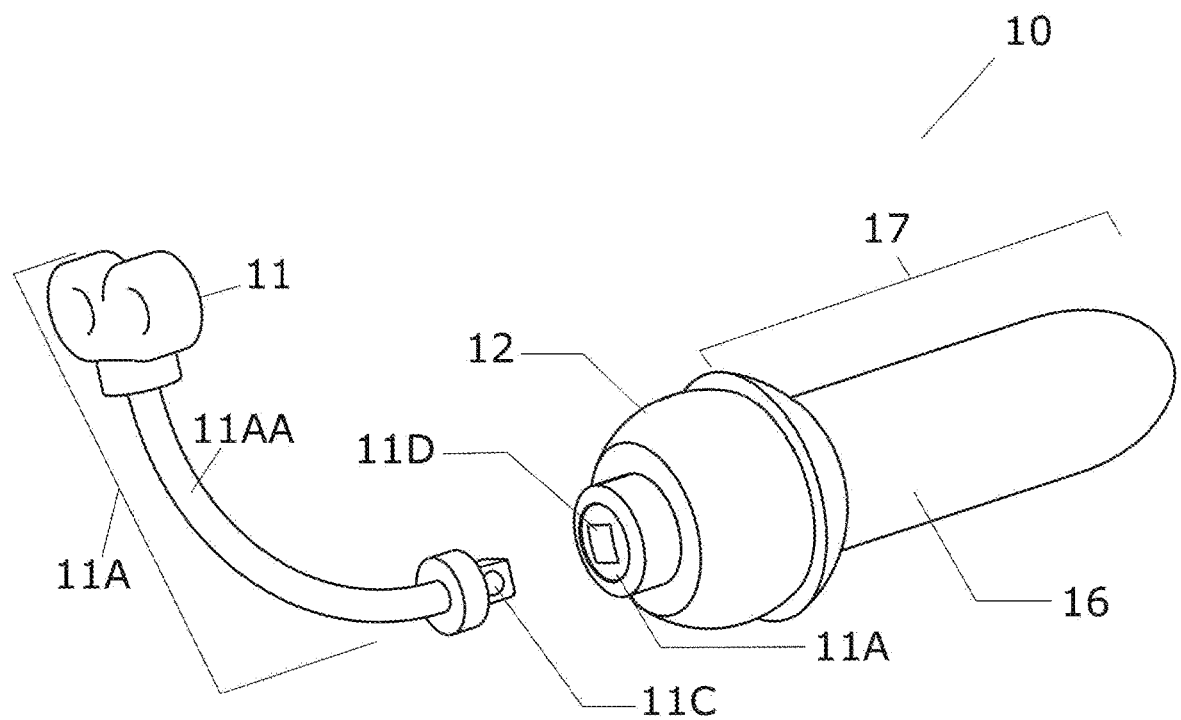
FIG. 13B illustrates a perspective view of the device 10 with the shaft 17 at its minimum girth size according to an embodiment of the device 10.
Figure 14A:
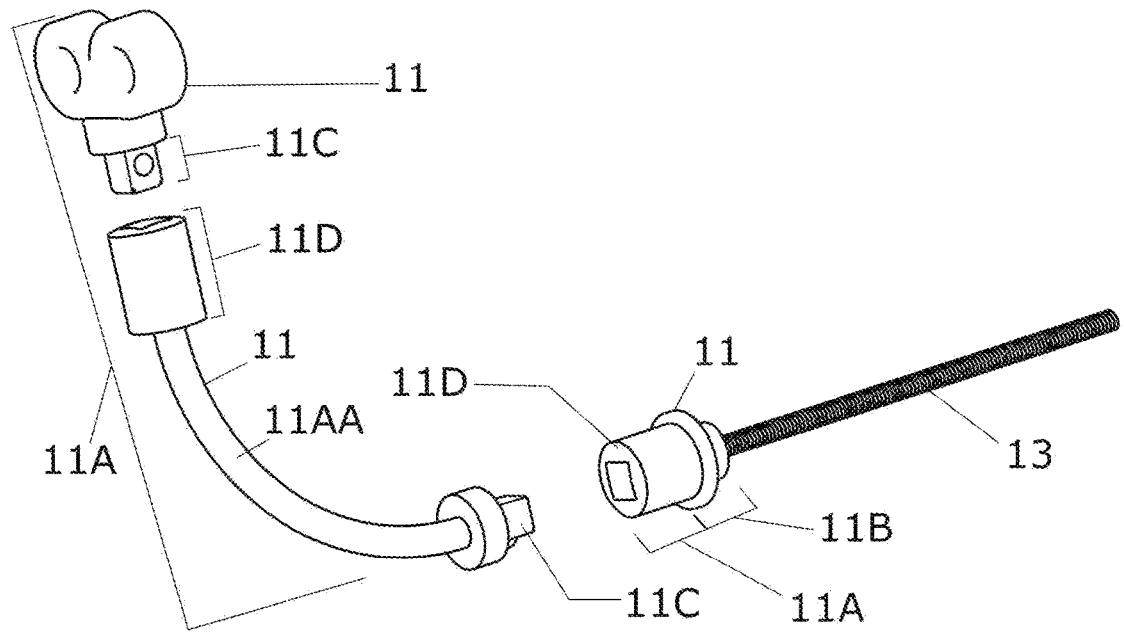
FIG. 14A illustrates a perspective view of the controller 11 connected to the threaded shaft 13 according to an embodiment of the device 10.
Figure 14B:
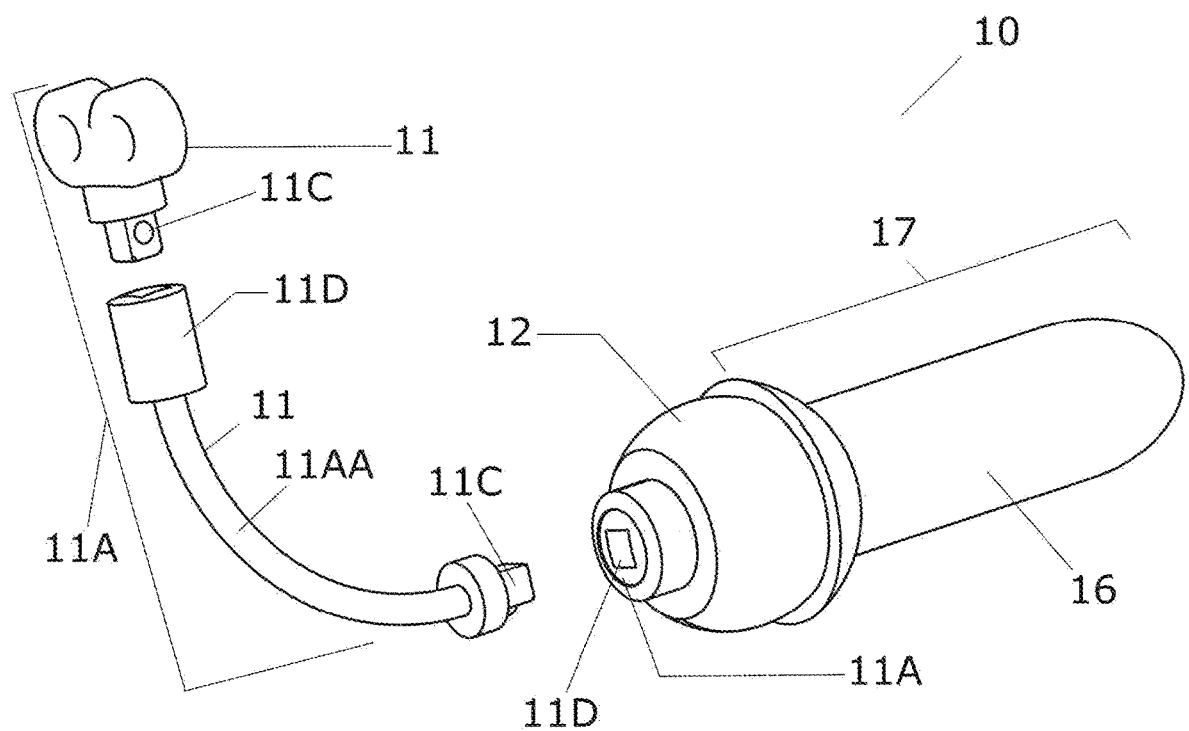
FIG. 14B illustrates a perspective view of the device 10 with the shaft 17 at its minimum girth size according to an embodiment of the device 10.
Figure 15A:
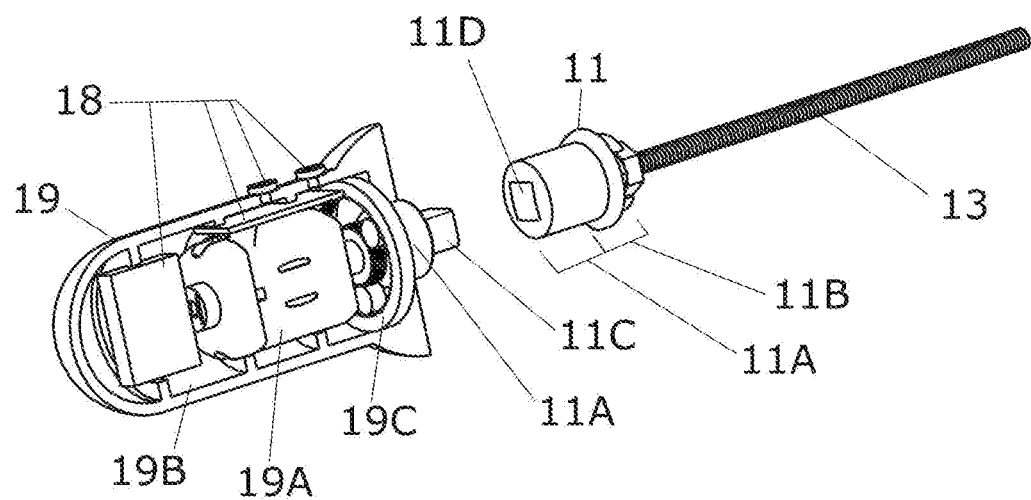
FIG. 15A illustrates a perspective view of the enclosed electric motor 19 (only one part of the motor housing 19B is illustrated) connected to the controller 11, which is connected to the threaded shaft 13 according to an embodiment of the device 10.
Figure 15B:
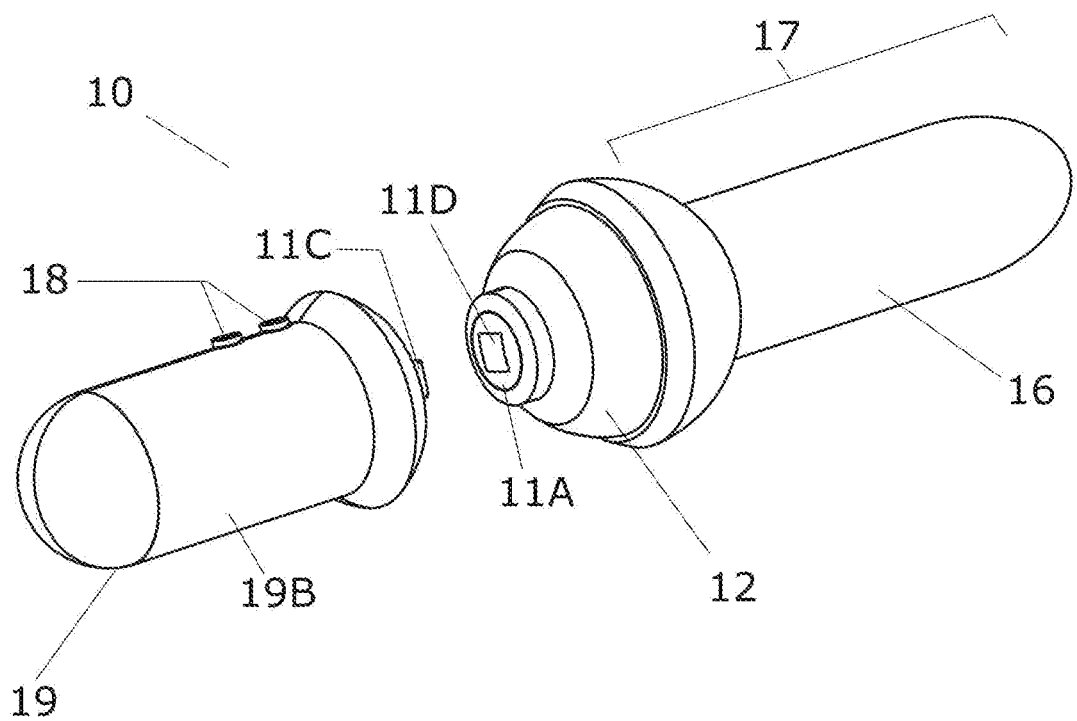
FIG. 15B illustrates a perspective view of the device 10 with the shaft 17 at its minimum girth size according to an embodiment of the device 10.
Figure 16:
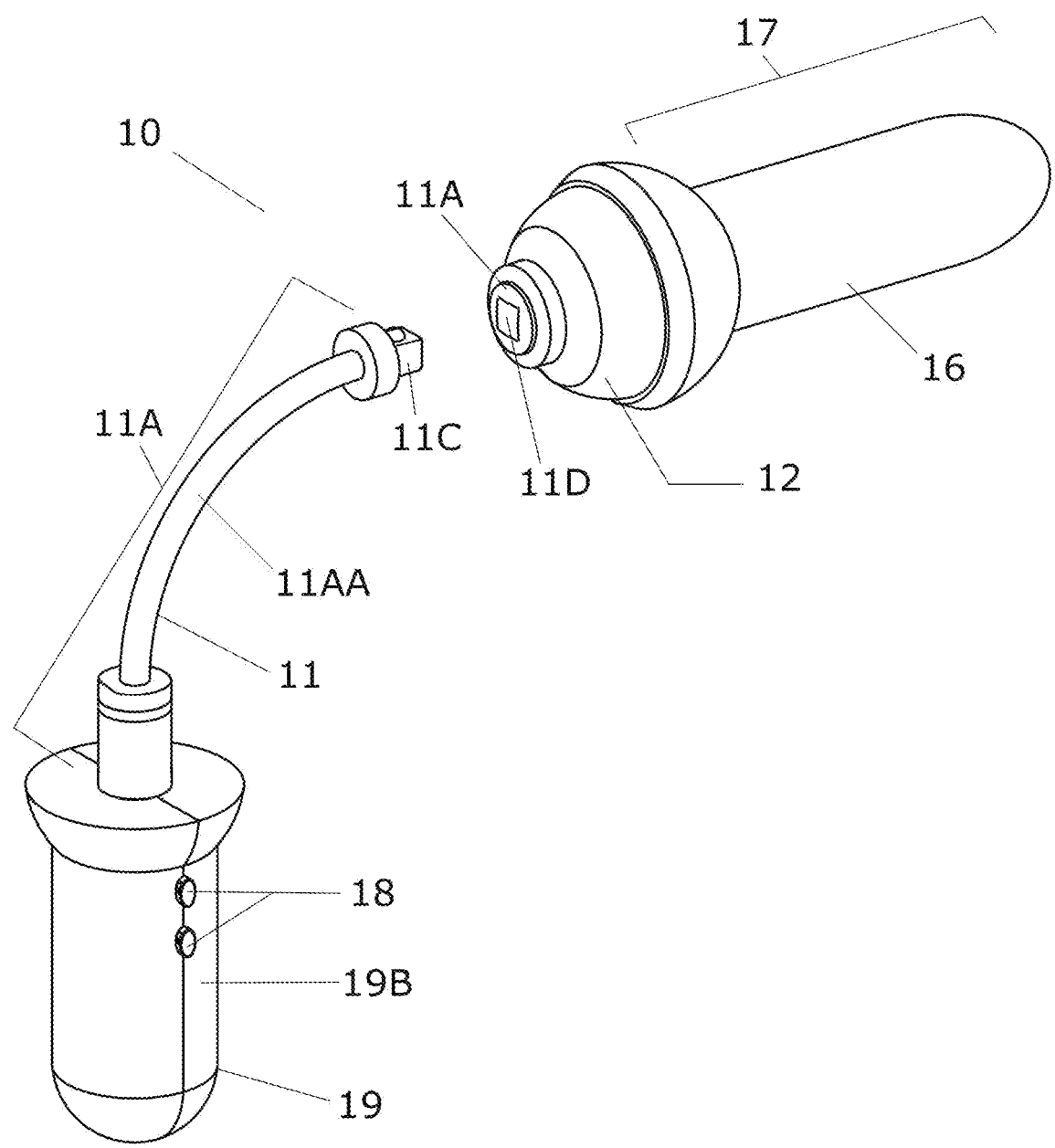
FIG. 16 illustrates a perspective view of the device 10 with the shaft 17 at its minimum girth size according to an embodiment of the device 10.
Figure 17:
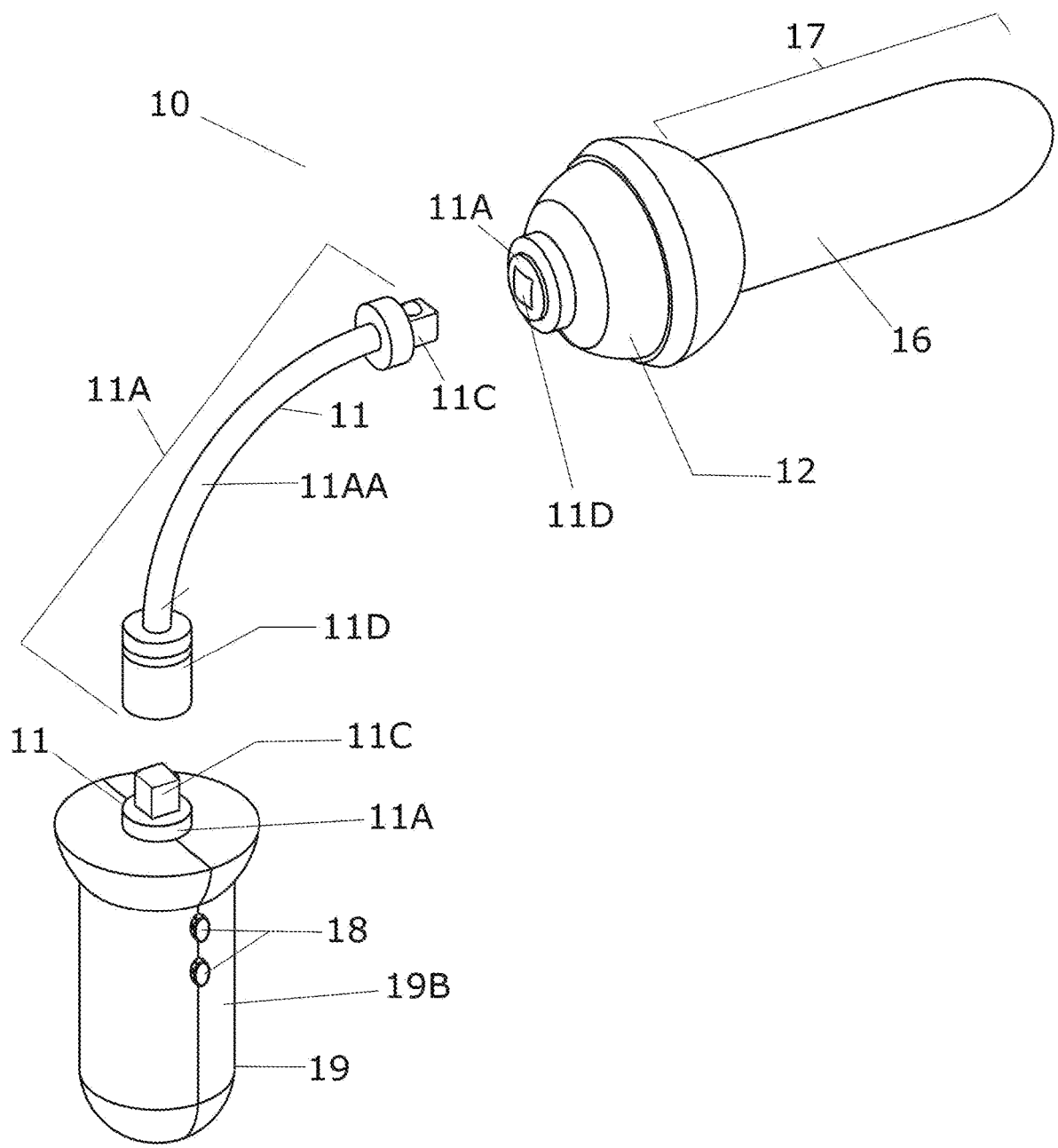
FIG. 17 illustrates a perspective view of the device 10 with the shaft 17 at its minimum girth size according to an embodiment of the device 10.
Figure 19B:
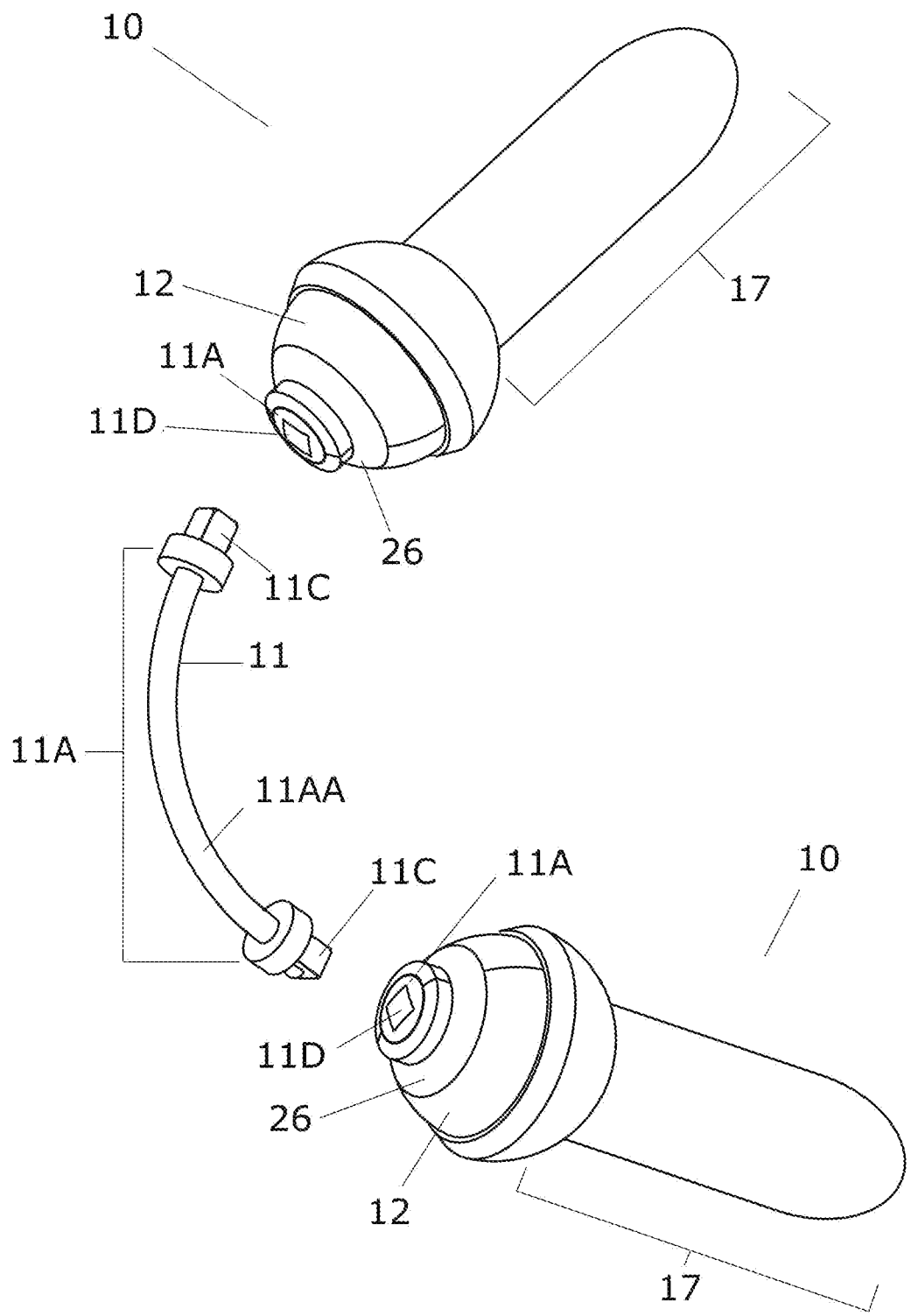
FIG. 19B illustrates a perspective view of two devices 10 with the shaft 17 at its minimum girth size according to an embodiment of the device 10.

In another embodiment as illustrated from FIG. 12 to FIG. 18 and in FIG. 19B, the first end 11A of the controller 11 may comprise at least one male connection 11C and at least one female connection 11D. Preferably, the female connection 11D is configured such as but not limited to: a socket wrench type, a keyhole type or a screw drive type such as but not limited to: slotted type, cruciform type, polygon type, hexablobular type, three-pointed type, clutch, one-way type, bristol type, quadrex type, pentalobe type and/or spanner head screw drive type. Preferably, the male connection 11C and the female connection 11D are made of such as but not limited to: plastic, metal, and/or ferromagnetic material. Attention being called to the fact that, when the male connection 11C is made of metal and the female connection 11D is made of a ferromagnetic material or the male connection 11C is made of a ferromagnetic material and the female connection 11D is made of metal, it may facilitate by magnetic attraction the connection between the male connection 11O and the female connection 11D. The male connection 11O is configured to removably fit into the female connection 11D, which means that the male connection 11O may be repeatedly: connected to the female connection 11D, then removed from the female connection 11D, and then connected again to the female connection 11D, and such that when the male connection 11O is connected to the female connection 11D and when the male connection 11O rotates clockwise or counter-clockwise, the female connection 11D rotates following the rotation of the male connection 11O. As illustrated in FIG. 12, the first end 11A is connected to the male connection 11O and to the female connection 11D, such that when the male connection 11C is connected to the female connection 11D, and when the first end 11A is rotated clockwise or counter-clockwise, the second end 11B rotates following the rotation of the first end 11A. The second end 11B of the controller 11 is connected to the threaded shaft 13, such that when the second end 11B of the controller 11 rotates, the threaded shaft 13 rotates following the rotation of the second end 11B of the controller 11. As illustrated in FIG. 13, the first end 11A configured with the flexible shaft 11AA is connected to the male connection 11O and to the female connection 11D, such that when the male connection 11C is connected to the female connection 11D, and when the first end 11A configured with the flexible shaft 11AA is rotated clockwise or counter-clockwise by the user, the second end 11B rotates following the rotation of the first end 11A configured with the flexible shaft 11AA. The second end 11B of the controller 11 is connected to threaded shaft 13, such that when the second end 11B of the controller 11 rotates, the threaded shaft 13 rotates following the rotation of the second end 11B of the controller 11. As illustrated in FIG. 14, the first end 11A configured with the flexible shaft 11AA may comprise two male connections 11C and two female connections 11D, such that when a first male connection 11C is connected to a first female connection 11D, and a second male connection 11C is connected to a second female connection 11D, and when the first end 11A configured with the flexible shaft 11AA is rotated clockwise or counter-clockwise by the user, the second end 11B rotates following the rotation of the first end 11A configured with the flexible shaft 11AA. The second end 11B of the controller 11 is connected to threaded shaft 13, such that when the second end 11B of the controller 11 rotates, the threaded shaft 13 rotates following the rotation of the second end 11B of the controller 11. As illustrated in FIG. 15, in the embodiment of the device 10 comprising an enclosed electric motor 19, the motor shaft of the motor having a motor shaft 19A of the enclosed electric motor 19 is connected to the first end 11A of the controller 11, the first end 11A is connected to the male connection 11C and the female connection 11D, such that when the male connection 11C is connected to the female connection 11D, and when the motor shaft of the motor having a motor shaft 19A of the enclosed electric motor 19 is rotated by the user via an electronic part 18, the first end 11A and the second end 11B of the controller 11 rotate following the rotation of the motor shaft of the motor having a motor shaft 19A of the enclosed electric motor 19. The second end 11B of the controller 11 is connected to threaded shaft 13, such that when the second end 11B of the controller 11 rotates, the threaded shaft 13 rotates following the rotation of the second end 11B of the controller 11. As illustrated in FIG. 16, in the embodiment of the device 10 comprising an enclosed electric motor 19, the motor shaft of the motor having a motor shaft 19A of the enclosed electric motor 19 is connected to the first end 11A configured with the flexible shaft 11AA of the controller 11, the first end 11A configured with the flexible shaft 11AA is connected to the male connection 11C and the female connection 11D, such that when the male connection 11C is connected to the female connection 11D, and when the motor shaft of the motor having a motor shaft 19A (not illustrated in FIG. 16) of the enclosed electric motor 19 is rotated clockwise or counter-clockwise by the user via an electronic part 18, the first end 11A configured with the flexible shaft 11AA and the second end 11B of the controller 11 rotate following the rotation of the motor shaft of the motor having a motor shaft 19A (not illustrated in FIG. 16) of the enclosed electric motor 19. The second end 11B of the controller 11 is connected to threaded shaft 13, such that when the second end 11B of the controller 11 rotates, the threaded shaft 13 rotates following the rotation of the second end 11B of the controller 11. As illustrated in FIG. 17, in the embodiment of the device 10 comprising an enclosed electric motor 19, the first end 11A configured with the flexible shaft 11AA may comprise two male connections 11C and two female connections 11D, such that when a first male connection 11C is connected to a first female connection 11D, and a second male connection 11C is connected to a second other female connection 11D, and when the motor shaft of the motor having a motor shaft 19A (not illustrated in FIG. 17) of the enclosed electric motor 19 is rotated clockwise or counter-clockwise by the user via an electronic part 18, the first end 11A configured with the flexible shaft 11AA and the second end 11B of the controller 11 rotate following the rotation of the motor shaft of the motor having a motor shaft 19A (not illustrated in FIG. 17) of the enclosed electric motor 19. The second end 11B of the controller 11 is connected to threaded shaft 13, such that when the second end 11B of the controller 11 rotates, the threaded shaft 13 rotates following the rotation of the second end 11B of the controller 11. As illustrated in FIG. 19B, the first end 11A configured with the flexible shaft 11AA may comprise two male connections 11C and one female connections 11D, such that when a first male connection 11C is connected to the female connection 11D, and the second male connection 11C is connected to a female connection 11D of another device 10, (other device 10 in which the part of its first end 11A having one male connection 11C of its controller 11 is not used and removed; other device 10 preferably comprising a threaded shaft 13 left-handed threaded; threaded shaft 13 left-handed threaded described in Threaded shaft section), and when the first end 11A configured with the flexible shaft 11AA of the device 10 is rotated clockwise or counter-clockwise by the user, the second end 11B of the device 10 and the second end 11B of the other device 10 rotate. This embodiment provides others features that enhance the body orifice dilation and stretch procedure for the user during the utilization of several devices 10.

Figure 20A:
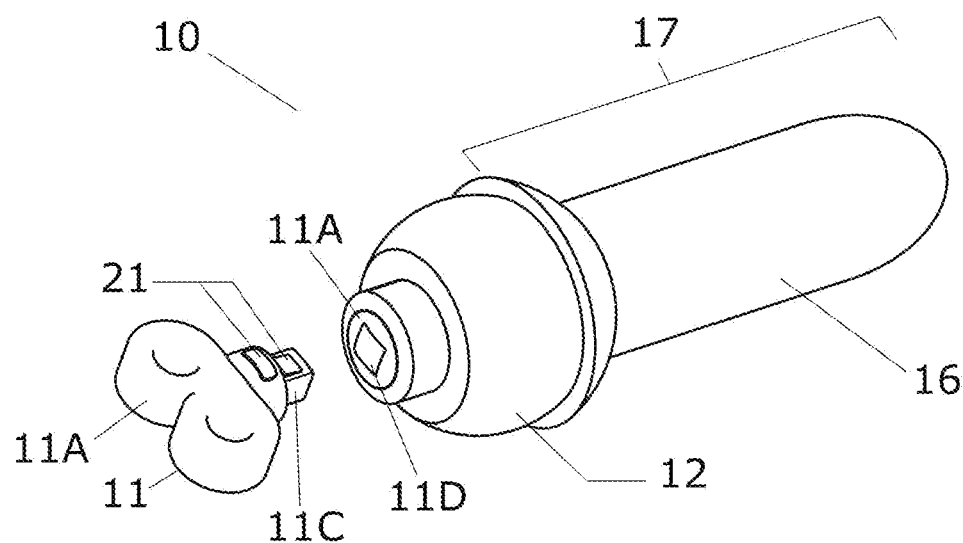
FIG. 20A illustrates a perspective view of the device 10 with the shaft 17 at its minimum girth size according to an embodiment of the device 10.
Figures 20B, 20C:
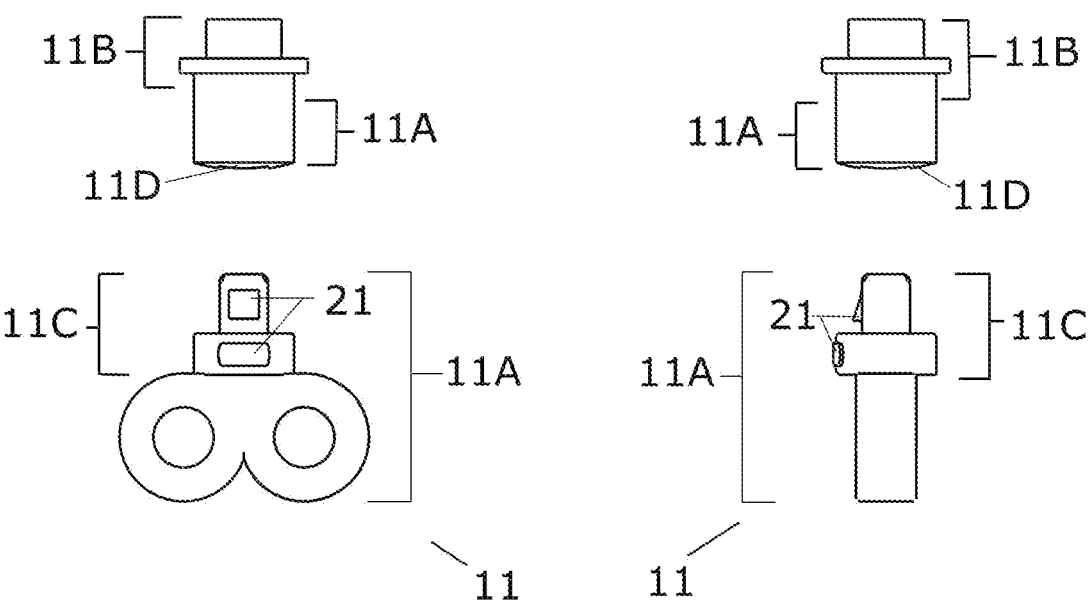
FIG. 20B illustrates a front view of the controller 11 according to an embodiment of the device 10.
FIG. 20C illustrates a side view of the controller 11 according to an embodiment of the device 10.

In another embodiment as illustrated in FIG. 20, the first end 11A of the controller 11 having at least one male connection 11C and at least one female connection 11D may comprise at least one locking system 21. The locking system 21 removably secures the male connection 11C to the female connection 11D, which means that the male connection 11C may be repeatedly: secured to the female connection 11D, then removed from the female connection 11D, and then secured again to the female connection 11D. The locking system 21 is preferably an easy release system such as but not limited to: a spring-loaded system. This embodiment enhances the utilization of the device 10 for the user to prevent undesired disconnection of the controller 11 during the utilization of the device 10. The user operates the locking system 21 via the controller 11.

In another embodiment (not illustrated), the controller 11 or only the second end 11B of the controller 11 may be manufactured with the threaded shaft 13 as one part. This embodiment is an alternative for manufacturing optimization of the device 10.

Figure 21A:
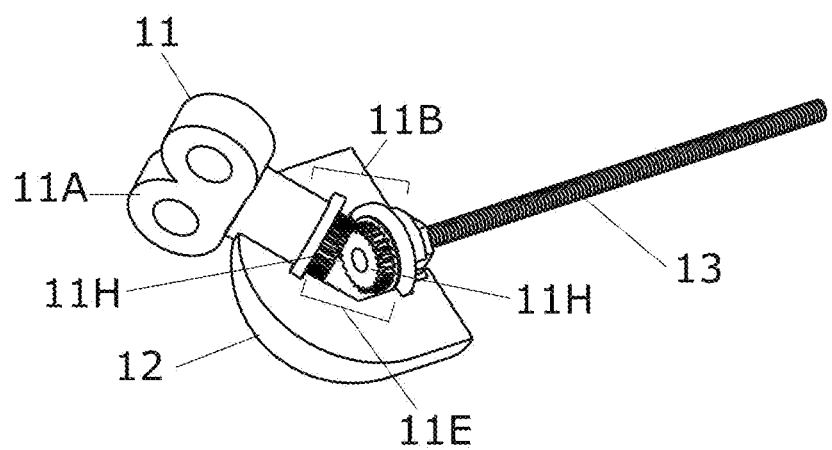
FIG. 21A illustrates a perspective view of the controller 11 connected to the threaded shaft 13 inside the housing 12 (only one part of the housing 12 illustrated) according to an embodiment of the device 10.
Figure 21B:
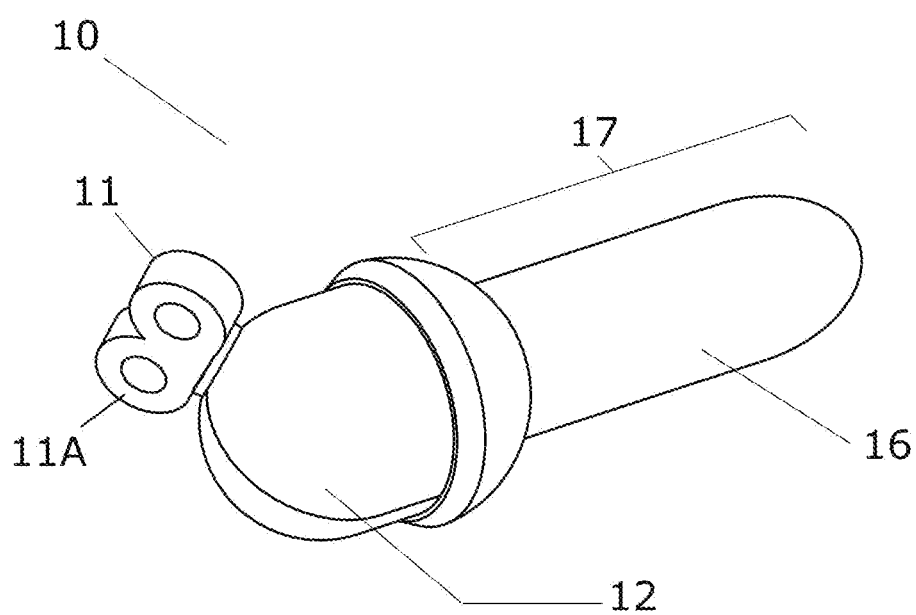
FIG. 21B illustrates a perspective view of the device 10 with the shaft 17 at its minimum girth size according to an embodiment of the device 10.

In another embodiment, as illustrated in FIG. 21, the controller 11 may comprise at least one controller angular transmission 11E. The controller angular transmission 11E may be configured with a plurality of gears 11H (plurality of gears 11H described in Plurality of gears section) as illustrated in FIG. 21, or gearless (not illustrated). Preferably, the controller angular transmission 11E is configured to create an angle greater than or equal to 0.1° with the longitudinal axis of the threaded shaft 13, in the controller 11. Preferably, the controller 11 having at least one controller angular transmission 11E is connected to the threaded shaft 13, such that when the controller 11 having at least one controller angular transmission 11E rotates, the threaded shaft 13 rotates following the rotation of the second end 11B. The controller 11 having at least one controller angular transmission 11E reduces the distance to reach the controller 11 for the user and therefore facilitates the utilization of the device 10.

Figure 59A:
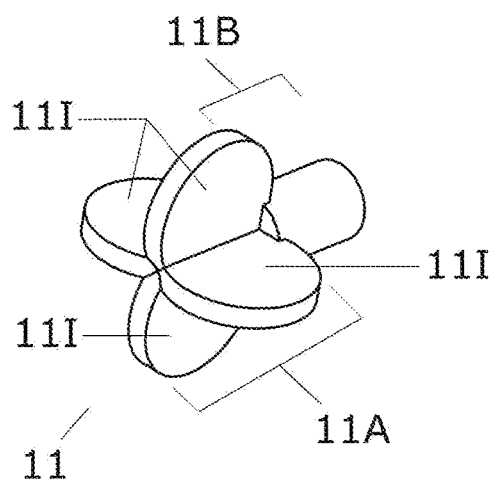
FIG. 59A illustrates a perspective view of the controller 11 according to an embodiment of the device 10.

In another embodiment, as illustrated in FIG. 59A, the controller 11 may comprise at least one handy area 11I, a handy area is an area on the first end 11A of the controller 11 large enough for the user to apply a part of at least one of its fingers and/or its hands to rotate with ease the controller 11 clockwise and counter-clockwise.

Threaded Shaft

In a preferred embodiment, the device 10 comprises one threaded shaft 13. The threaded shaft 13, as illustrated in FIG. 5B, has a first end 13A, a middle section 13B, a second end 13C, and a longitudinal axis. The direction of orientation going from the first end 13A to the second end 13C or from the second end 13C to the first end 13A of the threaded shaft 13 is referred hereinafter to as "the longitudinal axis of the threaded shaft". The first end 13A of the threaded shaft 13 is connected to the second end 11B of the controller 11 (as illustrated in FIG. 5C), such that when the second end 11B rotates clockwise or counter-clockwise, the threaded shaft 13 rotates following the rotation of the second end 11B of the controller 11. Preferably, the threaded shaft 13 is a threaded rod fastener configured with a length greater than 1 inch, a major diameter greater than 0.0730 inch, and with less than or equal to 160 threads per inch. The quantity of threads per inch of the threaded shaft 13 defines partially the specific characteristics of the adjustment of the device 10, and defines the increments of increase and decrease of the shaft girth size when the controller 11 is rotated by the user. In a preferred embodiment the increment of the shaft girth is less than 0.03937 inch. Preferably, the threaded shaft 13 is right-handed threaded, which means made of right-handed threads, however, the threaded shaft 13 may be left-handed threaded, which means made of left-handed threads, and therefore reversing the direction of rotation of the threaded shaft 13 to perform the adjustment of the device 10. Preferably, the threaded shaft 13 is made of such as but not limited to: metal or plastic. The threaded shaft 13 when made of metal, may be magnetized to increase the blood flow, relaxes muscles and ligaments of the body orifice region and therefore enhance the dilation and stretch of the body orifice during the utilization of the device 10.

In another embodiment, as illustrated in FIG. 22A, the threaded shaft 13 may comprise at least one maximum translation stopper 13E preferably made of a rigid material such as but not limited to: metal and/or plastic, however, the maximum translation stopper 13E may be made of a semi-rigid material such as but not limited to: plastic, silicone and/or rubber, and the maximum translation stopper 13E may be made in combination with a soft material such as but not limited to: silicone, and/or rubber, to absorb the impact with the module 14 (or plurality of modules 14). The maximum translation stopper 13E may be such as but not limited to: a nut fastener, and/or a washer fastener. Preferably, the maximum translation stopper 13E is secured to the threaded shaft 13. The maximum translation stopper 13E is configured on the threaded shaft 13 to stop the module 14 from traveling along the threaded shaft 13, and therefore to stop the rotation of the controller 11 when the adjustment reaches the maximum girth size of the shaft 17 offered by the device 10. In this embodiment, the housing 12 and the shaft member 15 (not illustrated in this embodiment) are configured to receive the maximum translation stopper 13E. The maximum translation stopper 13E reduces friction and handling stress on the device 10 during the utilization by the user.

In another embodiment as illustrated in FIG. 22B, the threaded shaft 13 may comprise at least one minimum translation stopper 13F preferably made of a rigid material such as but not limited to: metal and/or plastic, however, the minimum translation stopper 13F may be made of a semi-rigid material such as but not limited to: plastic, silicone and/or rubber, and the minimum translation stopper 13F may be made in combination with a soft material such as but not limited to: silicone, and/or rubber, to absorb the impact with the module 14 (or plurality of modules 14). The minimum translation stopper 13F may be such as but not limited to: a nut fastener, and/or a washer fastener. Preferably, the minimum translation stopper 13F is secured to the threaded shaft 13. Preferably, the minimum translation stopper 13F is configured on the threaded shaft 13 to stop the module 14 from traveling along the threaded shaft 13, and therefore to stop the rotation of the controller 11 when the adjustment reaches the minimum girth size of the shaft 17 offered by the device 10. In this embodiment, the housing 12 and the shaft member 15 (not illustrated in this embodiment) are configured to receive the minimum translation stopper 13F. The minimum translation stopper 13F reduces friction and handling stress on the device 10 during the utilization by the user. The minimum translation stopper 13F may be configured such as but not limited to: a cap nut fastener (illustrated in FIG. 22B), to protect the sheath 16 from the second end 13C.

Figure 22C:
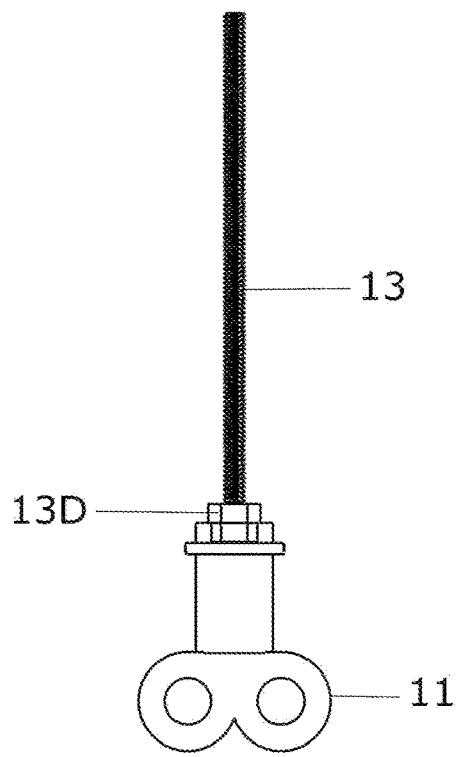
FIG. 22C illustrates the controller 11 connected to the threaded shaft 13 according to an embodiment of the device 10.

In another embodiment, as illustrated in FIG. 22C, the threaded shaft 13 may comprise at least one controller-connector 13D made of a rigid material such as but not limited to: metal and/or plastic. The controller-connector 13D may be such as but not limited to: a nut fastener (as illustrated in FIG. 22C) and/or a wing nut fastener (not illustrated). The controller-connector 13D is configured at the first end 13A of the threaded shaft 13 and connects the second end 11B to the controller 11 to the threaded shaft 13. Preferably, the controller-connector 13D is secured to the threaded shaft 13. The controller-connector 13D reinforces the connection between the controller 11 and the threaded shaft 13, reduces friction and handling stress on the device 10 during the utilization. FIG. 22C illustrates a front view of the controller 11 connected to the threaded shaft 13 via the controller-connector 13D in this this embodiment.

Figure 23A:
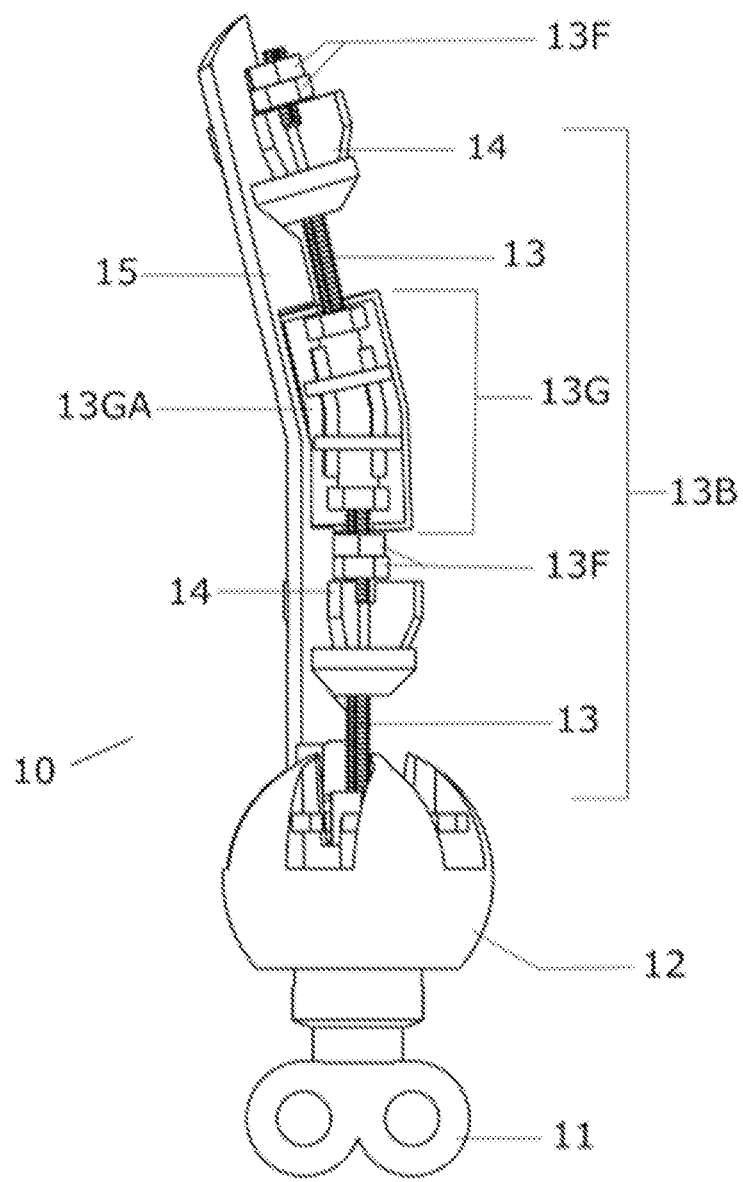
FIG. 23A illustrates a front view of the device 10 with the shaft 17 at its minimum girth size according to an embodiment of the device 10 (sheath 16 not illustrated, only one shaft member 15 illustrated, and only one part of the threaded shaft angular transmission housing 13GA illustrated).
Figure 23B:
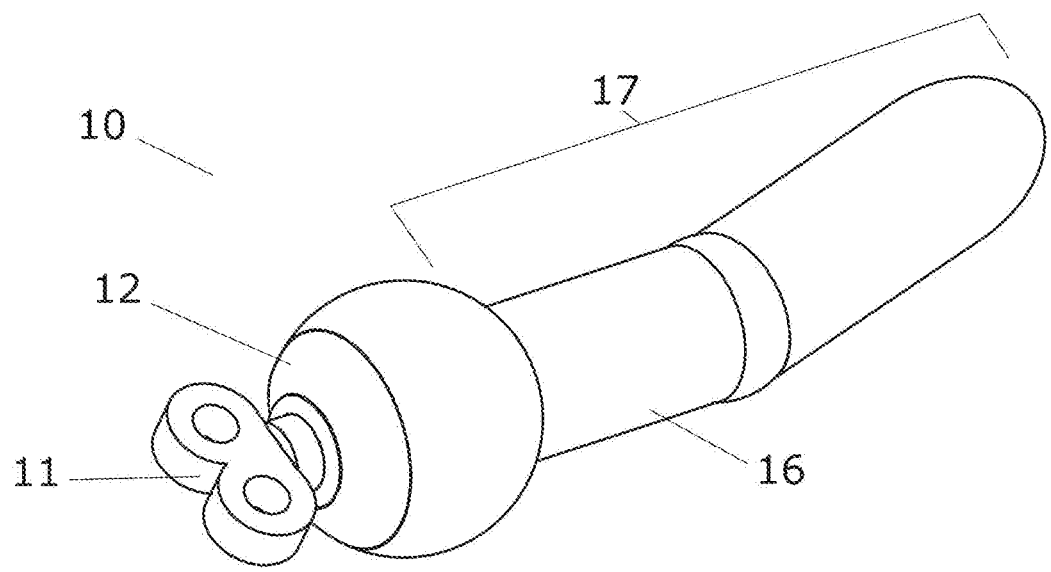
FIG. 23B illustrates a perspective view of the device 10 with the shaft 17 at its minimum girth size according to an embodiment of the device 10.
Figure 23C:
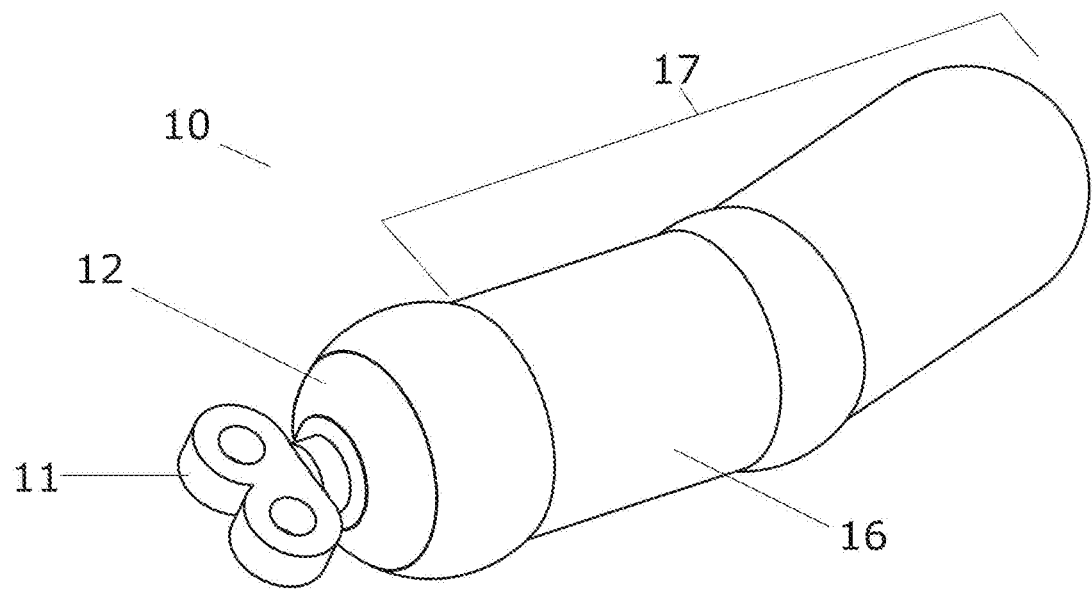
FIG. 23C illustrates a perspective view of the device 10 with the shaft 17 at its maximum girth size according to an embodiment of the device 10.

In another embodiment, the threaded shaft 13 may comprise at least one threaded shaft angular transmission 13G having a threaded shaft angular transmission housing 13GA. The threaded shaft angular transmission 13G may be configured with a plurality of gears 11H (not illustrated in this embodiment), or gearless as illustrated in FIG. 23. Preferably, the threaded shaft angular transmission 13G is configured to create an angle greater than or equal to 0.1° with the longitudinal axis of the threaded shaft 13, in the threaded shaft 13. The angular transmission 13G when located at the first end 13A of the threaded shaft 13 (not illustrated in this embodiment) reduces the distance to reach the controller 11 for the user and therefore facilitates the utilization of the device 10 and when the angular transmission 13G is located at the middle section 13B (as illustrated in FIG. 23), and/or the second end 13C (not illustrated in this embodiment) of the threaded shaft 13, provides other features that enhance the body orifice dilation and stretch procedure for the user such as but not limited to: prostate stimulation. In this embodiment, the shaft member 15 and the sheath 16 are configured to receive the threaded shaft 13 having at least one angular transmission 13G. The threaded shaft angular transmission housing 13GA may comprise at least one angular transmission connector (not illustrated) that slidably fit inside a module connector groove 15D to prevent undesired translation and/or rotation of the threaded shaft 13 having at least one angular transmission 13G. FIG. 23A illustrates a front view of the device 10 with the shaft 17 at its minimum girth size in this embodiment (sheath 16 not illustrated, only one shaft member 15 illustrated, and only one part of the threaded shaft angular transmission housing 13GA illustrated). FIG. 23B illustrates a perspective view of the device 10 with the shaft 17 at its minimum girth size in this embodiment. FIG. 23C illustrates a perspective view of the device 10 with the shaft 17 at its maximum girth size in this embodiment.

Housing

In a preferred embodiment, the device 10 comprises a housing 12. In a preferred embodiment, the housing 12 has a controller first end 12A, a shaft member second end 12B having a plurality of shaft member grooves 12BA and a plurality of shaft member protrusions 12BB, and a non-threaded canal 12C, as illustrated in FIG. 24, FIG. 25 and FIG. 26. The housing 12 encloses the second end 11B of the controller 11 and the first end 13A of the threaded shaft 13. However, the housing 12 may enclose partially or totally the first end 11A of the controller 11. Preferably, the non-threaded canal 12C is a non-threaded canal. The non-threaded canal 12C receives the first end 13A of the threaded shaft 13, and the controller first end 12A receives the second end 11B of the controller 11 connected to the first end 13A, such that when the housing 12 encloses the second end 11B and the first end 13A, the second end 11B and the first end 13A can only rotate clockwise and counter-clockwise around the longitudinal axis of the threaded shaft 13. The shaft member second end 12B via the plurality of shaft member grooves 12BA and the plurality of shaft member protrusions 12BB of the housing 12 slidably receive each first end 15A having at least one housing groove 15AA of the plurality of shaft members 15 (shaft member 15 illustrated in FIG. 31) such that when the user performs the adjustment of the device 10, each shaft member 15 of the plurality of shaft members 15 can only travel perpendicularly to the longitudinal axis of the threaded shaft 13. Each shaft member grooves 12BA via at least one shaft member protrusions 12BB per shaft member grooves 12BA maintains the longitudinal axis of the shaft member 15 of one shaft member 15 approximatively or exactly parallel with the longitudinal axis of the threaded shaft 13, when the girth size of the shaft 17 is at its minimum girth size, maximum girth size, and when the user performs the adjustment of the device 10. The shaft member protrusion 12BB may be a fastener such as but not limited to: a screw, a nail, or a pin, secured to the housing 12. At least one shaft member protrusion 12BB of the housing 12 may be configured as a cantilever snap-fit (illustrated in FIG. 27C and FIG. 27D). In that case, the first end 15A of the shaft member 15 is configured to receive the shaft member protrusion 12BB of the housing 12 configured as a cantilever snap-fit (illustrated in FIG. 32C). Each shaft member groove 12BA receives its corresponding shaft member 15, and each shaft member protrusion 12BB receives its corresponding housing groove 15AA to prevent undesired translation and/or rotation of the corresponding shaft member 15 during the utilization of the device 10.

Preferably, the longitudinal axis of each of the plurality of shaft member protrusions 12BB is approximately or exactly perpendicular to the longitudinal axis of the threaded shaft 13, however, to reduce friction and handling stress on the plurality of shaft members 15 during the utilization of the device 10, the longitudinal axis of each of the plurality of shaft member protrusions 12BB may be configured to make an angle greater or lower than 90° with the longitudinal axis of the threaded shaft 13, as illustrated in FIG. 29D. In that case the housing groove 15AA of the shaft member 15 is configured to receive the shaft member protrusion 12BB configured with a longitudinal axis making an angle greater or lower than 90° with the longitudinal axis of the threaded shaft 13.

To reduce friction and handling stress on the plurality of shaft members 15 during the utilization of the device 10, the housing 12 may be configured with a plurality of friction reducers 34. The friction reducer 34 is such as but not limited to: a wheel and its axle held in a cavity (as illustrated in FIG. 29C and FIG. 29D) and/or a ball held in a cavity (not illustrated). The friction reducer 34 is made of such as but not limited to: plastic and/or metal.

To reduce friction and handling stress on the controller 11 and the plurality of shaft members 15 during the utilization of the device 10, the housing 12 may be lubricated.

At least one shaft member groove 12BA may be configured to slidably receive (not illustrated) the closest apex (or the closest flat base) of the conical section with a slant height 14A of the closest module 14 of the housing 12, so as to prevent undesired rotations of the module 14 around the longitudinal axis of the threaded shaft 13.

Figure 24A:
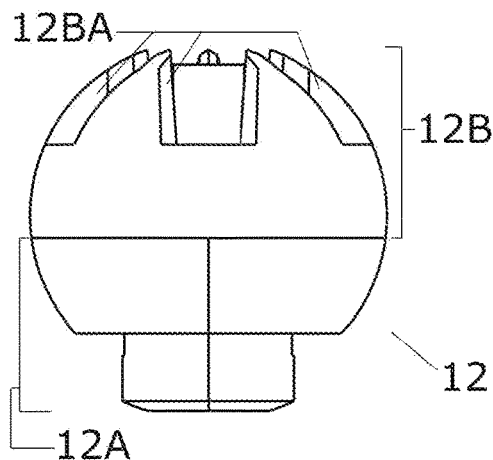
FIG. 24A illustrates a front view of the housing 12 according to an embodiment of the device 10.
Figure 24B:
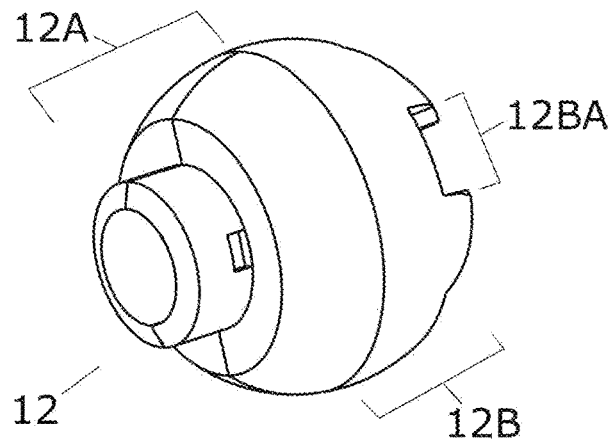
FIG. 24B illustrates a perspective view of the housing 12 according to an embodiment of the device 10.
Figure 24C:
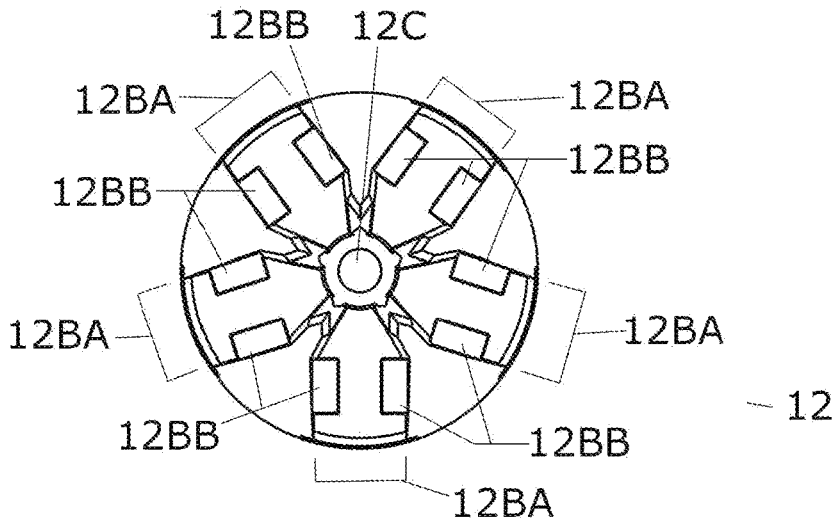
FIG. 24C illustrate a top view of the housing 12 according to an embodiment of the device 10.
Figure 24D:
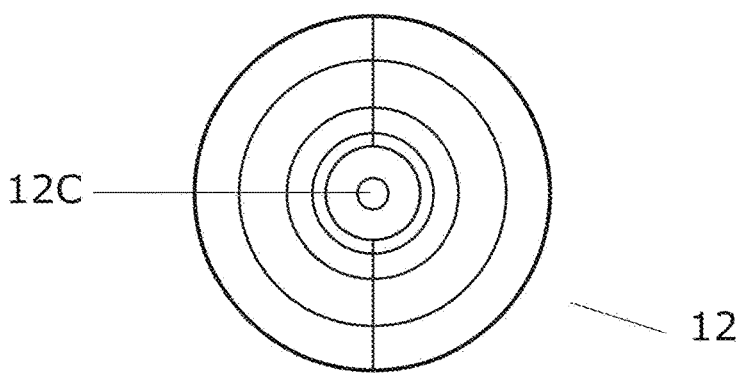
FIG. 24D illustrates a bottom view of the housing 12 according to an embodiment of the device 10.

Preferably, the housing 12 is configured in a geometric shape approximately or exactly, such as but not limited to: a spherical shape (as illustrated in FIG. 24A and FIG. 24B), a wedge shape, a cuboid shape, a rectangular shape, a potatoid shape, a conical shape, a cylinder shape, a pyramid shape, a prism shape, a tetrahedron shape, an icosahedron shape, an octahedron shape, a torus shape, a pentagonal shape, an ellipsoid shape, or a dodecahedron shape. Preferably, the housing 12 prevents over insertion of the device 10 inside the body orifice. Preferably, the housing 12 is made of a rigid material such as but not limited to: plastic, hard rubber, metal, glass and/or wood, however, the housing 12 may be made of a semi-rigid material such as but not limited to: plastic, silicone, and/or rubber, or the housing 12 may be made of a rigid material in combination with a semi-rigid and/or a soft material such as but not limited to: silicone, leather, and/or rubber. The housing 12 when made of metal, may be magnetized to increase the blood flow, relaxes muscles and ligaments of the body orifice region and therefore enhance the dilation and stretch of the body orifice during the utilization of the device 10. Preferably, the housing 12 is made with at least one coloration additive, however, the housing 12 may be made of no coloration additive. The housing 12 may be configured with at least one visual and/or tactile indication to indicate to the user how to use the device 10. The housing 12 may be configured with a color code and/or a serial number to distinguish a device 10 from another device 10 to facilitate the utilization for the user of several devices 10 (having or not the same features). For purposes of manufacturing and/or assembly optimization of the device 10, the housing 12 may be made in one, two (as illustrated in FIG. 25), three (as illustrated in FIG. 26) parts or more.

Figure 38A:
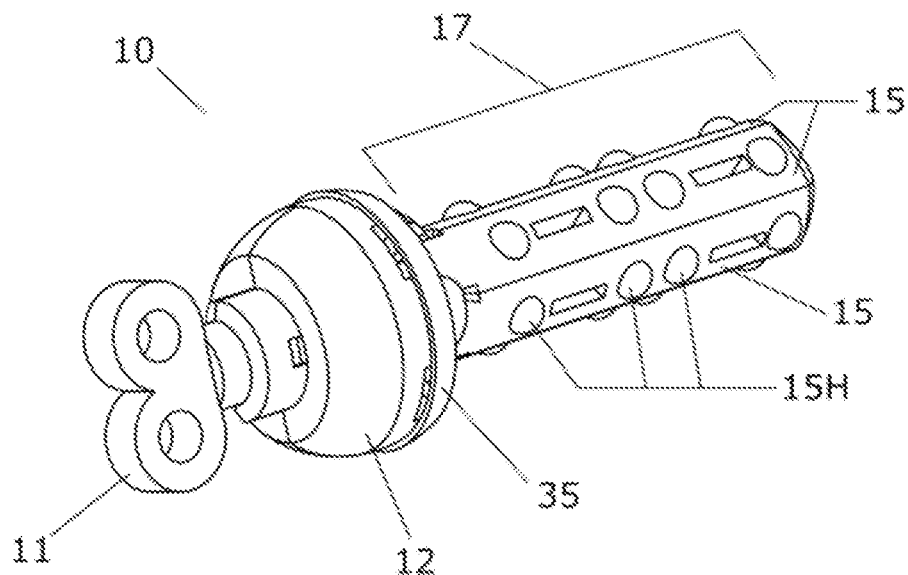
FIG. 38A illustrates a perspective view of the device 10 with the shaft 17 at its minimum girth size according to an embodiment of the device 10 (sheath 16 not illustrated).

When the housing 12 is made in several parts, the parts are connected to each other by such as but not limited to: interlocking, rubber banding 35 (as illustrated in FIG. 38A), silicone banding, wrapping, gluing, and/or screwing.

Figures 43A, 43B:
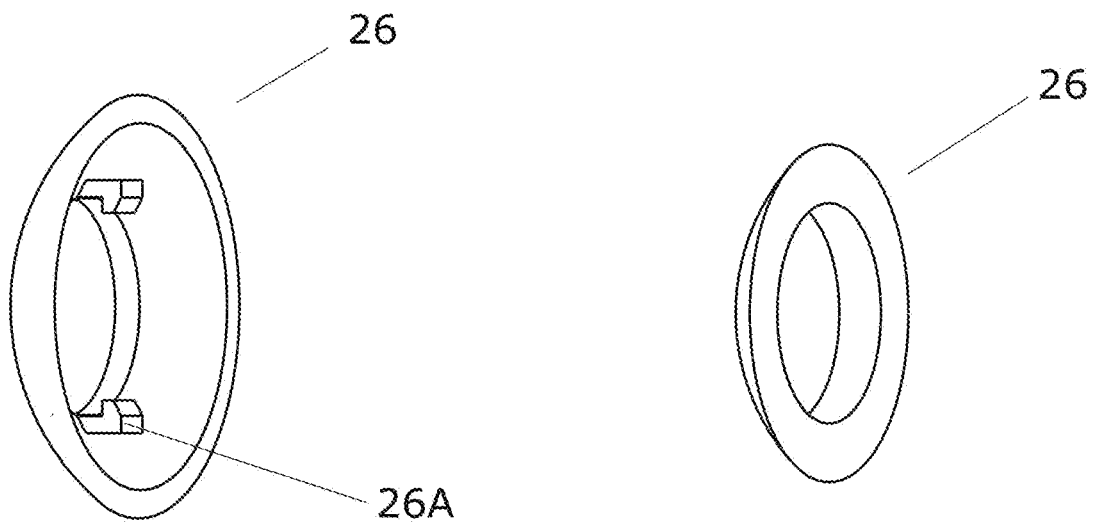
FIG. 43A illustrates a perspective view of the closure element 26 according to an embodiment.
FIG. 43B illustrates a perspective view of a closure element 26 according to an embodiment.
Figure 43C:
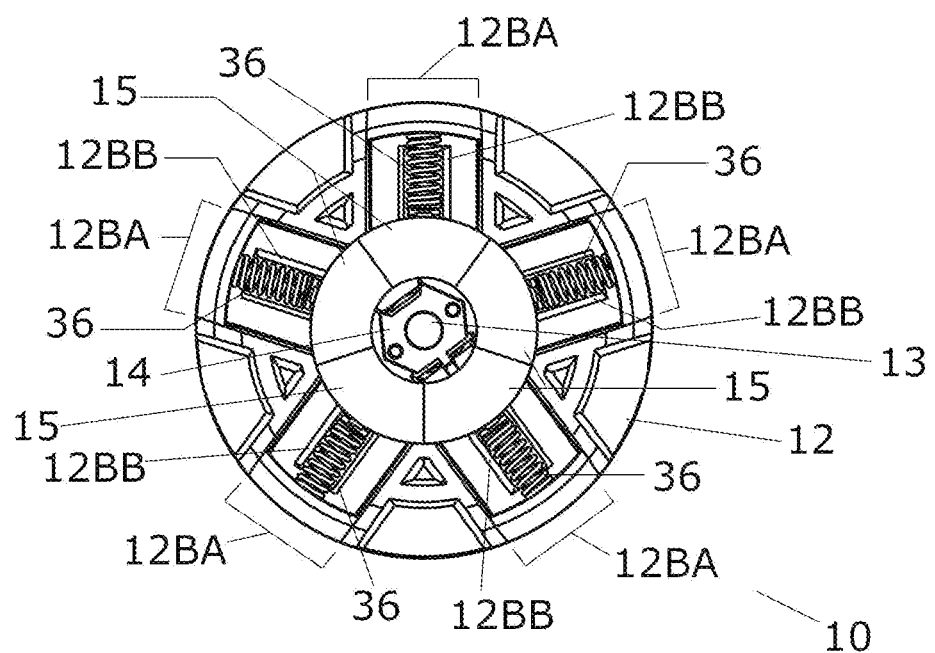
FIG. 43C illustrated a top view of the device 10 with the shaft 17 at its minimum girth size according to an embodiment of the device 10 (sheath 16 not illustrated).

In another embodiment, at least one shaft member groove 12BA may comprise at least one spring. The spring connects the first end 15A of the shaft member 15 that fits inside the shaft member groove 12BA having at least one spring. Preferably, the spring is such as but not limited to: a compression spring 36 (as illustrated in FIG. 43C) to facilitate the travel of the first end 15A of the shaft member 15 that fits inside the shaft member groove 12BA having at least one spring, perpendicularly to the longitudinal axis of the threaded shaft 13, in the direction of the longitudinal axis of the threaded shaft 13, when the girth size of the shaft 17 is decreased by the user, or the spring is such as but not limited to: a tension spring (not illustrated) to facilitate the travel of the first end 15A of the shaft member 15 that fits inside the shaft member groove 12BA having at least one spring, perpendicularly to the longitudinal axis of the threaded shaft 13, in the opposite direction of the longitudinal axis of the threaded shaft 13, when the girth size of the shaft 17 is increased by the user. Preferably, the spring is made of such as but not limited to: metal or plastic.

Figure 25A:
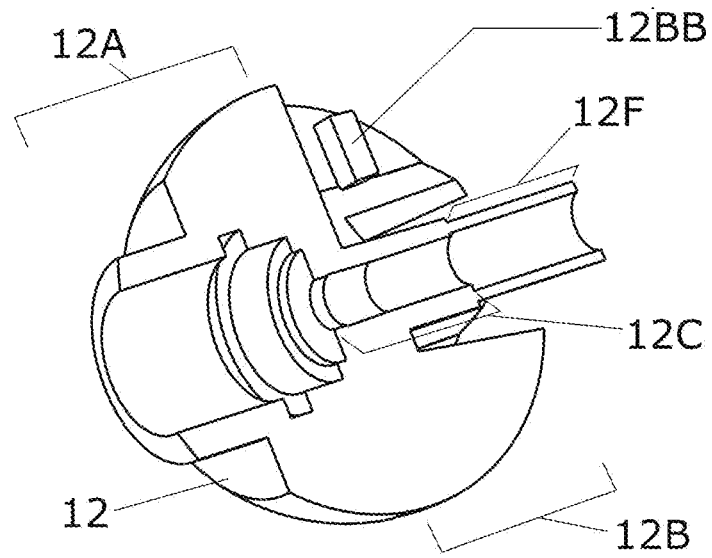
FIG. 25A illustrates a perspective view of a part of the housing 12 according to an embodiment of the device 10.
Figure 25B:
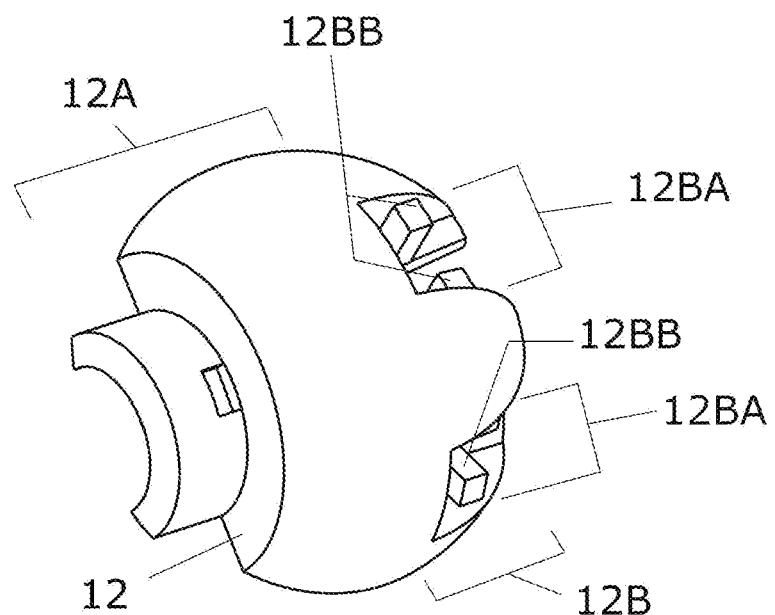
FIG. 25B illustrates a perspective view of a part of the housing 12 according to an embodiment of the device 10.
Figure 26A:
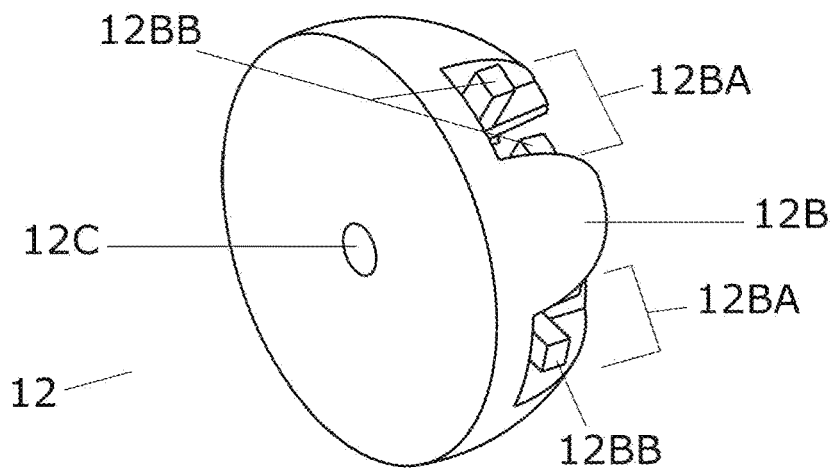
FIG. 26A illustrates a perspective view of a part of the housing 12 according to an embodiment of the device 10.
Figure 26B:
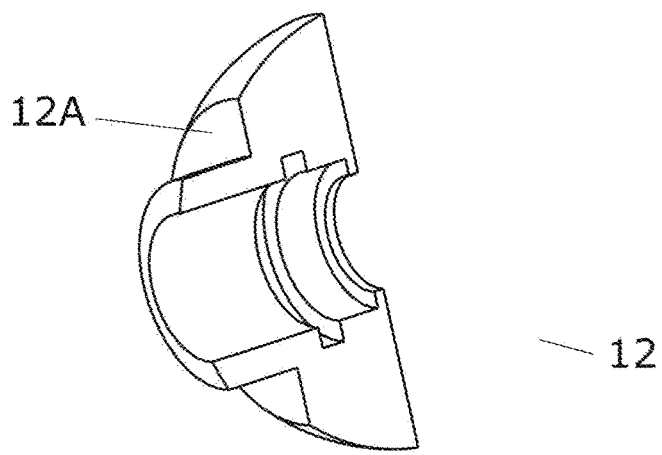
FIG. 26B illustrates a perspective view of a part of the housing 12 according to an embodiment of the device 10.
Figure 26C:
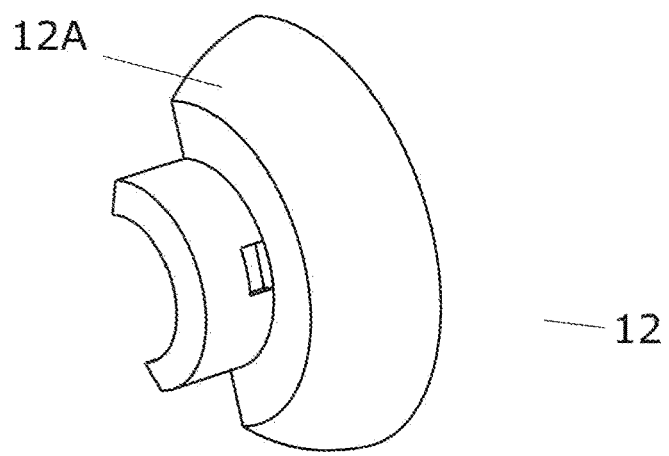
FIG. 26C illustrates a perspective view of a part of the housing 12 according to an embodiment of the device 10.

In another embodiment as illustrated in FIG. 25A, the housing 12 may comprise at least one module anti-rotation protrusion 12F. The module anti-rotation protrusion 12F is configured to slidably fit inside the housing anti-rotation cavity 14D of the module 14 having at least one housing anti-rotation cavity 14D (illustrated in FIG. 30F), such that when the threaded shaft 13 is rotated clockwise, the module 14, prevented from rotating around the longitudinal axis of the threaded shaft 13 by the interaction between the module anti-rotation protrusion 12F slidably connected to the housing anti-rotation cavity 14D, travels along the threaded shaft 13 in the direction of the housing 12, and when the threaded shaft 13 is rotated counter-clockwise, the module 14, prevented from rotating around the longitudinal axis of the threaded shaft 13 by the interaction between the module anti-rotation protrusion 12F slidably connected to the housing anti-rotation cavity 14D, travels along the threaded shaft 13 in the opposite direction of the housing 12. Preferably, the module anti-rotation protrusion 12F is made with the housing 12, however, the module anti-rotation protrusion 12F may be made separately and then secured to the housing 12. In that case, the module anti-rotation protrusion 12F is preferably made of such as but not limited to: metal and/or plastic.

Figure 27A:
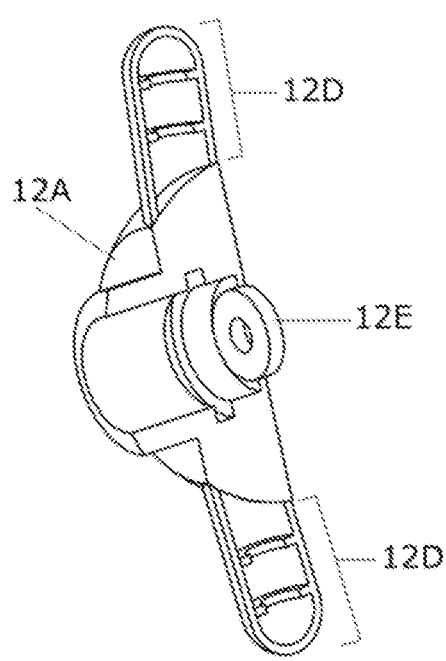
FIG. 27A illustrates a perspective view of a part of the housing 12 according to an embodiment of the device 10.
Figure 27B:
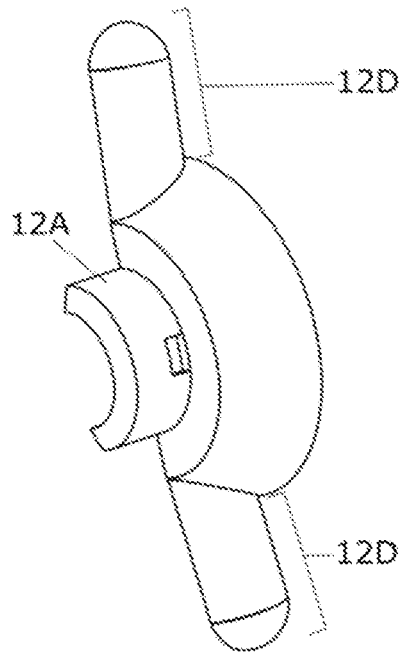
FIG. 27B illustrates a perspective view of a part of the housing 12 according to an embodiment of the device 10.
Figure 27C:
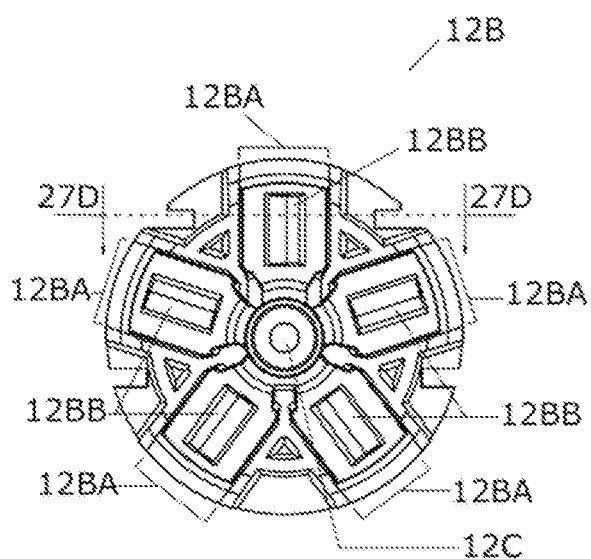
FIG. 27C illustrates a top view of a part of the housing 12 according to an embodiment of the device 10.
Figure 27D:
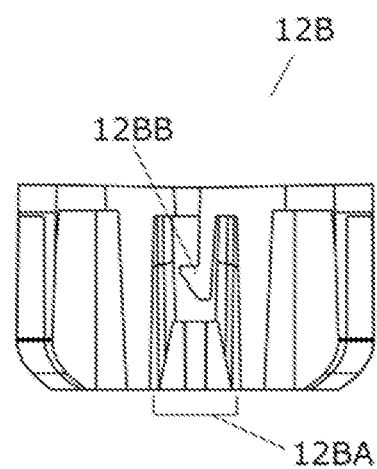
FIG. 27D illustrates a section view of FIG. 27C.

In another embodiment, as illustrated in FIG. 27A, the housing 12 may comprise at least one bearing 12E. Preferably, the bearing 12E is such as but not limited to: a plain bearing, a washer fastener, and/or a rolling-element bearing, made of such as but not limited to: metal and/or plastic. Preferably, the bearing 12E is configured to receive the first end 13A of the threaded shaft 13 and/or the second end 11B of the controller 11. The bearing 12E reduces friction and handling stress on the device 10 during the utilization of the device 10.

Figure 28A:
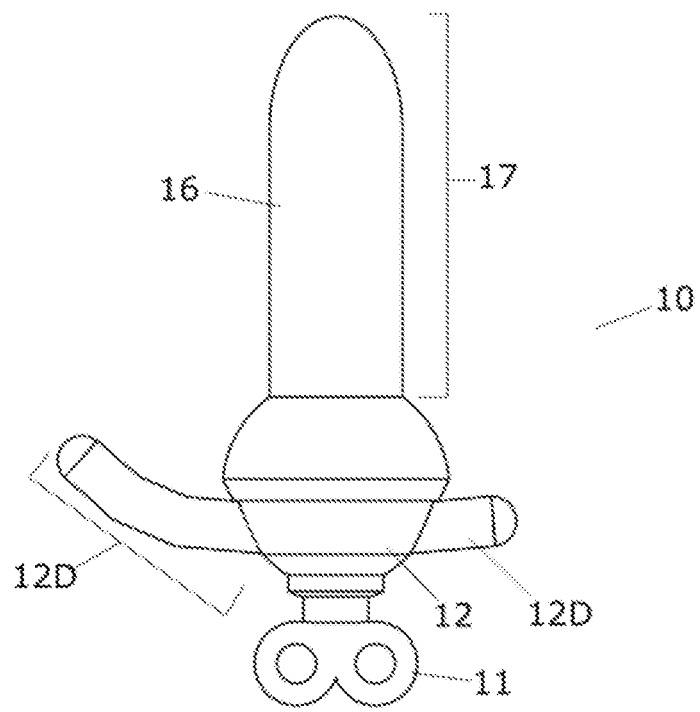
FIG. 28A illustrates a front view of the device 10 with the shaft 17 at its minimum girth size according to an embodiment of the device 10.
Figure 28B:
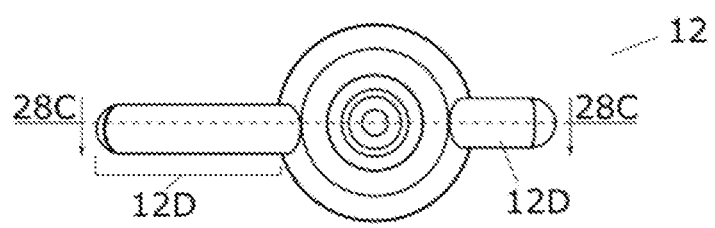
FIG. 28B illustrates a bottom view of the housing 12 according to an embodiment of the device 10.
Figure 28C:
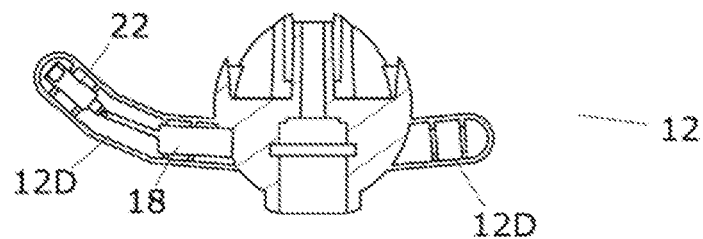
FIG. 28C illustrates a section view of FIG. 28B.

In another embodiment, as illustrated in FIG. 27 and FIG. 28, the housing 12 may comprise at least one housing external protrusion 12D. The housing external protrusion 12D prevents the device 10 to rotate inside the body orifice when the user performs the adjustment of the device 10, by pressing against the nearest body part of the body orifice where the shaft 17 of the device 10 is inserted. The housing external protrusion 12D is also a handle to facilitate the utilization of the device 10. The housing external protrusion 12D may comprise at least one: an electronic part 18 (illustrated in FIG. 28C), a vibration motor 22 (illustrated in FIG. 28C; vibration motor 22 described in Vibration motor section), a heating element (not illustrated; heating element described in Heating element section), a heart rate monitor (not illustrated; heart rate monitor described in Heart rate monitor section), an electrical stimulation electrode (not illustrated; electrical stimulation electrode described in Electrical stimulation electrode section), a penis ring (not illustrated; penis ring described in Penis ring section), a weight 32 (not illustrated in this embodiment; weight 32 described in Weight section), and/or a girth adjustment indicator 23 (not illustrated in this embodiment; girth adjustment indicator 23 described in Girth adjustment indicator section). The housing external protrusion 12D also prevents over-insertion of the device 10 into the body orifice. The housing external protrusion 12D may also be configured to stimulate by contact another body part (such as a vagina when the device 10 is inserted into a female anus) to enhance the body orifice dilation procedure during the utilization of the device 10. The housing external 12D may also be configured to stimulate another body orifice by being inserted into it (such as a vagina when the device 10 is inserted into an anus) to enhance the body orifice dilation procedure during the utilization of the device 10. The housing external protrusion 12D is preferably made with the housing 12, however, the housing external protrusion 12D may be made separately and configured to be removably secured to the housing 12, which means that the housing external protrusion 12D may be repeatedly: secured to the housing 12, then removed from the housing 12, and then secured again to the housing 12. In that case, the housing external protrusion 12D is preferably made of a rigid material such as but not limited to: plastic, hard rubber, metal, glass and/or wood, however, the housing external protrusion 12D may be made of a semi-rigid material such as but not limited to: plastic, silicone, and/or rubber, or the housing external protrusion 12D may be made of a rigid material in combination with a semi-rigid and/or a soft material such as but not limited to: silicone, leather, and/or rubber. FIG. 27A illustrates a perspective view of a part of the housing 12 in this embodiment. FIG. 27B illustrates a perspective view of a part of the housing 12 in this embodiment. FIG. 28A illustrates a front view of the device 10 with the shaft 17 at its minimum girth size in this embodiment. FIG. 28B is a bottom view of the housing 12 according to this embodiment. FIG. 28C illustrates a section view of FIG. 28B. This embodiment provides others features that enhance the body orifice dilation and stretch procedure for the user during the utilization of the device 10.

Figure 45:
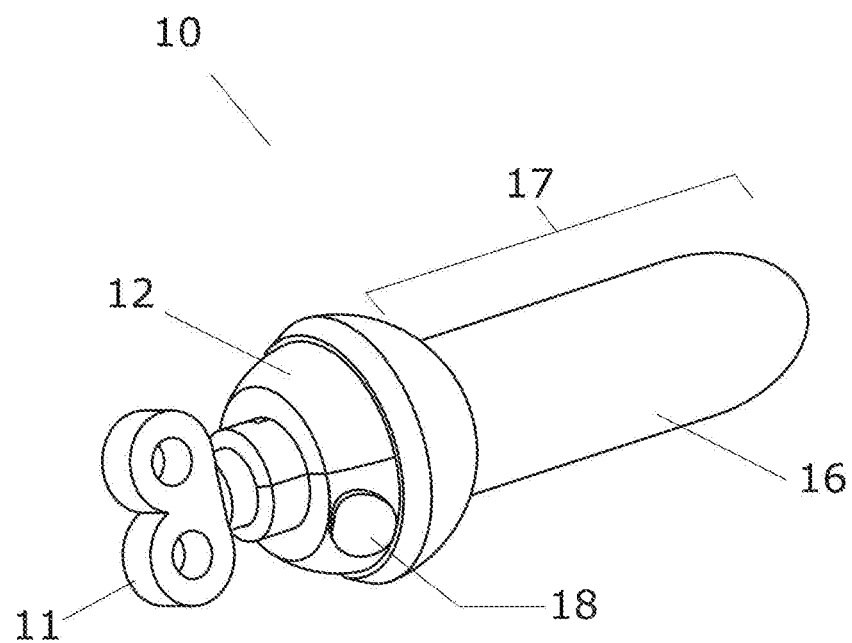
FIG. 45 illustrates a perspective view of the device 10 with the shaft 17 at its minimum girth size according to an embodiment of the device 10.

In another embodiment, the housing 12 may comprise at least one: an electronic part 18 (as illustrates in FIG. 45), a vibration motor 22 (as illustrated in FIG. 29A), a girth adjustment indicator 23 as illustrated in FIG. 29B, a heating element (not illustrated), a heart rate monitor (not illustrated), an electrical stimulation electrode (not illustrated), a penis ring (not illustrated), and/or a weight 32 (illustrated in FIG. 29B). This embodiment provides others features that enhance the body orifice dilation and stretch procedure for the user during the utilization of the device 10.

Module

In a preferred embodiment, the module 14 has at least one conical section with a slant height 14A, at least one anti-rotation connector selected from a group consisting of: a linear anti-rotation connector 14B, a capital letter T shape anti-rotation connectors 24 and an inclined capital letter T shape anti-rotation connector 25, and a canal 14C, as illustrated in FIG. 30. In a preferred embodiment as illustrated in FIG. 2, FIG. 3 and FIG. 4, the device 10 comprises at least two modules 14 having one conical section with a slant height 14A, at least one anti-rotation connector, and a canal 14C (module 14 in this embodiment illustrated in FIG. 30A, FIG. 30B, FIG. 30D, FIG. 30E, FIG. 30G, and FIG. 30H), or at least one module 14 having at least two conical sections with a slant height 14A, at least one anti-rotation connector, and a canal 14C (device 10 not illustrated in this embodiment; module 14 in this embodiment illustrated in FIG. 30C and FIG. 30F) per threaded shaft 13. However, it is feasible to configure the device 10 with one module 14 having one conical section with a slant height 14A, at least one anti-rotation connector, and a canal 14C (device 10 not illustrated in this embodiment) per threaded shaft 13.

Preferably, the conical section with a slant height 14A is configured in an approximately or exactly conical shape, and therefore configured with an apex, a slant height and a flat base. The slant height of the conical section with a slant height 14A is greater than 0.1 inch. Preferably, the canal 14C passes through the conical section with a slant height 14A, from the apex to the center of the flat base. The canal 14C may be configured to not pass through the entire module 14 when the device 10 only has one module 14 or when the module 14 is located at second end of the threaded shaft 13. The canal 14C is such as: a threaded canal, a threaded canal having at least one fastener cavity, or a non-threaded canal having at least one fastener cavity 14CA (as illustrated in FIG. 30E, FIG. 30F and FIG. 30G). The function of the canal 14C is to interact mechanically with the threaded shaft 13 when the threaded shaft 13 rotates, to make the module 14 (prevented from rotating around the longitudinal axis of the threaded shaft 13) travel along the threaded shaft 13. When the canal 14C is threaded, the mechanical interaction between the canal 14C and the threaded shaft 13 is direct, when the canal 14C is non-threaded having at least one fastener cavity, in which the fastener cavity includes at least one fastener such as but not limited to: a nut fastener, and/or a wing nut fastener, the mechanical interaction between the canal 14C and the threaded shaft 13 is via the fastener inserted inside the fastener cavity, and when the canal 14C is threaded having at least one fastener cavity, in which the fastener cavity includes at least one fastener such as but not limited to: a nut fastener, and/or a wing nut fastener, the mechanical interaction between the canal 14C and the threaded shaft 13 is direct and via the fastener inserted inside the fastener cavity. The canal 14C is configured to receive the threaded shaft 13, such that when the threaded shaft 13 is rotated clockwise, the module 14 prevented from rotating around the longitudinal axis of the threaded shaft 13 by the interaction between at least one anti-rotation connector of the module 14 slidably connected to at least one module connector groove 15D of at least one shaft member 15, travels along the threaded shaft 13 in the direction of the housing 12, and when the threaded shaft 13 is rotated counter-clockwise, the module 14 prevented from rotating around the longitudinal axis of the threaded shaft 13 by the interaction between at least one anti-rotation connector of the module 14 slidably connected to at least one module connector groove 15D of at least one shaft member 15, travels along the threaded shaft 13 in the opposite direction of the housing 12.

The flat base of the conical section with a slant height 14A of at least one module 14 may be configured to slidably receive (not illustrated) the apex of the conical section with a slant height 14A of the following module 14 on the threaded shaft 13, so as to prevent undesired rotations of the modules 14 slidably connected, around the longitudinal axis of the threaded shaft 13.

Preferably, the apex of the conical section with a slant height 14A is in the direction of the housing 12, however, the apex of the conical section with a slant height 14A may be in the opposite direction of the housing 12, reversing the direction of the rotation of the threaded shaft 13 to increase and decrease the girth size of the shaft 17. To reduce friction and handling stress on the plurality of shaft members 15 during the utilization of the device 10, the module 14 may be configured with at least one friction reducer 34. The friction reducer 34 is such as but not limited to: a wheel and its axle held in a cavity (as illustrated in FIG. 30F) and/or a ball held in a cavity (not illustrated).

To reduce friction and handling stress on the plurality of shaft members 15 during the utilization of the device 10, the module 14 may be lubricated.

Preferably, the module 14 is made of a rigid material such as but not limited to: plastic and/or metal. The module 14 when made of metal, may be magnetized to increase the blood flow, relaxes muscles and ligaments of the body orifice region and therefore enhance the dilation and stretch of the body orifice during the utilization of the device 10. Preferably, the conical section with a slant height 14A is configured in an approximately or exactly, conical shape, however, the conical section with a slant height 14A may be configured in a geometric shape approximately or exactly, such as but not limited to: a spherical shape, a triangle shape, a pyramid shape, a cuboid shape, a prism shape, a potatoid, an icosahedron shape, a octahedron shape, a pentagonal shape, an ellipsoid shape, a dodecahedron shape and/or a rectangular shape.

Figure 30A:
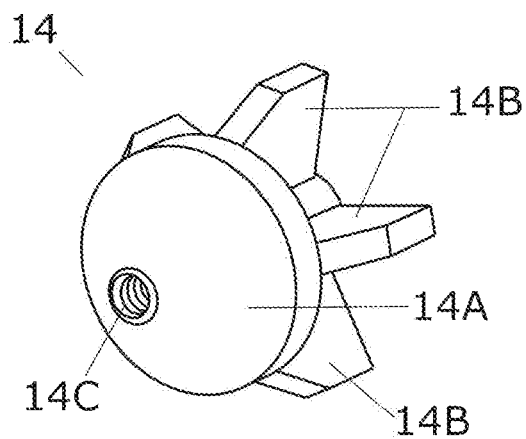
FIG. 30A illustrates a perspective view of a module 14 according to an embodiment.
Figure 30B:
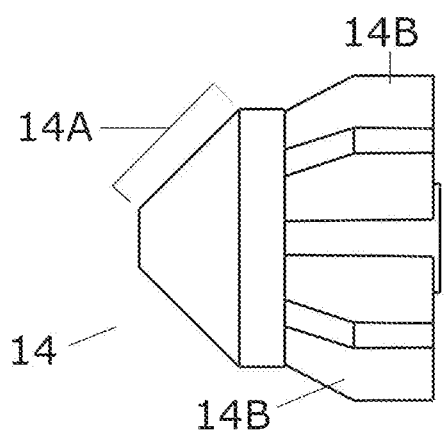
FIG. 30B illustrates a side view of a module 14 according to an embodiment.
Figure 30C:
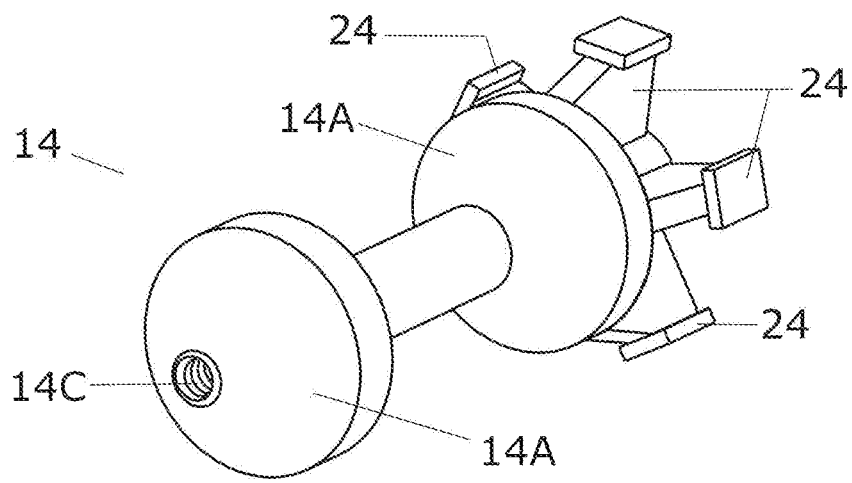
FIG. 30C illustrates a perspective view of a module 14 according to an embodiment.
Figure 30D:
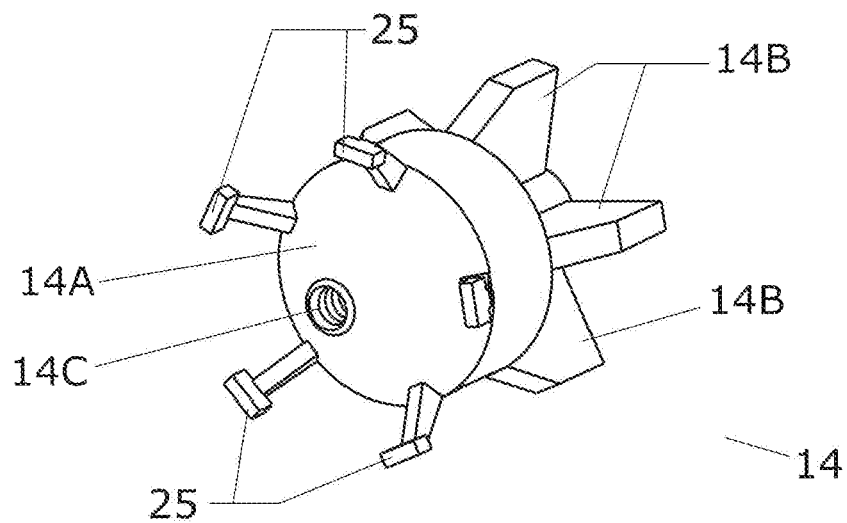
FIG. 30D illustrates a perspective view of a module 14 according to an embodiment.

As illustrated in FIG. 30A to FIG. 30H, the anti-rotation connector of the module 14 is: a linear anti-rotation connector 14B (illustrated in FIG. 30A, FIG. 30B, FIG. 30D, FIG. 30E, and FIG. 30F), a capital letter T shape anti-rotation connector 24 (illustrated in FIG. 30C, and FIG. 30G), and/or an inclined capital letter T shape anti-rotation connector 25 (illustrated in FIG. 30D, and FIG. 30H). The function of the anti-rotation connector of the module 14 (slidably connected to the module connector groove 15D of the shaft member 15) is to prevent the module 14 from rotating when the threaded shaft 13 rotates, and therefore the module 14 travels along the threaded shaft 13 when the threaded shaft 13 rotates, and to guide the shaft member 15 to travel perpendicularly to the longitudinal axis of the threaded shaft 13 in the direction or the opposite direction, of the longitudinal axis of the threaded shaft 13.

As illustrated in FIG. 30A, FIG. 30B, FIG. 30D, FIG. 30E, and FIG. 30F, the linear anti-rotation connector 14B is positioned approximately or exactly perpendicularly to the longitudinal axis of threaded shaft 13.

As illustrated in FIG. 30C, and FIG. 30G, the capital letter T shape anti-rotation connector 24 is configured in an approximately or exactly similar shape of the capital letter T positioned approximately or exactly perpendicularly to the longitudinal axis of threaded shaft 13. When the module 14 is configured with a capital letter T shape anti-rotation connector 24, the shaft member 15 is configured to slidably receive via the module connector groove 15D (illustrated in FIG. 31) the capital letter T shape anti-rotation connector 24.

As illustrated in FIG. 30D, and FIG. 30H, the inclined capital letter T shape anti-rotation connector 25 is configured in an approximately or exactly similar shape of an inclined capital letter T. The inclined capital letter T shape anti-rotation connector 25 makes an angle greater than 0.1° with the longitudinal axis of the threaded shaft 13. When the module 14 is configured with an inclined capital letter T shape anti-rotation connector 25, the shaft member 15 is configured to slidably receive via the module connector groove 15D (illustrated in FIG. 31) the inclined capital letter T shape anti-rotation connector 25.

FIG. 30A illustrates a perspective view of the module 14 having one conical section with a slant height 14A, a plurality of linear anti-rotation connectors 14B, and a canal 14C in one embodiment. FIG. 30B illustrates a side view of the module 14 having one conical section with a slant height 14A, a plurality of linear anti-rotation connectors 14B, and a canal 14C in one embodiment. FIG. 30C illustrates a perspective view of the module 14 having two conical sections with a slant height 14A, a plurality of capital letter T shape anti-rotation connectors 24, and a canal 14C in one embodiment. FIG. 30D illustrates a perspective view of the module 14 having one conical section with a slant height 14A, a plurality of linear anti-rotation connectors 14B and a plurality of inclined capital letter T shape anti-rotation connectors 25, and a canal 14C in one embodiment. FIG. 30E illustrates a perspective view of the module 14 having one conical section with a slant height 14A, a plurality of linear anti-rotation connectors 14B, and a canal 14C in one embodiment. FIG. 30F illustrates a perspective view of the module 14 having two conical sections with a slant height 14A, a plurality of linear anti-rotation connectors 14B, and a canal 14C in one embodiment. FIG. 30G illustrates a perspective view of the module 14 having one conical section with a slant height 14A, a plurality of capital letter T shape anti-rotation connectors 24, and a canal 14C in one embodiment. FIG. 30H illustrates a perspective view of the module 14 having one conical section with a slant height 14A, a plurality of inclined capital letter T shape anti-rotation connectors 25, and a canal 14C in one embodiment.

In another embodiment, the module 14 (as illustrated in FIG. 30F) may comprise at least one housing anti-rotation cavity 140. The housing anti-rotation cavity 14D is configured to slidably receive the module anti-rotation protrusion 12F of the housing 12 having at least one module anti-rotation protrusion 12F, such that when the threaded shaft 13 is rotated clockwise, the module 14, prevented from rotating around the longitudinal axis of the threaded shaft 13 by the interaction between the housing anti-rotation cavity 14D and the module anti-rotation protrusion 12F, travels into the direction of the housing 12 and when the threaded shaft 13 is rotated counter-clockwise, the module 14, prevented from rotating around the longitudinal axis of the threaded shaft 13 by the interaction between the module anti-rotation protrusion 12F and the housing anti-rotation cavity 14D, travels in the opposite direction of the housing 12. This embodiment is such that, when the user performs the adjustment of the device 10, the interaction between the module anti-rotation protrusion 12F and the housing anti-rotation cavity 140 prevents the module 14 of undesired rotation and reinforces the global structure of the device 10. Attention to the fact that it is possible to locate the housing anti-rotation cavity 14D in the housing 12 with the module anti-rotation protrusion 12F on the module 14.

In another embodiment as illustrated in FIG. 58, when the apex of the conical section with a slant height 14A is in the opposite direction of the housing 12, at least one module 14 may be located at the second end 13C of the threaded shaft 13 to expand at the tip end 160 of the sheath 16 the length of the sheath 16 (sheath 16 described in Sheath section) and therefore the length of the shaft 17, when the girth size of the shaft 17 is increased by the user. FIG. 58A illustrates a front view of the device 10 with the shaft 17 at its minimum girth size according to an embodiment of the device 10 (sheath 16 not illustrated in FIG. 58A, and only one shaft member 15 illustrated in FIG. 58A). As illustrated in FIG. 58, in this embodiment the module 14 located at the second end 130 of the threaded shaft 13 to expand the length of the sheath 16 may be configured with a module cap 14E that closes, the farthest side from the housing 12, the canal 140. This embodiment provides other features to enhance the body dilation procedure for the user such as length adjustment of the device 10 during the utilization of the device 10. FIG. 58B illustrates a front view of the device 10 with the shaft 17 at its maximum girth size according to an embodiment of the device 10 (sheath 16 not illustrated in FIG. 58B, and only one shaft member 15 illustrated in FIG. 58B). FIG. 58C illustrates a bottom view of FIG. 58A. FIG. 58D illustrates a bottom view of FIG. 58B. FIG. 58E illustrates a section view of FIG. 58C. FIG. 58F illustrates a section view of FIG. 58D.

Shaft Member

Figure 31A:
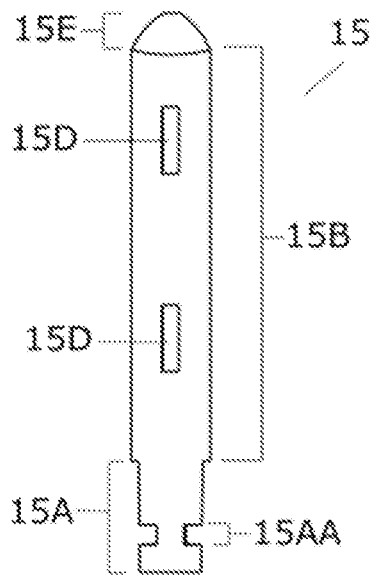
FIG. 31A illustrates a front view of a shaft member 15 according to an embodiment.
Figure 31B:
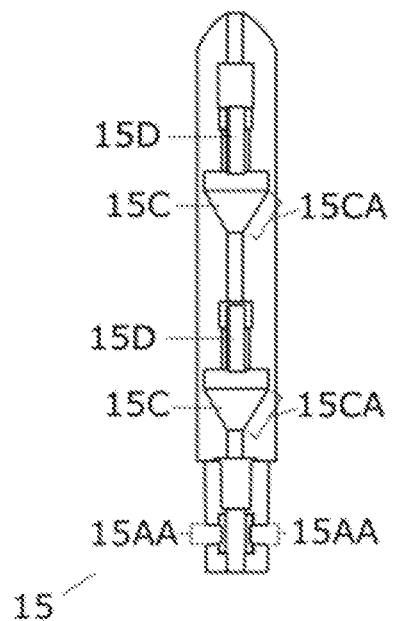
FIG. 31B illustrates a back view of a shaft member 15 according to an embodiment.
Figure 31C:
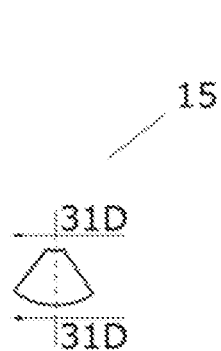
FIG. 31C illustrates a top view of a shaft member 15 according to an embodiment.
Figure 31D:
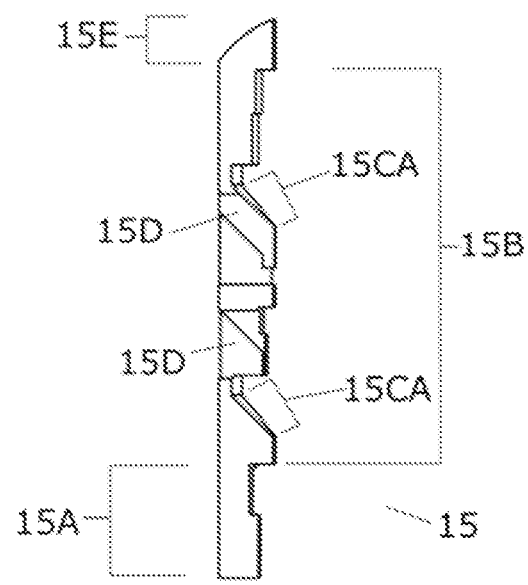
FIG. 31D illustrates a section view of FIG. 31C.
Figure 32A:
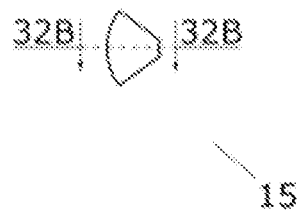
FIG. 32A illustrates a top view of a shaft member 15 according to an embodiment.

In a preferred embodiment the device 10 comprises a plurality of shaft members 15. In a preferred embodiment, a shaft member 15 has a first end 15A having at least one housing groove 15AA, a middle section 15B, at least one module cavity 15C with a sloped edge 15CA, at least one module connector groove 15D, and a tip end 15E (shaft member 15 illustrated in FIG. 31). The direction of orientation going from the first end 15A to the tip end 15E or from the tip end 15E to the first end 15A of the shaft member 15 is referred hereinafter to as "the longitudinal axis of the shaft member". The tip end 15E may be configured with a profiled shape as illustrated in FIG. 320 and FIG. 32D, to facilitate the insertion of the shaft 17 into the body orifice.

Attention being called to the fact that the device 10 preferably comprises more than four shaft members 15 per threaded shaft 13 (five or six shaft members in a preferred embodiment) with the aim to generate during the adjustment, a substantially uniform pressure, from the center toward the lateral surface area of the body orifice, over the entire lateral surface area of the body orifice, or with the aim to reduce a substantially uniform pressure, from the entire lateral surface area of the body orifice. This specific repartition of the pressure has the aim to provide an optimum performance and comfort for the user for the dilation and stretch of body orifices, however, it is feasible to configure the device with only two (as illustrated in FIG. 33, sheath 16 not illustrated), three or four shaft members (device 10 not illustrated in this embodiment). Preferably, the shaft member 15 has as many module cavities 15C as the module 14 (or a plurality of modules 14) comprises conical sections with a slant height 14A. Preferably, a conical section with a slant height 14A of the module 14 is configured on the middle section 13B and/or the second end 13C of the threaded shaft 13 to slidably fit inside a module cavity 15C. During the adjustment of the device 10, when the girth size of the shaft 17 is increased, the slant height of the conical section with a slant height 14A of the module 14 slides against the sloped edge 15CA outside of the module cavity 15C, making each shaft member 15 travels perpendicularly to the longitudinal axis of the threaded shaft 13 in the opposite direction of the longitudinal axis of the threaded shaft 13, each longitudinal axis of each shaft member 15 is maintained approximatively or exactly parallel with the longitudinal axis of the threaded shaft 13, and when the girth size of the shaft 17 is decreased, in interaction with the sheath and the anti-rotation connector, the slant height of the conical section with a slant height 14A of the module 14 slides against the sloped edge 15CA inside of the module cavity 15C, making each shaft member 15 travels perpendicularly to the longitudinal axis of the threaded shaft 13 in the direction of the longitudinal axis of the threaded shaft 13, each longitudinal axis of each shaft member 15 is maintained approximatively or exactly parallel with the longitudinal axis of the threaded shaft 13, and therefore the slant height value of the slant height of the conical section with a slant height 14A and the slope of the sloped edge 15CA of the module cavity 150 define partially the specific characteristics of the adjustment of the device 10, the highest the value of the slant height of the conical section with a slant height 14A and/or the steeper the slope of the sloped edge 15CA of the module cavity 15C, the more or less rotations of the controller 11 the user requires to reach the maximum and minimum girth size of the shaft 17 offered by the device 10. However, the sloped edge 15CA of the module cavity 15C can slide against any another edge of the module 14, in the case that the conical section with a slant height 14A of the module 14 is configured in a different geometric shape than an approximatively or exactly conical shape.

The plurality of shaft members 15 is configured to surround the threaded shaft 13, and the module 14 (or a plurality of modules 14). When the shaft 17 of the device 10 is at its minimum girth size, the girth size of the plurality of shaft members 15 is greater than 1.25 inch. The girth size of the plurality of shaft members 15 is calculated using the lateral surface area of the cylinder shape formed by the plurality of shaft members 15. Preferably, the length of the shaft member 15, from the first end 15A to the tip end 15E is greater than 1 inch.

Figure 38B:
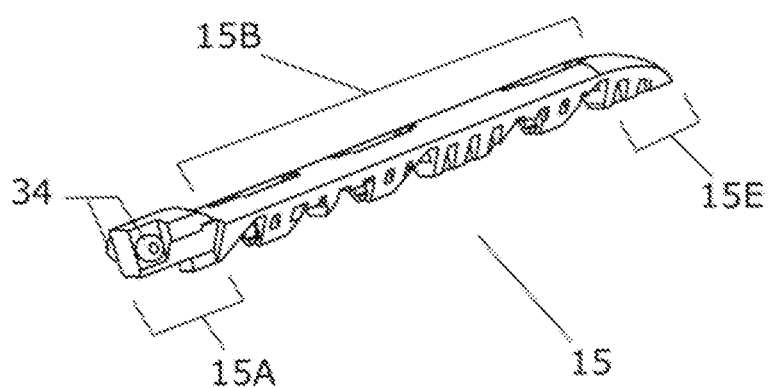
FIG. 38B illustrates a perspective view of a shaft member 15 according to an embodiment.

To reduce friction and handling stress on the housing 12 and/or the module 14 (or a plurality of modules 14) during the utilization of the device 10, each shaft member 15 may be configured with at least one friction reducer 34. The friction reducer 34 is such as but not limited to: a wheel and its axle held in a cavity (as illustrated in FIG. 38B) and/or a ball held in a cavity (not illustrated).

To reduce friction and handling stress on the housing 12 and the module 14 (or a plurality of modules 14) during the utilization of the device 10, each shaft member 15 may be lubricated.

Figure 32D:
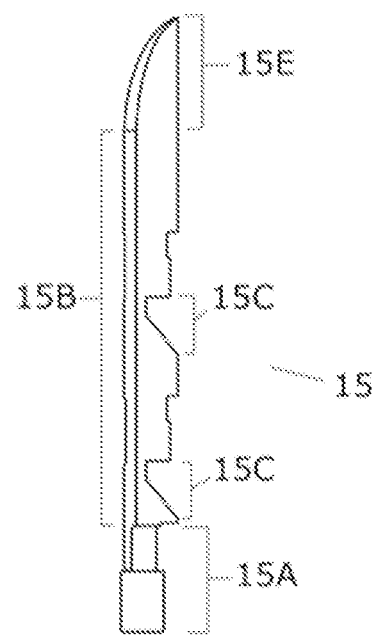
FIG. 32D illustrates a side view of a shaft member 15 according to an embodiment.
Figure 33A:
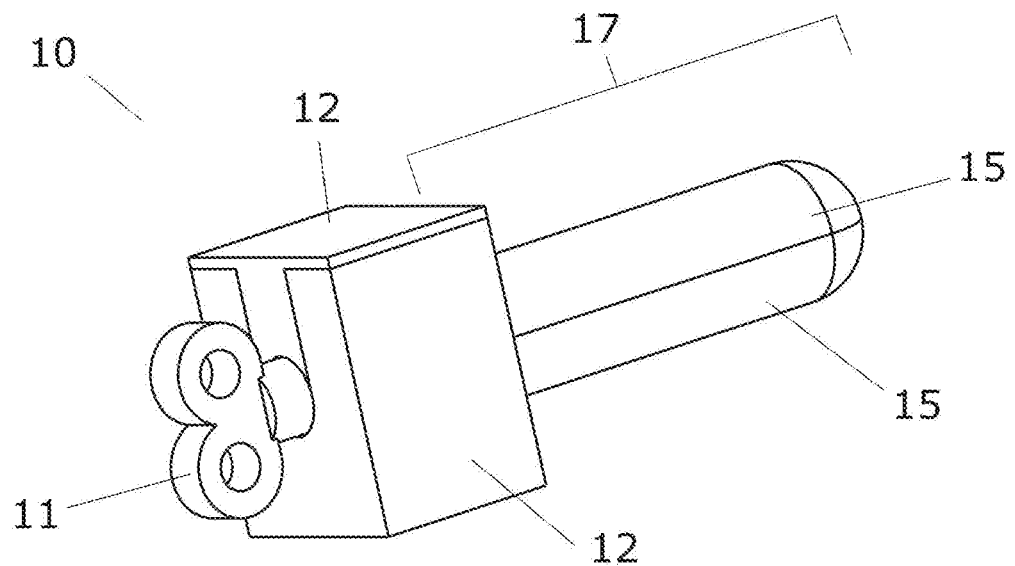
FIG. 33A illustrates a perspective view of the device 10 with the shaft 17 at its minimum girth size according to an embodiment of the device 10 (sheath 16 not illustrated).
Figure 33B:
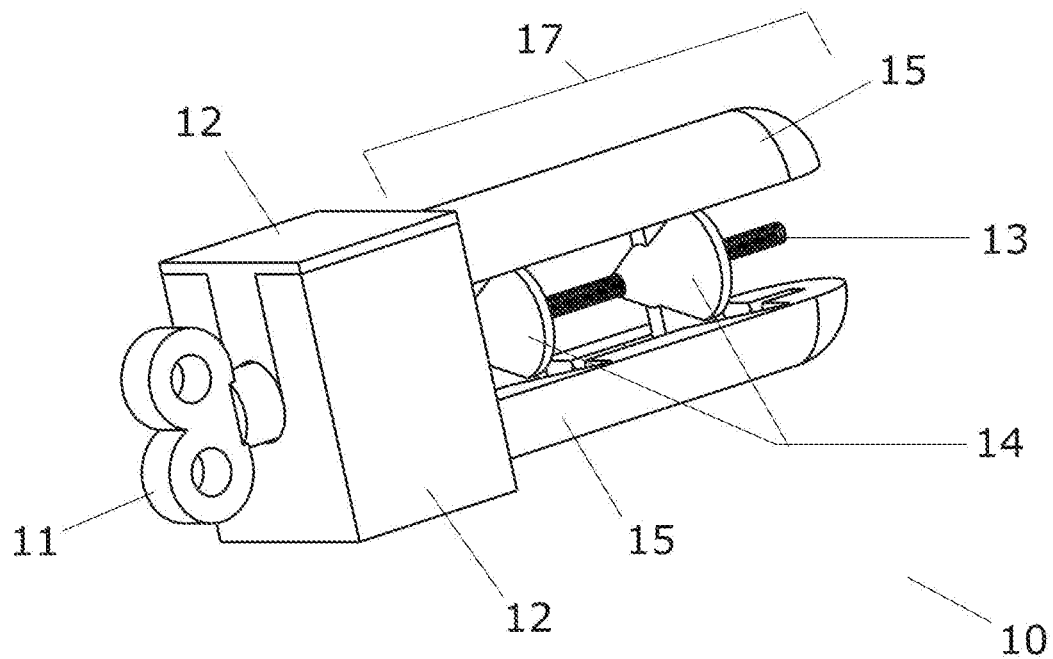
FIG. 33B illustrates a perspective view of the device 10 with the shaft 17 at its maximum girth size according to an embodiment of the device 10 (sheath 16 not illustrated).
Figure 34A:
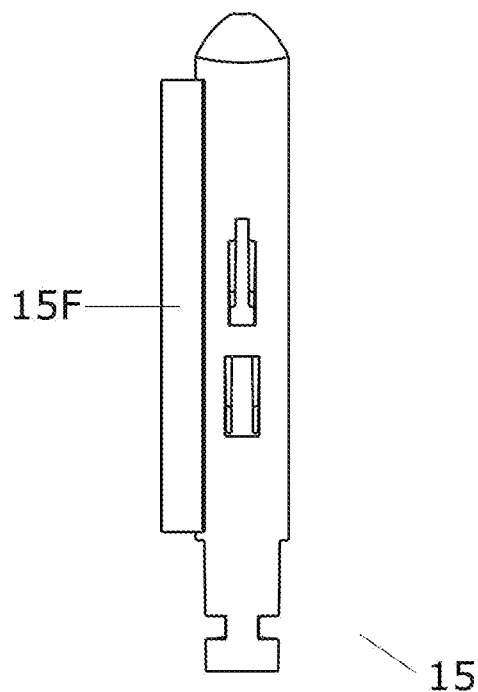
FIG. 34A illustrates a front view of a shaft member 15 according to an embodiment, and when the shaft 17 of the device 10 is at its minimum girth size.
Figure 34B:
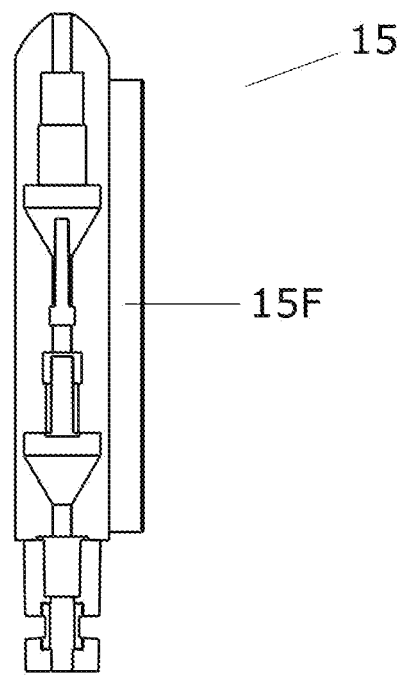
FIG. 34B illustrates a back view of a shaft member 15 according to an embodiment, and when the shaft 17 of the device 10 is at its minimum girth size.
Figure 34C:
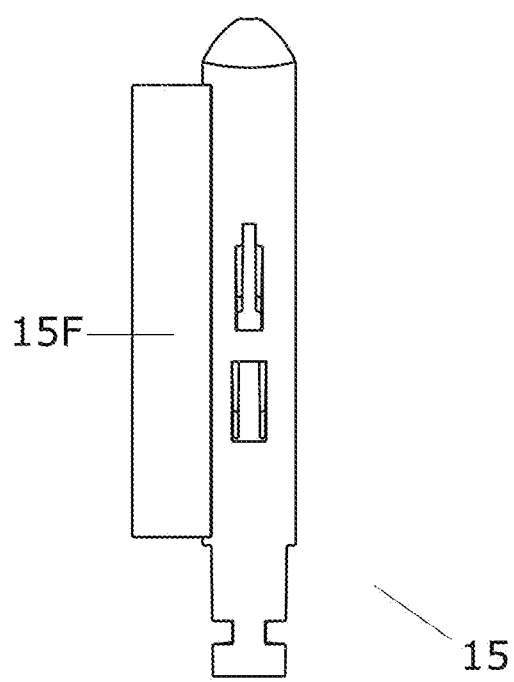
FIG. 34C illustrates a front view of a shaft member 15 according to an embodiment, and when the shaft 17 of the device 10 is at its maximum girth size.
Figure 34D:
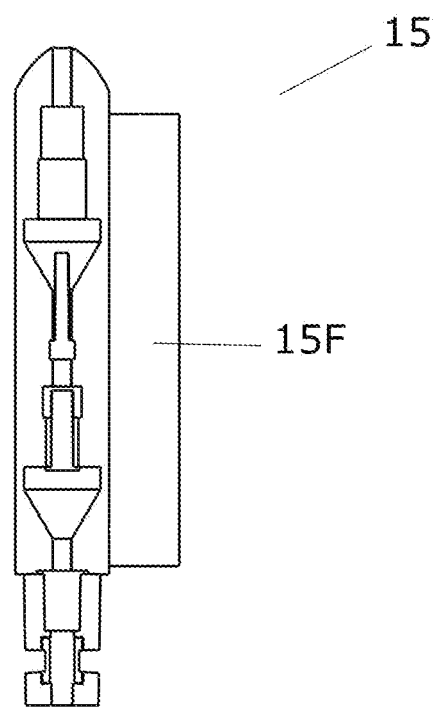
FIG. 34D illustrates a back view of a shaft member 15 according to an embodiment, and when the shaft 17 of the device 10 is at its maximum girth size.
Figure 36A:
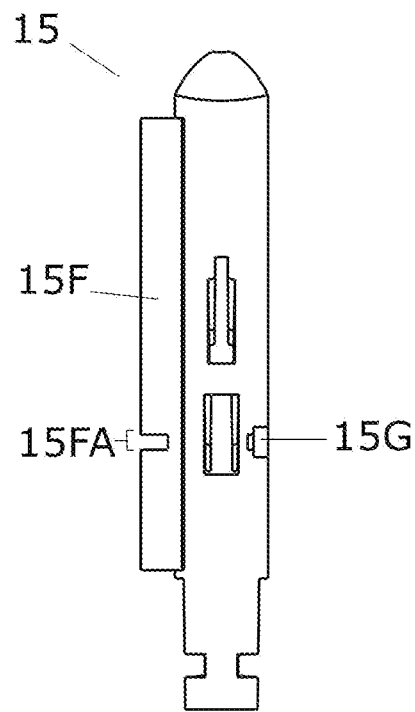
FIG. 36A illustrates a front view of a shaft member 15 according to an embodiment, and when the shaft 17 of the device 10 is at its minimum girth size.
Figure 36B:
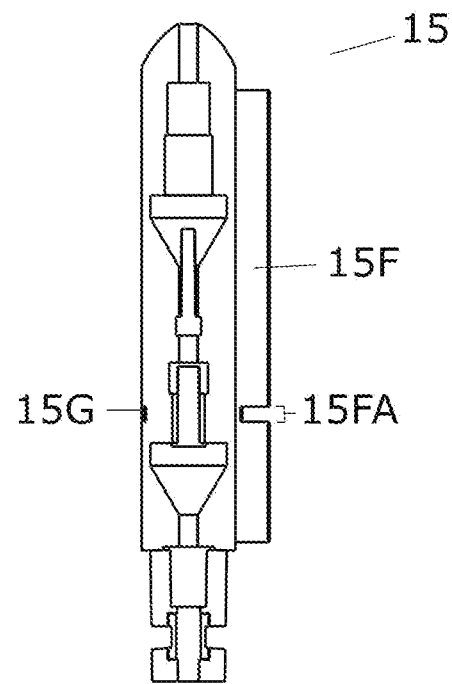
FIG. 36B illustrates a back view of a shaft member 15 according to an embodiment, and when the shaft 17 of the device 10 is at its minimum girth size.
Figure 36C:
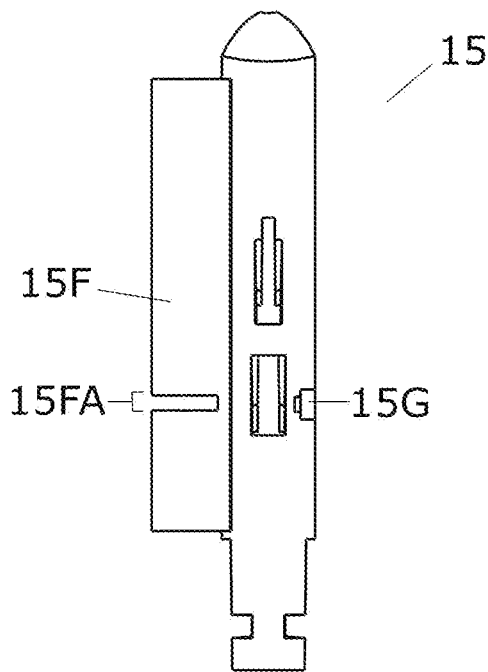
FIG. 36C illustrates a front view of a shaft member 15 according to an embodiment, and when the shaft 17 of the device 10 is at its maximum girth size.
Figure 36D:
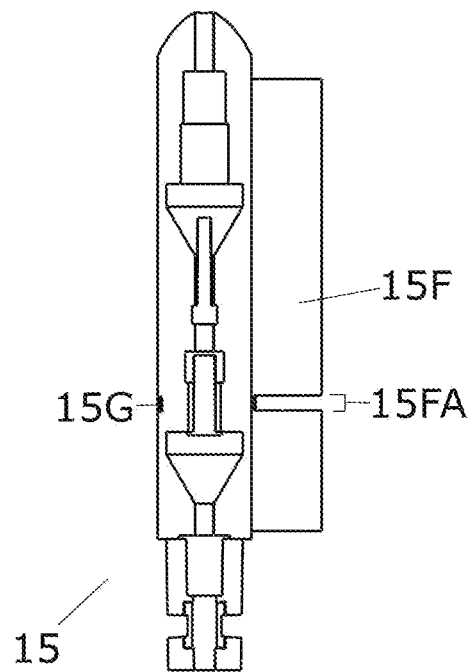
FIG. 36D illustrates a back view of a shaft member 15 according to an embodiment, and when the shaft 17 of the device 10 is at its maximum girth size.

Preferably, the shaft member 15 is made of a rigid material such as but not limited to: plastic and/or metal, however, the shaft member 15 may be made in combination with a semi-rigid and/or a soft material such as but not limited to: silicone and/or rubber to reduce the impact with the body orifice during the utilization of the device 10. The shaft member 15 when made of metal, may be magnetized to increase the blood flow, relaxes muscles and ligaments of the body orifice region and therefore enhance the dilation and stretch of the body orifice during the utilization of the device 10. FIG. 31A illustrates a front view of one shaft member 15 in one embodiment. FIG. 31B illustrates a back view of one shaft member 15 in one embodiment. FIG. 310 illustrates a top view of one shaft member 15 in one embodiment. FIG. 31D illustrates a section view of FIG. 31O. FIG. 32O illustrates a front view of one shaft member 15 in one embodiment. FIG. 32D illustrates a side view of one shaft member 15 in one embodiment. FIG. 33A illustrates a perspective view of the device 10 with the shaft 17 at its minimum girth size according to an embodiment of the device 10 (sheath 16 not illustrated in FIG. 33A). FIG. 33B illustrates a perspective view of the device 10 with the shaft 17 at its maximum girth size according to an embodiment of the device 10 (sheath 16 not illustrated in FIG. 33B).

Figure 32B:
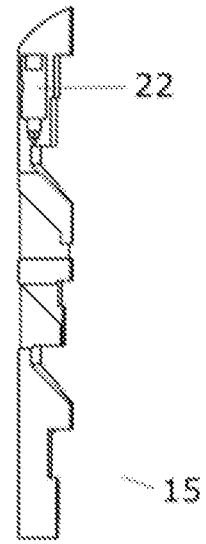
FIG. 32B illustrates a section view of FIG. 32A.
Figure 32C:
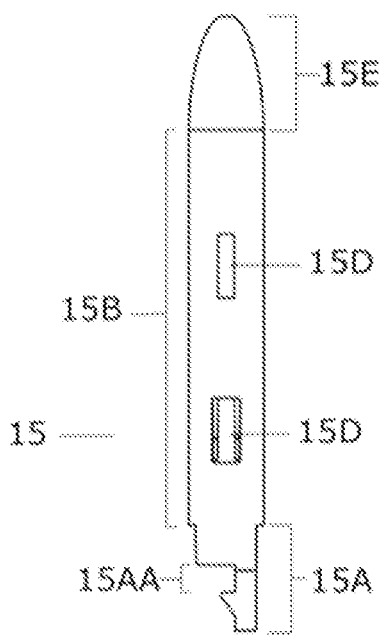
FIG. 32C illustrates a front view of a shaft member 15 according to an embodiment.

In another embodiment, at least one shaft member 15 may comprise at least one: an electronic part 18, a vibration motor 22 (as illustrated in FIG. 32B), a heating element (not illustrated), an electrical stimulation electrode (not illustrated), and/or a heart rate monitor (not illustrated). This embodiment provides others features that enhance the body orifice dilation and stretch procedure for the user during the utilization of the device 10.

In another embodiment, as illustrated in FIG. 34 and FIG. 35, at least one shaft member 15 may comprise at least one side extension 15F. The side extension 15F slidably connects the following shaft member 15 around the longitudinal axis of the threaded shaft 13 (as illustrated in FIG. 35). Attention being called to the fact that this embodiment enhances the repartition of the pressure generated against the entire lateral surface area of the body orifice when the girth size of the shaft 17 is increased and decreased by the user. Preferably, the side extension 15F is made of a semi-rigid and resilient material such as but not limited to: plastic. Preferably, the side extension 15F is made with the shaft member 15 when the shaft member 15 is made of plastic, however, the side extension 15F may be made separately and secured to the shaft member 15. FIG. 34A illustrates a front view of the shaft member 15 having at least one side extension 15F in its original shape, when the shaft 17 of the device 10 is at its minimum girth size. FIG. 34B illustrates a back view of the shaft member 15 having at least one side extension 15F in its original shape, when the shaft 17 of the device 10 is at its minimum girth size. FIG. 34C illustrates a front view of the shaft member 15 having at least one side extension 15F deformed elastically from its original shape, when the shaft 17 of the device 10 is at its maximum girth size. FIG. 34O illustrates a back view of the shaft member 15 having at least one side extension 15F deformed elastically from its original shape, when the shaft 17 of the device 10 is at its maximum girth size. FIG. 35A illustrates a front view of the device 10 with the shaft 17 at its minimum girth size in this embodiment (sheath 16 not illustrated). FIG. 35B illustrates a front view of the device 10 with the shaft 17 at its maximum girth size in this embodiment (sheath 16 not illustrated). FIG. 35C illustrates a top view of the device 10 with the shaft 17 at its minimum girth size in this embodiment (sheath 16 not illustrated). FIG. 35O illustrates a top view of the device 10 with the shaft 17 at its maximum girth size in this embodiment (sheath 16 not illustrated).

Figure 37A:
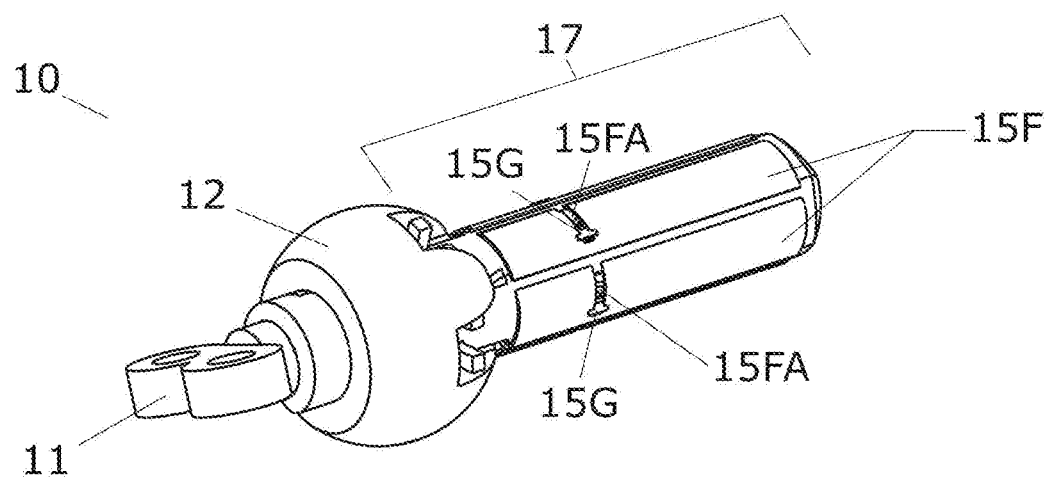
FIG. 37A is a perspective view of the device 10 with the shaft 17 at its minimum girth size according to an embodiment of the device 10 (sheath 16 not illustrated)
Figure 37B:
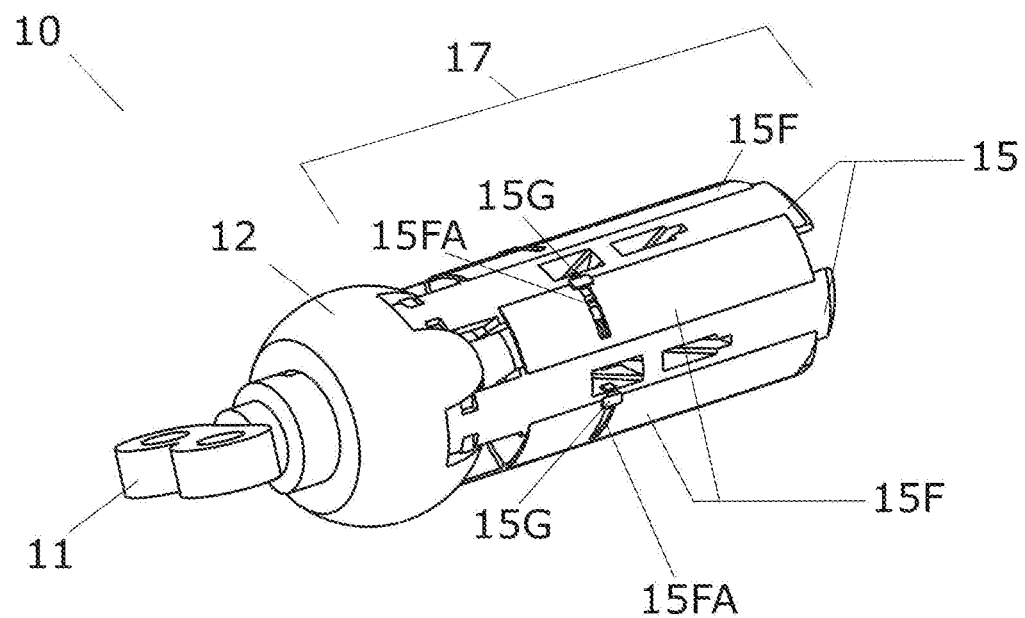
FIG. 37B is a perspective view of device 10 with the shaft 17 at its maximum girth the according to an embodiment of the device 10 (sheath 16 not illustrated).

In another embodiment as illustrated in FIG. 36 and FIG. 37, a plurality of shaft members 15 may comprise at least one side extension 15F having at least one groove 15FA, and at least one side extension groove connector 15G. The side extension groove connector 15G of one shaft member 15 having at least one side extension 15F having at least one groove 15FA, and at least one side extension groove connector 15G is configured to slidably fit into the groove 15FA of the previous shaft member 15 having at least one side extension 15F having at least one groove 15FA and at least one side extension groove connector 15G, around the longitudinal axis of the threaded shaft 13. The interaction between a groove 15FA of one shaft member 15 slidably connected to a side extension groove connector 15G of another shaft member 15, facilitates the travel of each shaft member of a plurality of shaft members 15 perpendicularly to the longitudinal axis of the threaded shaft 13, in the opposite direction of the longitudinal axis of the threaded shaft 13 when the girth size of the shaft 17 is increased by the user, and in the direction of the longitudinal axis of the threaded shaft 13 when the girth size of the shaft 17 is decreased by the user. Preferably, the side extension groove connector 15G is made with the shaft member 15, however, the side extension groove connector 15G may be made separately and be secured to the shaft member 15. In that case, the side extension groove connector 15G is preferably made of such as but not limited to: plastic and/or metal. FIG. 36A illustrates a front view of the shaft member 15 having at least one side extension 15F having at least one groove 15FA in its original shape, and at least one side extension groove connector 15G, when the shaft 17 of the device 10 is at its minimum girth size. FIG. 36B illustrates a back view of the shaft member 15 having at least one side extension 15F having at least one side extension groove 15FA in its original shape, and at least one side extension groove connector 15G, when the shaft 17 of the device 10 is at its minimum girth size. FIG. 36O illustrates a front view of the shaft member 15 having at least one side extension 15F having at least one groove 15FA deformed elastically from its original shape, and at least one side extension groove connector 15G, when the shaft 17 of the device 10 is at its maximum girth size. FIG. 36D illustrates a back view of the shaft member 15 having at least one side extension 15F having at least one groove 15FA deformed elastically from its original shape, and at least one side extension groove connector 15G, when the shaft 17 of the device 10 is at its maximum girth size. FIG. 37A illustrates a perspective view of the device 10 with the shaft 17 at its minimum girth size in this embodiment (sheath 16 not illustrated). FIG. 37B illustrates a perspective view of the device 10 with the shaft 17 at its maximum girth size in this embodiment (sheath 16 not illustrated).

In another embodiment as illustrated in FIG. 38A, at least one shaft member 15 may comprise at least one shaft member orifice stimulation protrusion 15H. The shaft member orifice stimulation protrusion 15H stimulates the body orifice through the sheath 16, during the utilization of the device 10. The shaft member orifice stimulation protrusion 15H may also be configured to prevent undesired expulsions of the device 10 from the body orifice during the utilization. It also has to be understood that two shaft member orifice stimulation protrusions 15H located one after another along the shaft member 15 will create a space similar to a channel and/or a groove between the two shaft member orifice stimulation protrusions 15H. This space created by both shaft member orifice stimulation protrusions 15H may be part of the configuration that prevent undesired expulsions of the device 10 from the body orifice during the utilization by allowing one or several parts of the body orifice being trapped between the two shaft member orifice stimulation protrusions 15H. In this embodiment the module connector groove 15O and/or the module cavity 15C with a sloped edge 15CA may be configured to pass through totally or not into shaft member orifice stimulation protrusion 15H. This embodiment provides others features that enhance the body orifice dilation and stretch procedure for the user during the utilization of the device 10.

In another embodiment (not illustrated), the shaft member 15 may comprise at least one shaft spring (not illustrated).

Preferably, the shaft spring is such as but not limited to: a tensile spring, a circular spring, a circular spring clamp and/or a circular spring clamp clip made of such as but not limited to: metal or plastic. Preferably, the shaft spring connects a plurality of shaft members 15 together, and/or at least one shaft member 15 to the housing 12, and/or at least one shaft member 15 to at least one module 14 (or a plurality of modules 14). The shaft spring facilitates the travel of at least one shaft member 15, or each shaft member 15 of a plurality of shaft members 15 perpendicularly to the longitudinal axis of the threaded shaft 13, in the direction of the longitudinal axis of the threaded shaft 13, when the girth size of the shaft 17 is decreased by the user, and reinforces the global structure of the device 10.

Sheath

In a preferred embodiment, the device 10 comprises one sheath 16. In a preferred embodiment, a sheath 16 has a first end 16A, a middle section 16B, a tip end 16O, and a sheath girth as illustrated in FIG. 1. In a preferred embodiment the sheath 16 is configured to surround the plurality of shaft members 15, however, in another preferred embodiment, the first end 16A of the sheath 16 may be configured to surround partially the housing 12 (as illustrated in FIG. 1A, FIG. 1B, FIG. 39A, and FIG. 39B) or the entire housing 12 (as illustrated in FIG. 39C and FIG. 39D). FIG. 1A is a front view of the device 10 with the shaft 17 at its minimum girth size according to a preferred embodiment of the device 10. FIG. 1B is a front view of the device 10 with the shaft 17 at its maximum girth size according to a preferred embodiment of the device 10. FIG. 39A is a front view of the device 10 with the shaft 17 at its minimum girth size according to a preferred embodiment of the device 10. FIG. 39B is a front view of the device 10 with the shaft 17 at its maximum girth size according to a preferred embodiment of the device 10. FIG. 39C is a front view of the device 10 with the shaft 17 at its minimum girth size to a preferred embodiment of the device 10. FIG. 39D is a front view of the device 10 with the shaft 17 at its maximum girth size to a preferred embodiment of the device 10.

Preferably, the sheath 16 is made of a soft and resilient material such as but not limited to: silicone and/or rubber. Preferably, the sheath 16 is made with at least one coloration additive, however, the sheath 16 may be made with no coloration additive. The sheath 16 may comprise at least one additive such as but not limited to: a perfume additive, a fluorescent additive, a glowing additive or a conductive additive. This additive provides others features that enhance the body orifice dilation and stretch procedure for the user during the utilization of the device 10. The sheath 16 may be configured with a color code and/or a serial number to distinguish a device 10 from another device 10 to facilitate the utilization for the user of several devices 10 (having or not the same features). The sheath 16 may be configured with at least one visual and/or tactile indication to indicate to the user how to use the device 10. Preferably, the sheath 16 is secured to the plurality of shaft members 15 and/or the housing 12, however, the sheath 16 may be configured to be removably secured to the plurality of shaft members 15 or the plurality of shaft members 15 and the housing 12, which means that the sheath 16 may be repeatedly: secured to the plurality of shaft members 15 or the plurality of shaft members 15 and the housing 12, then removed from the plurality of shaft members 15 or the plurality of shaft members 15 and the housing 12, and then secured again to the plurality of shaft members 15 or the plurality of shaft members 15 and the housing 12. Preferably, the length of the sheath 16, from the first end 16A to the tip end 16C is greater than 1 inch. Preferably, the girth size of the sheath girth of the sheath 16 is greater than 1.28 inch, when the shaft 17 of the device 10 is at its minimum girth size. The girth size of the sheath girth is calculated using the lateral surface area of the cylinder shape formed at the middle section 16B of the sheath 16. The direction of rotation of the controller 11 when the user rotates the controller 11 in one direction clockwise or counter-clockwise, to increase the girth size of the shaft 17 and therefore increase the girth size of the sheath girth of the sheath 16 is referred to as the «the direction of increase of the sheath girth». The direction of rotation of the controller 11 when the user rotates the controller 11 in one direction clockwise or counter-clockwise, to decrease the girth size of the shaft 17 and therefore decrease the girth size of the sheath girth of the sheath 16 is referred to as the «the direction of decrease of the sheath girth». Preferably, the tip end 16C closes the device 10 as illustrated in FIG. 1C and FIG. 1D.

Figure 40A:
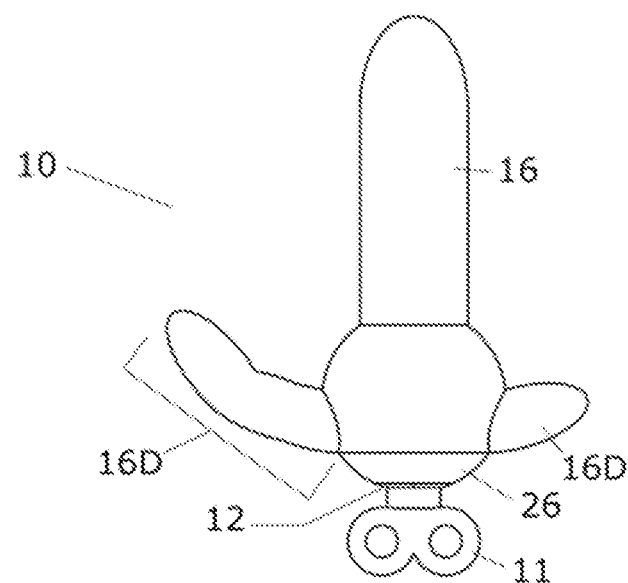
FIG. 40A illustrates a front view of the device 10 with the shaft 17 at its minimum girth size according to an embodiment of the device 10.
Figure 40B:
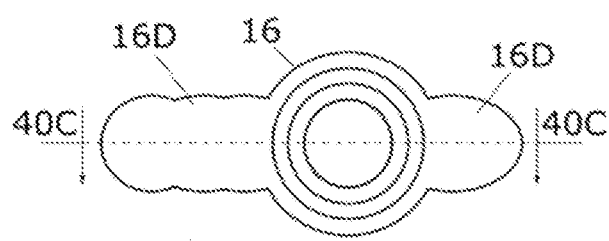
FIG. 40B illustrates a bottom view of the sheath 16 according to an embodiment.
Figure 40C:
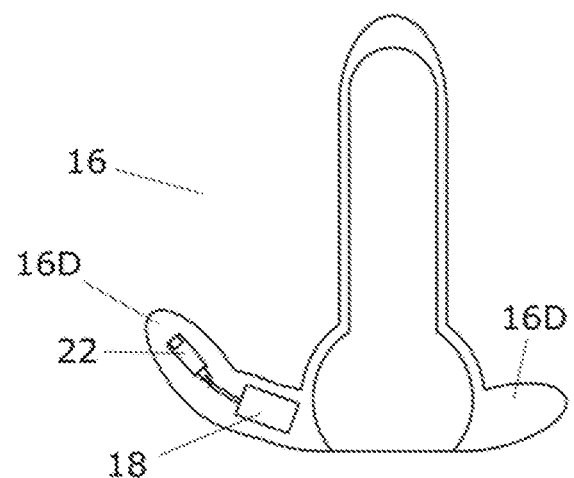
FIG. 40C illustrates a section view of FIG. 40B.
Figure 41:
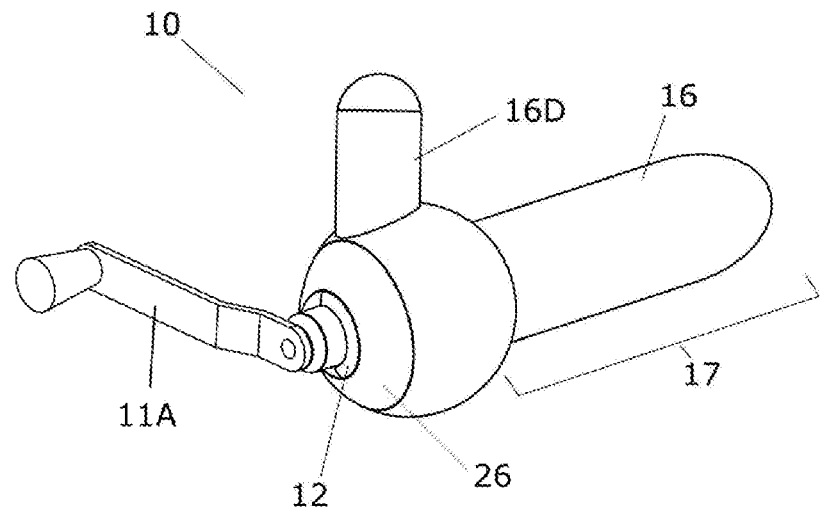
FIG. 41 illustrates a perspective view of the device 10 with the shaft 17 at its minimum girth size according to an embodiment of the device 10.

In another embodiment, as illustrated in FIG. 40 and FIG. 41, the sheath 16 may comprise at least one sheath external protrusion 16D. The sheath external protrusion 16D prevents the device 10 to rotate inside the body orifice when the user performs the adjustment of the device 10, by pressing against the nearest body part of the body orifice where the shaft 17 of the device 10 is inserted. The sheath external protrusion 16D is also a handle to enhance the utilization of the device 10. The sheath external protrusion 16D may comprise at least one: an electronic part 18 (illustrated in FIG. 40C), a vibration motor 22 (illustrated in FIG. 40C), a heating element (not illustrated), a heart rate monitor (not illustrated), an electrical stimulation electrode (not illustrated), a penis ring (not illustrated), a weight 32 (not illustrated in this embodiment), and/or a girth adjustment indicator 23 (not illustrated in this embodiment). The sheath external protrusion 16D also prevents over-insertion of the device 10 inside the body orifice. The sheath external protrusion 16D may also be configured to stimulate by contact another body part (such as a vagina when the device 10 is inserted into a female anus) to enhance the body orifice dilation procedure during the utilization of the device 10, The sheath external protrusion 16D may also be configured to stimulate another body orifice by being inserted into it (such as a vagina when the device 10 is inserted into an anus) to enhance the body orifice dilation procedure during the utilization of the device 10. The sheath external protrusion 16D is preferably made with the sheath 16, however, the sheath external protrusion 16D may be made separately and configured to be removably secured to the sheath 16, which means that sheath external protrusion 16D may be repeatedly: secured to the sheath 16, then removed from the sheath 16, and then secured again to the sheath 16. In that case, the sheath external protrusion 16D is preferably made of a rigid material such as but not limited to: plastic, however, the external protrusion 16D may be made of a semi-rigid material such as but not limited to: plastic, silicone, and/or rubber, or the external protrusion 16D may be made of a rigid material in combination with a semi-rigid and/or a soft material such as but not limited to: silicone, leather, and/or rubber. This embodiment provides others features that enhance the body orifice dilation and stretch procedure for the user during the utilization of the device 10.

Figure 42:
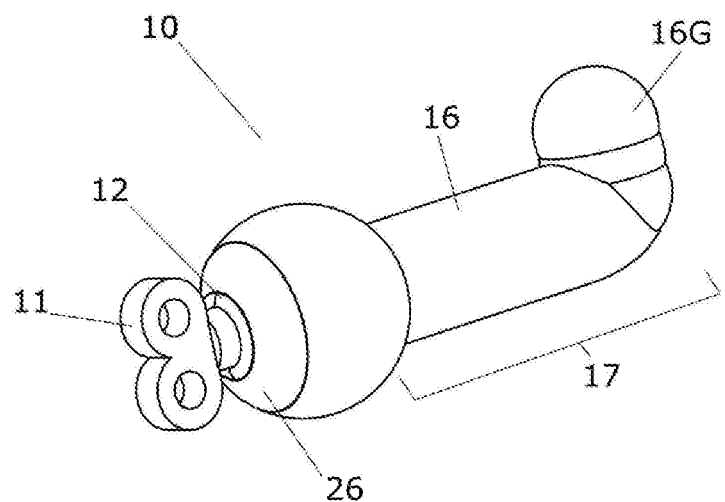
FIG. 42 illustrates a perspective view of the device 10 with the shaft 17 at its minimum girth size according to an embodiment of the device 10.

In another embodiment, as illustrated in FIG. 42, the device 10 may comprise at least one prostate stimulation protrusion 16G. The prostate stimulation protrusion 16G stimulates the prostate via the anal body orifice, during the utilization of the device 10 (for example in a male anus body orifice). This embodiment provides others features that enhance the body orifice dilation and stretch procedure for the user during the utilization of the device 10.

In another embodiment, the sheath 16 may comprise at least one: an electronic part 18 as illustrated in FIG. 50, a vibration motor 22, a girth adjustment indicator 23 (not illustrated in this embodiment), a heating element (not illustrated), a heart rate monitor (not illustrated), an electrical stimulation electrode (not illustrated), a penis ring (not illustrated), and/or a weight 32 (not illustrated in this embodiment). This embodiment provides others features that enhance the body orifice dilation and stretch procedure for the user during the utilization of the device 10.

Figure 48:
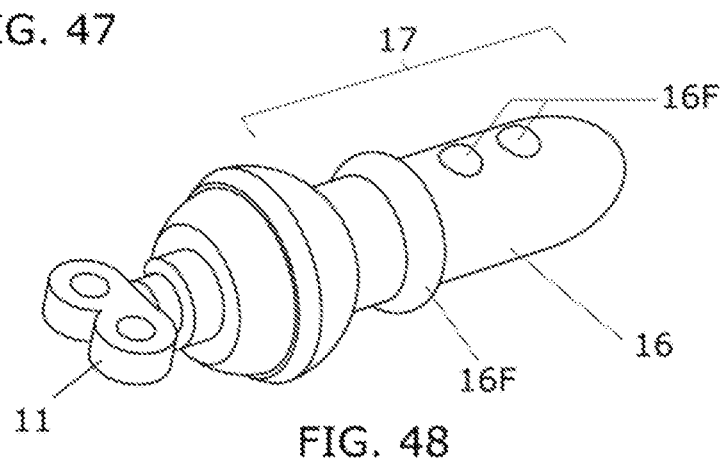
FIG. 48 illustrates a perspective view of the device 10 with the shaft 17 at its minimum girth size according to an embodiment of the device 10.

In another embodiment, as illustrated in FIG. 48, the sheath 16 may comprise at least one sheath orifice stimulation protrusion 16F. The sheath orifice stimulation protrusion 16F stimulates the body orifice, during the utilization of the device 10 by the user. As illustrated in FIG. 48, the sheath orifice stimulation protrusion 16F may also be configured to prevent undesired expulsion of the device 10 from the body orifice during the utilization. It also has to be understood that two sheath orifice stimulation protrusions 16F located one after another along the sheath 16 will create a space similar to a channel and/or a groove between the two sheath orifice stimulation protrusions 16F. This space created by both sheath orifice stimulation protrusions 16F may be part of the configuration that prevent undesired expulsions of the device 10 from the body orifice during the utilization by allowing one or several parts of the body orifice being trapped between the two sheath orifice stimulation protrusion 16F.

In another embodiment (not illustrated), the sheath 16 may comprise at least one longitudinal protrusion. The length of the longitudinal protrusion may be shorter or approximatively or exactly the same as the length of shaft 17 and follows the longitudinal axis of the threaded shaft 13. The longitudinal protrusion minimizes the sensation of gap between two following shaft members 15 around the longitudinal axis of the threaded shaft 13, not configured with at least one side extension 15F when the girth size of the sheath girth increases, due to the fact that a space is created between each shaft member 15 when the girth size of the sheath girth increases.

Figure 59B:
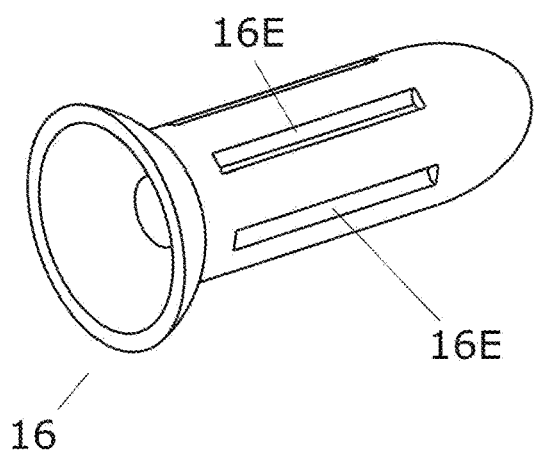
FIG. 59B illustrates a perspective view of the sheath 16 according to an embodiment of the device 10.

In another embodiment, as illustrated in FIG. 59B, the sheath 16 may comprise at least one liquid channel 16E. When the user uses a lubricant with the device 10, the liquid channel 16E retains the lubricant longer on the sheath 16 of device 10, and ensures a longer lubrication of the body orifice to make the utilization of the device 10 more comfortable.

Electronic Part

In another embodiment, the device 10 may comprise at least one electronic part 18 having at least one electric component such as but not limited to: an electric battery (single-use or rechargeable multiple times by wire and/or wireless charging), an electronic circuit, a printed circuit board, a microprocessor, an encoder, a rotation sensor, a transmitter, a receiver, a light-emitting diode (LED), a timer, an electric speaker, an electrical wire and an electronic controller such as but not limited to: a knob, a push-button, a switch and/or a tactile switch. The electronic part 18 may be configured to power, configure and/or operate by wire and/or wireless connection, elements such as but not limited to: an enclosed electric motor 19, a vibration motor 22, a girth adjustment indicator 23, a heating element (not illustrated), a heart rate monitor (not illustrated) and/or an electrical stimulation electrode (not illustrated). The electronic part 18 may be configured with predetermined operative functions, such as but not limited to: varying angles of rotation around the longitudinal axis of the threaded shaft 13 of the motor shaft of the motor having a motor shaft 19A, varying speeds of rotation of the motor shaft of the motor having a motor shaft 19A, varying rotations of the motor shaft of the motor having a motor shaft 19A, varying configurations of operation of at least one: a vibration motor 22, a girth adjustment indicator 23, a heating element (not illustrated), a heart rate monitor (not illustrated) and/or an electrical stimulation electrode (not illustrated), to provide features that enhance the body orifice dilation and stretch procedure for the user such as but not limited to: massage, stimulation, body information and/or operation information. The electronic part 18 may be configured with data storage functions, such as but not limited to: frequency of utilization of the device 10, one or various user preferences, and memory of the operation of the device 10. The electronic part 18 may be configured to indicate to the user (by sound and/or visually) one and/or various information such as but not limited to: state of charge of an electric battery, state of operation and state of configuration of an enclosed electric motor 19, an vibration motor 22, an girth adjustment indicator 23, an heating element (not illustrated), an heart rate monitor (not illustrated) and/or an electrical stimulation electrode (not illustrated). The electronic part 18 is preferably secured to the device 10, however, the electronic part 18 (or at least one of its components) may be configured to be removably secured to the device 10, which means that the electronic part 18 (or at least one of its components) may be repeatedly: secured to the device 10, then removed from the device 10, and then secured again to the device 10. The electronic part 18 may be operated by the user via such as but not limited to: an electronic controller, by voice, and/or via a computer program (not illustrated) designed to run on a desktop computer and/or a mobile device such as but not limited to: a mobile phone, and/or a mobile computing device.

Enclosed Electric Motor

In another embodiment, the device 10 may comprise an enclosed electric motor 19 having at least one motor having a motor shaft 19A, a motor housing 19B, as illustrated in FIG. 10, FIG. 11, FIG. 15, FIG. 16 and FIG. 17. The motor having a motor shaft 19A is powered, configured and/or operated via an electronic part 18. The enclosed electric motor 19 may comprise at least one planetary gear system 19C (as illustrated in FIG. 15) to change the speed of rotation of the motor shaft of the motor having a motor shaft 19A, and/or change the torque of the motor having a motor shaft 19A. The motor housing 19B may be secured to the housing 12, or removably secured to the housing 12, which means that the motor housing 19B may be repeatedly: secured to the housing 12, then removed from the housing 12, and then secured again to the housing 12. The motor shaft of the motor having a motor shaft 19A of the enclosed electric motor 19 is preferably secured to the first end 11A of the controller 11, however, the motor shaft of the motor having a motor shaft 19A may be removably secured to the first end 11A of the controller 11, which means that the motor shaft of the motor having a motor shaft 19A may be repeatedly: secured to the first end 11A of the controller 11, then removed from the first end 11A of the controller 11, and then secured again to the first end 11A of the controller 11. The motor housing 19B is preferably made of a rigid material such as but not limited to: plastic, hard rubber, metal, glass and/or wood material, however, the motor housing 19B may be made of a semi-rigid material such as but not limited to: plastic, silicone, and/or rubber, or the motor housing 19B may be made of a rigid material in combination with a semi-rigid and/or a soft material such as but not limited to: silicone, leather, and/or rubber.

Vibration Motor

In another embodiment, the device 10 may comprise at least one vibration motor 22. The vibration motor 22 preferably is such as but not limited to: an eccentric rotating mass vibration (ERM) type or a linear resonant actuator (LRA) type. The vibration motor 22 is powered, configured and/or operated via an electronic part 18. The vibration motor 22 may be configured to perform low, medium and/or high amplitude and low, medium and/or high frequency vibrations and may be configured to perform substantially noiselessly. The vibrations made by the vibration motor 22 while operated stimulate muscles and ligaments of the body orifice region and therefore enhance the dilation and stretch of the body orifice during the utilization of the device 10.

Girth Adjustment Indicator

Figure 56A:
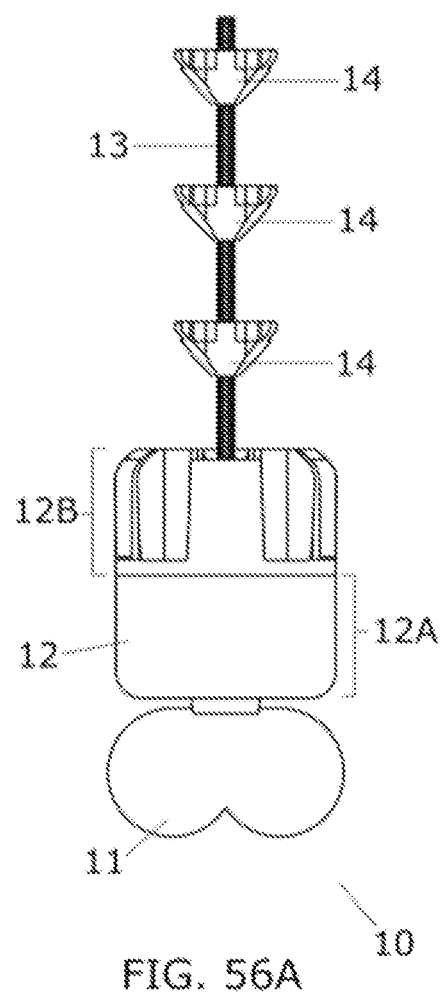
FIG. 56A illustrates a front view of the device 10 with the shaft 17 at its minimum girth size according to an embodiment of the device 10 (plurality of shaft members 15 and sheath 16 not illustrated not illustrated).
Figure 56B:
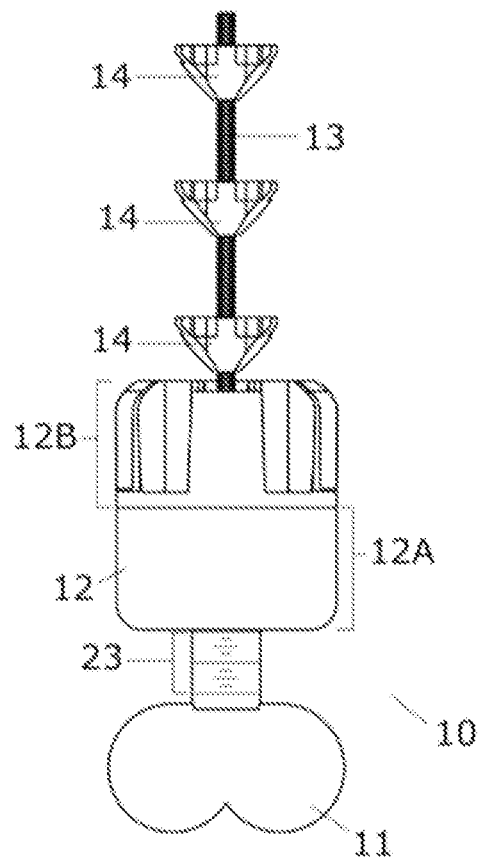
FIG. 56B illustrates a front view of the device 10 with the shaft 17 at its maximum girth size according to an embodiment of the device 10 (plurality of shaft members 15 and sheath 16 not illustrated).
Figure 56C:
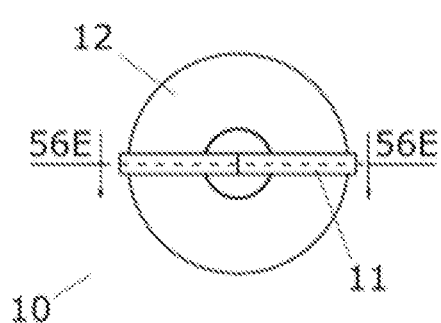
FIG. 56C illustrates a bottom view of FIG. 56A.
Figure 56D:
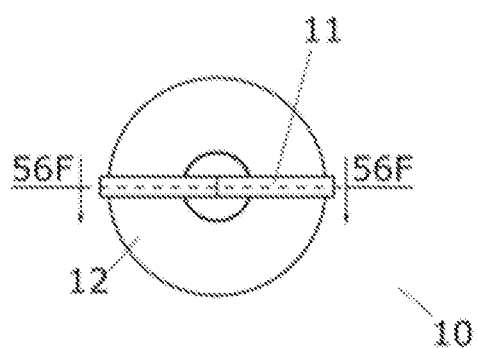
FIG. 56D illustrates a bottom view of FIG. 56B.
Figure 56E:
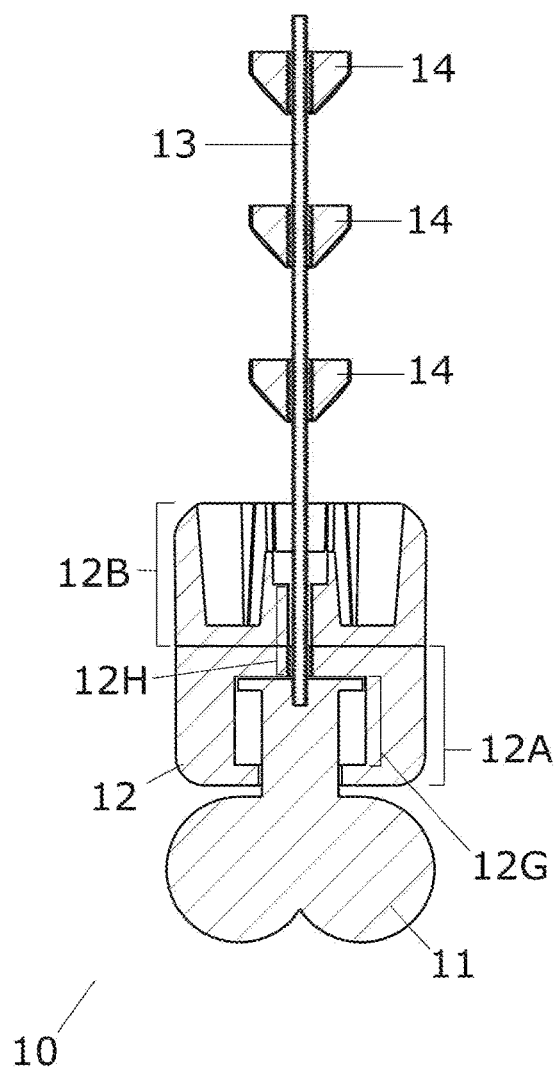
FIG. 56E illustrates a section view of FIG. 56C.
Figure 56F:
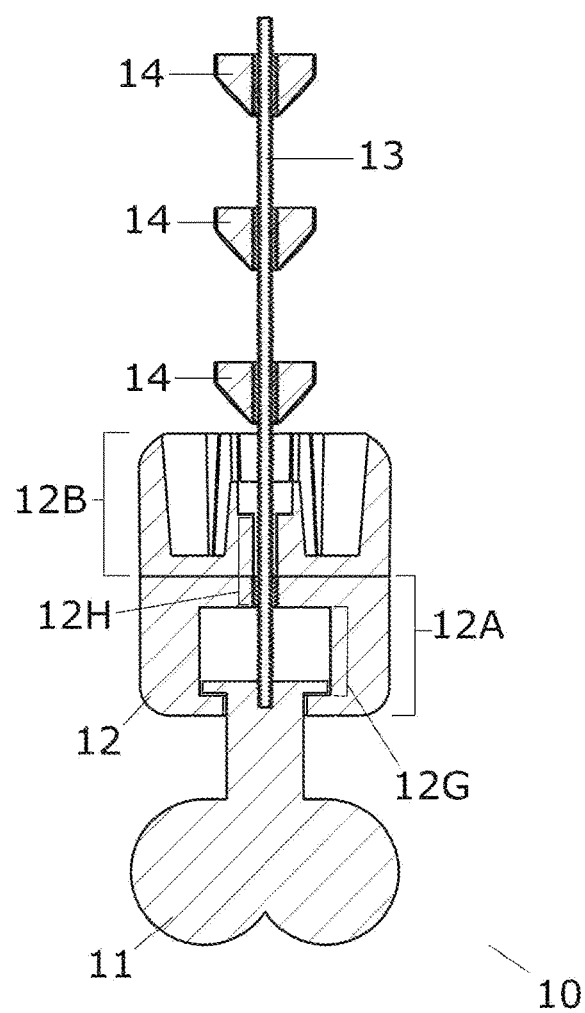
FIG. 56F illustrates a section view of FIG. 56D.

In another embodiment, the device 10 may comprise at least one girth adjustment indicator 23. The girth adjustment indicator 23 indicates by sound, in a tactile manner, and/or visually to the user, the state of the girth and/or limits of the adjustment of the device 10. Preferably, the girth adjustment indicator 23 is such as a mechanical type (as illustrated in FIG. 29B and FIG. 56B), meaning that it does not require any electronic component and power supply to be functional, however, the girth adjustment indicator 23 may be electronical type, meaning that it does require at least one electronic component to be functional. In the case that the girth adjustment indicator 23 is electronical type, the girth adjustment indicator 23 is powered, configured and/or operated via an electronic part 18.

Heating Element

In another embodiment the device 10 may comprise at least one heating element (not illustrated). The heating element converts energy received from the electronic part 18 into heat. The heating element transfers heat to the skin of the body orifice where the device 10 is inserted (directly or via the sheath 16, when preferably the sheath 16 comprises a conductive additive). The heating element is preferably such as but not limited to: an electrical heating element or a polymer PTC heating element. The heating element is powered, configured and/or operated via an electronic part 18. The heat made by the heating element while operated stimulates muscles and ligaments of the body orifice region and therefore enhances the dilation and stretch of the body orifice during the utilization of the device 10.

Heart Rate Monitor

In another embodiment the device 10 (not illustrated) may comprise at least one heart rate monitor. The heart rate monitor may comprise at least one component such as but not limited to: a transmitter, and/or a receiver, such that when a heartbeat and/or changes in blood flow of the body of the body orifice where the device 10 is inserted is detected by the transmitter, a signal is transmitted (by electrical wire, by wireless technology, and/or by low-power radio link) to the receiver to determine the current heart rate. The heart rate monitor may be configured with a light-emitting diode (LED) to measure changes in blood flow through the skin. The heart rate monitor may be configured to measures in real time such as but not limited to: heart rate, pulse, and/or oxygen saturation, of the body of the body orifice where the device 10 is inserted during the utilization. The heart rate monitor is powered, configured and/or operated via an electronic part 18. This embodiment provides control features that enhance the body orifice dilation and stretch procedure for the user during the utilization of the device 10.

Electrical Stimulation Electrode

In another embodiment the device 10 may comprise at least one electrical stimulation electrode. The electrical stimulation electrode delivers electric impulses generated by the electronic part 18 in the skin of the body orifice where the device 10 is inserted (directly or via the sheath 16, when preferably the sheath 16 comprises a conductive additive). The electrical stimulation electrode is powered, configured and/or operated via an electronic part 18. This embodiment provides others features that enhance the body orifice dilation and stretch procedure for the user, such as but not limited to: pelvic floor physical therapy.

Weight

In another embodiment, the device 10 may comprise at least one weight 32 (as illustrated in FIG. 29B). The weight 32 has preferably a weight greater than or equal to 0.07 ounce. This embodiment provides others features that enhance the body orifice dilation and stretch procedure for the user, such as but not limited to: pelvic floor physical therapy. FIG. 29B illustrates a part of the housing 12 in this embodiment.

Penis Ring

In another embodiment the device 10 may comprise at least one penis ring (not illustrated). The penis ring is preferably secured to the device 10, however, the penis ring may be configured to be removably secured to the device 10, which means that the penis ring may be repeatedly: secured to the device 10, then removed from the device 10, and then secured again to the device 10. The penis ring is preferably made of a rigid material such as but not limited to: plastic, hard rubber, metal, glass and/or wood, however, the penis ring may be made of a semi-rigid material such as but not limited to: plastic, silicone, and/or rubber, or the penis ring may be made of a rigid material in combination with a semi-rigid and/or a soft material such as but not limited to: silicone, leather, and/or rubber. Preferably, the penis ring is made with at least one coloration additive, however, the penis ring may be made with no coloration additive. The penis ring may be configured with a color code and/or a serial number to distinguish a device 10 from another device 10 to facilitate the utilization for the user of several devices 10 (having or not the same features). The penis ring provides others features that enhance the body orifice dilation and stretch procedure for the user such as but not limited to: a restriction of the flow of blood from the erect penis in order to produce a stronger erection or to maintain an erection for a longer period of time, and/or a ring to hold via the penis, the device 10 inside a body orifice to prevent undesired movement of the device 10 during the utilization. The penis ring may be considerate as a handle to facilitate the utilization of the device 10 and the removal from a body orifice of the device 10, and therefore useful for male and female. The penis ring may comprise: an electronic part 18, a vibration motor 22, a heating element (not illustrated), a heart rate monitor (not illustrated), an electrical stimulation electrode (not illustrated), a weight 32, and/or a girth adjustment indicator 23.

Closure Element

In another preferred embodiment, as illustrated from FIG. 39 to FIG. 43, the device 10 comprises a closure element 26. Preferably, the closure element 26 is made of a rigid material such as but not limited to: plastic, hard rubber, metal, glass and/or wood, however, the closure element 26 may be made of a semi-rigid material such as but not limited to: plastic, silicone, and/or rubber, or the closure element 26 may be made of a rigid material in combination with a semi-rigid and/or a soft material such as but not limited to: silicone, leather, and/or rubber. Preferably, the closure element 26 is configured to receive the controller 11 and be connected to the sheath 16 and/or the housing 12. The closure element 26 is preferably secured to the device 10, however, the closure element 26 may be configured to be removably secured to the device 10, which means that the closure element 26 may be repeatedly: secured to the device 10, then removed from the device 10, and then secured again to the device 10. As illustrated in FIG. 43A, the closure element 26 may comprise at least one connector 26A such as but not limited to: a cantilever snap-fit. In that case, the housing 12 and/or the sheath 16 are configured to receive the connector 26A. Preferably, the closure element 26 is made with at least one coloration additive, however, the closure element 26 may be made with coloration additive. The closure element 26 may be configured with a color code and/or a serial number to distinguish a device 10 from another device 10 to facilitate the utilization for the user of several devices 10 (having or not the same features). The closure element 26 prevents contamination such as but not limited to: dust, from entering inside the device 10. The closure element 26 may comprise an electronic part 18. The closure element 26 may also be an alternative to fix the sheath 16 to the housing 12 by pressing the sheath 16 against the housing 12. FIG. 43A illustrates a perspective view of the closure element 26 in one embodiment. FIG. 43B illustrates a perspective view of the closure element 26 in one embodiment.

Resilient Band

Figure 44A:
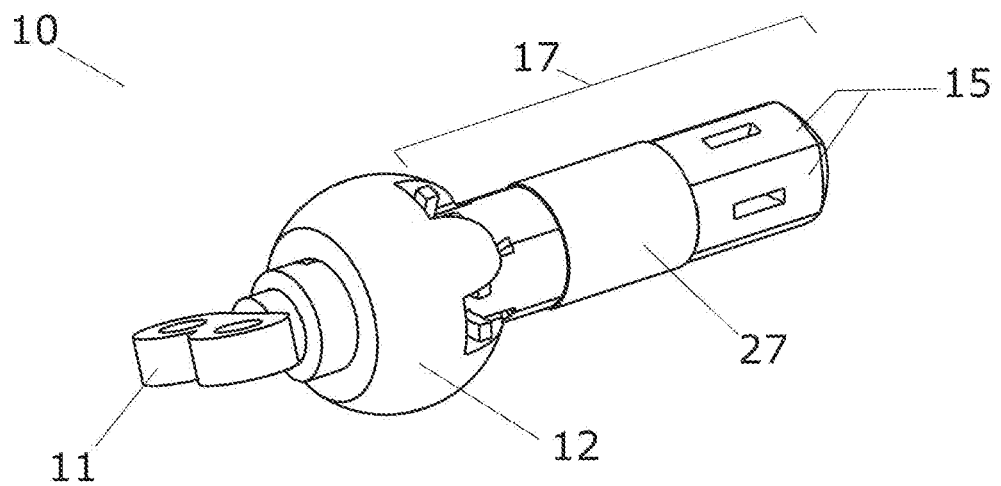
FIG. 44A illustrates a perspective view of the device 10 with the shaft 17 at its minimum girth size according to an embodiment of the device 10 (sheath 16 not illustrated).
Figure 44B:
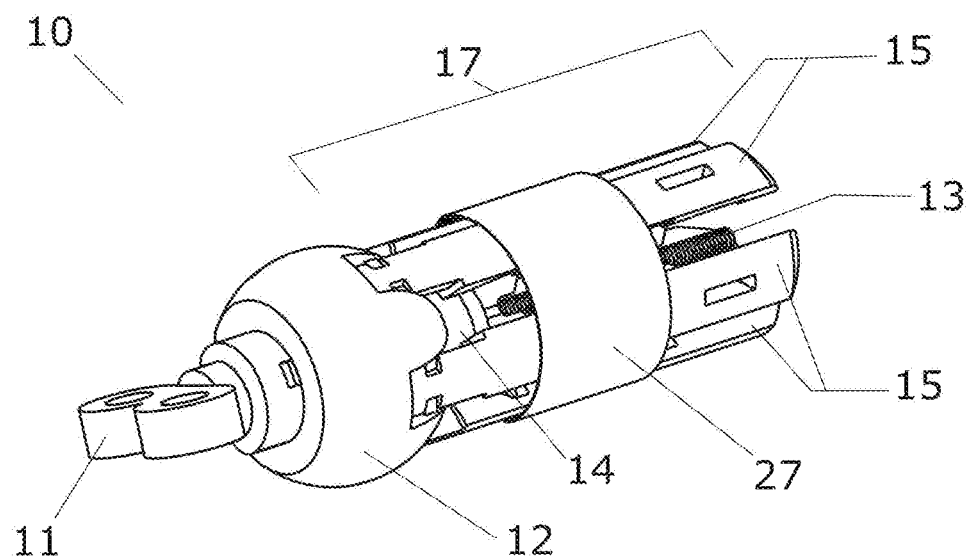
FIG. 44B illustrates a perspective view of the device 10 with the shaft 17 at its maximum girth size according to an embodiment of the device 10 (sheath not illustrated).

In another embodiment, as illustrated in FIG. 44, the device 10 may comprise at least one resilient band 27. Preferably, the resilient band 27 is made of a resilient material such as but not limited to: rubber and/or silicone. Preferably, the width of the resilient band 27 is greater than 0.05 inch. Preferably, the resilient band 27 surrounds the plurality of shaft members 15. The resilient band 27 facilitates the travel of each shaft member 15 of the plurality of shaft members 15 perpendicularly to the longitudinal axis of the threaded shaft 13, in the direction of the longitudinal axis of the threaded shaft 13, when the girth size of the shaft 17 is decreased by the user, and reinforces the global structure of the device 10.

Strap

Figure 46:
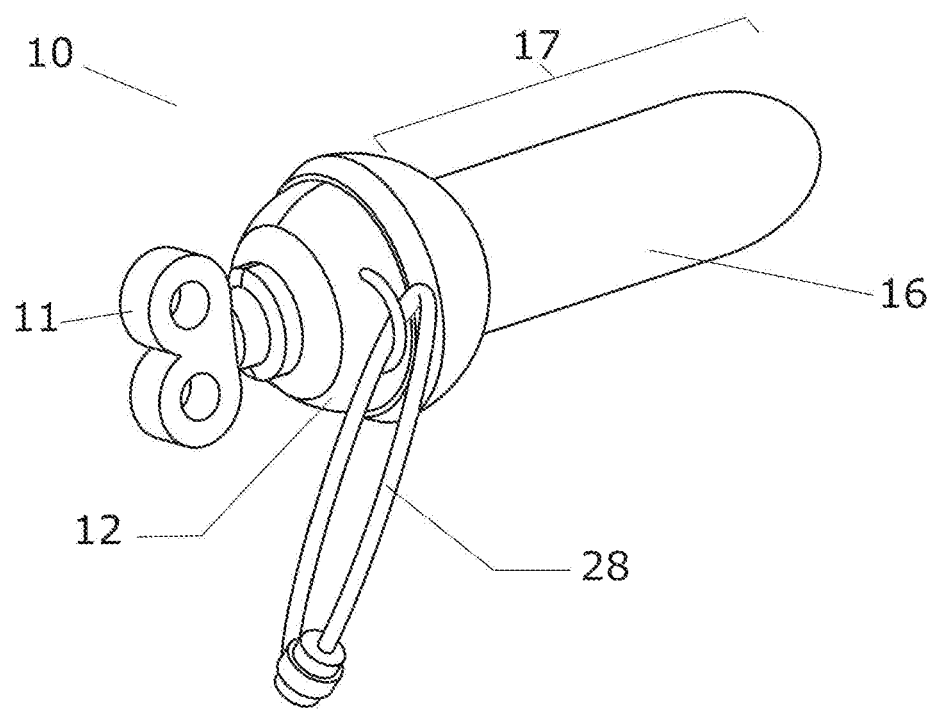
FIG. 46 illustrates a perspective view of the device 10 with the shaft 17 at its minimum girth size according to an embodiment of the device 10.
Figure 47:
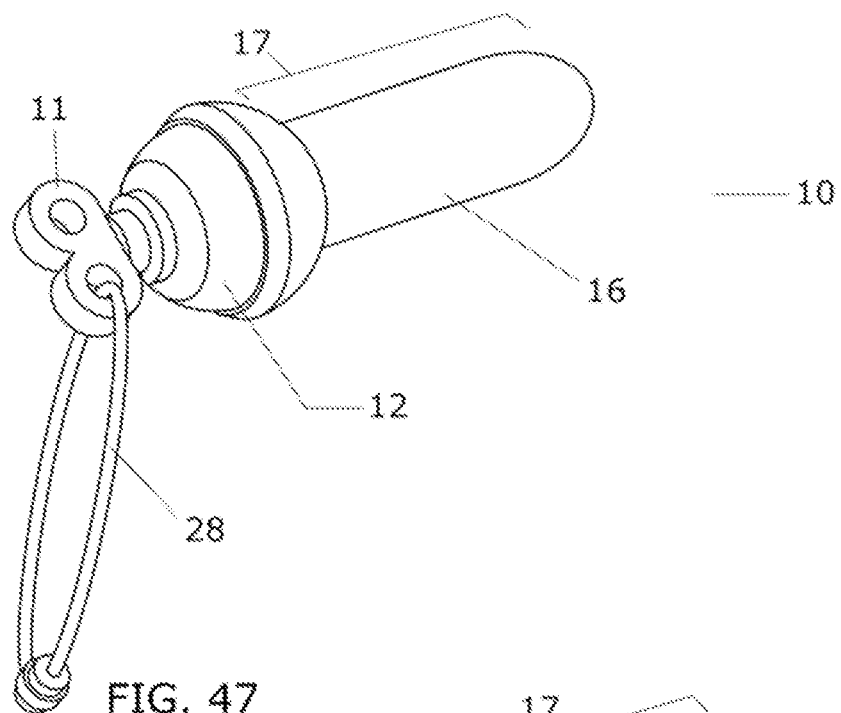
FIG. 47 illustrates a perspective view of the device 10 with the shaft 17 at its minimum girth size according to an embodiment of the device 10.

In another embodiment, the device 10 may comprise at least one strap 28, as illustrated in FIG. 46 and FIG. 47. Preferably, the strap 28 is made of such as but not limited to: plastic, silicone, rubber, leather, metal and/or wood. Preferably, the strap 28 is made with at least one coloration additive, however, the strap 28 may be made with no coloration additive. The strap 28 may be configured with a color code and/or a serial number to distinguish a device 10 from another device 10 to facilitate the utilization for the user of several devices 10 (having or not the same features). The strap 28 is preferably secured to the device 10, however, the strap 28 may be configured to be removably secured to the device 10, which means that the strap 28 may be repeatedly: secured to the device 10, then removed from the device 10, and then secured again to the device 10. The strap 28 may comprise an electronic part 18, a body skin protection element 29 and/or a grip 30. The strap 28 may be configured as a handle to facilitate the utilization of the device 10 and the removal from a body orifice of the device 10 and/or configured as a belt that the user may wear around its waist to maintain the device 10 inside a body orifice during the utilization of the device 10.

Body Skin Protection Element

Figure 49:
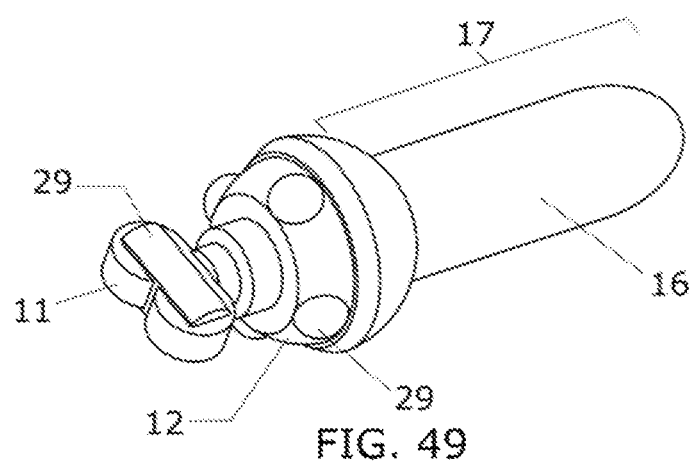
FIG. 49 illustrates a perspective view of the device 10 with the shaft 17 at its minimum girth size according to an embodiment of the device 10.

In another embodiment, the device 10 may comprise at least one body skin protection element 29, as illustrated in FIG. 49. The body skin protection element 29 is made of such as but not limited to: rubber, plastic, and/or silicone. Preferably, the body skin protection element 29 is made with at least one coloration additive, however, the body skin protection element 29 may be made with no coloration additive. The body skin protection element 29 may be configured with a color code and/or a serial number to distinguish a device 10 from another device 10 to facilitate the utilization for the user of several devices 10 (having or not the same features). The body skin protection element 29 may comprise an electronic part 18. The body skin protection element 29 prevents the discomfort of skin friction against the device 10 during the utilization of the device 10.

Grip

Figure 52:
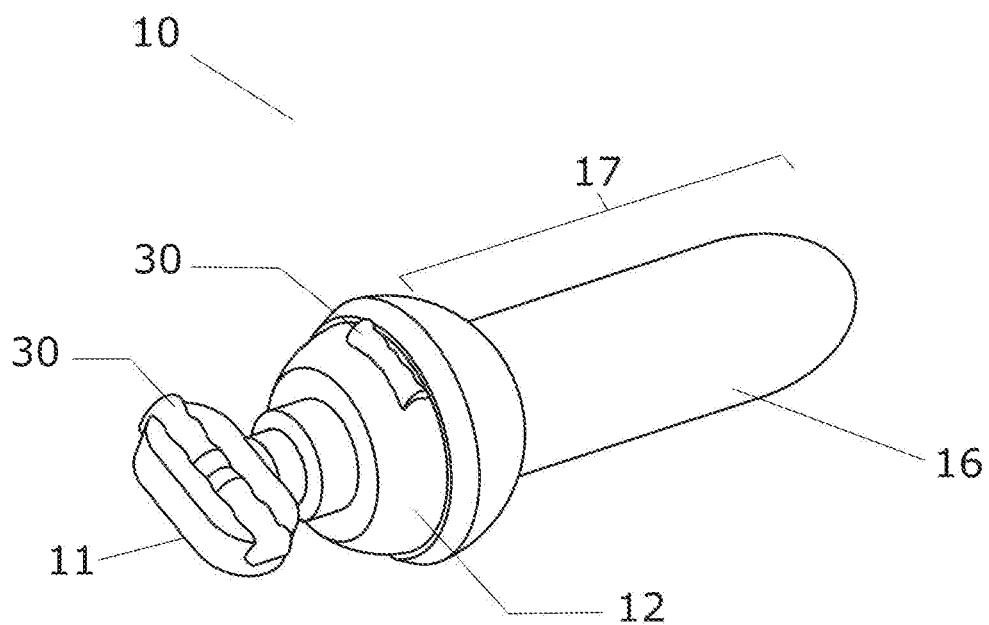
FIG. 52 illustrates a perspective view of the device 10 with the shaft 17 at its minimum girth size according to an embodiment of the device 10.

In another embodiment, the device 10 may comprise at least one grip 30, as illustrated in FIG. 52. The grip 30 is preferably made of such as but not limited to: plastic, silicone, rubber, metal and/or wood. Preferably, the grip 30 is made with at least one coloration additive, however, the grip 30 may be made with no coloration additive. The grip 30 may be configured with a color code and/or a serial number to distinguish a device 10 from another device 10 to facilitate the utilization for the user of several devices 10 (having or not the same features). The grip 30 may comprise an electronic part 18. The grip 30 enhances the grabbing of the device 10 and therefore enhances the utilization of the device 10.

Magnet

Figure 53:
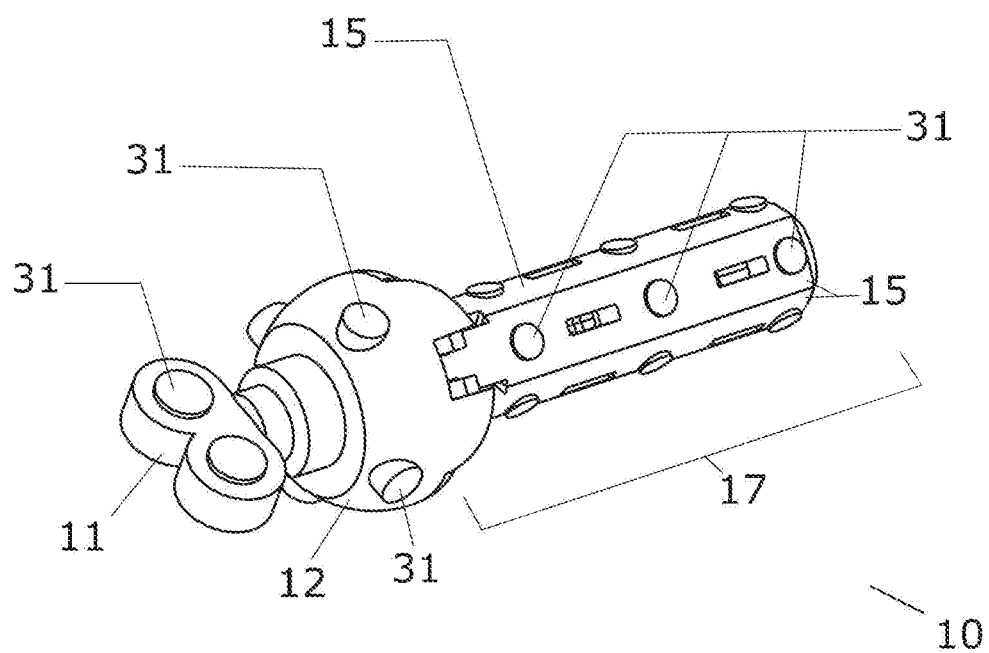
FIG. 53 illustrates a perspective view of the device 10 with the shaft 17 at its minimum girth size according to an embodiment of the device 10 (sheath 16 not illustrated).

In another embodiment, the device 10 may comprise at least one magnet 31, illustrated in FIG. 51 and FIG. 53 (sheath 16 not illustrated in FIG. 53). Preferably, the magnet 31 is such as but not limited to: a neodymium magnet. The magnet 31 increases the blood flow, relaxes muscles and ligaments of the body orifice region and therefore enhances the dilation and stretch of the body orifice during the utilization of the device 10.

Plurality of Gears

In another embodiment, the device 10 may comprise a plurality of gears 11H. The plurality of gears 11H may connect such as but not limited to: a first end 11A to a second end 11B, a second end 11B to a first end 13A, and/or a second end 11B to a third end 11G (third end 11G described in Multiple shaft section). The plurality of gears 11H may be a part of the controller angular transmission 11E (as illustrated in FIG. 21), an enclosed electric motor 19, and/or the threaded shaft angular transmission 13G. The plurality of gears 11H may be such as but not limited to: straight-cut, helical, bevel, crown, and worm. Each gear of the plurality of gears 11H may be configured in various sizes and dimensions. The plurality of gears 11H transmits a rotation movement, changes the speed of rotation and/or changes the torque between the elements connected to the plurality of gears 11H.

Multiple Shaft

Figure 54A:
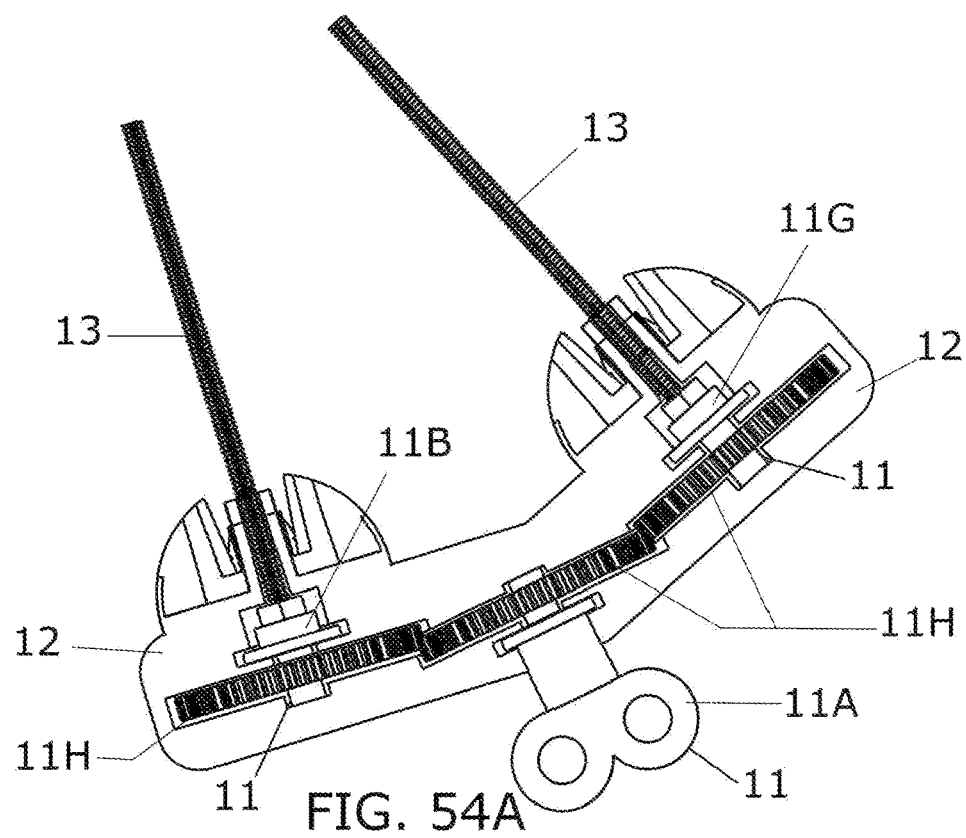
FIG. 54A illustrates a front view of the connection between a controller 11, two threaded shafts 13 and a part of the housing 12 according to an embodiment of the device 10.
Figure 54B:
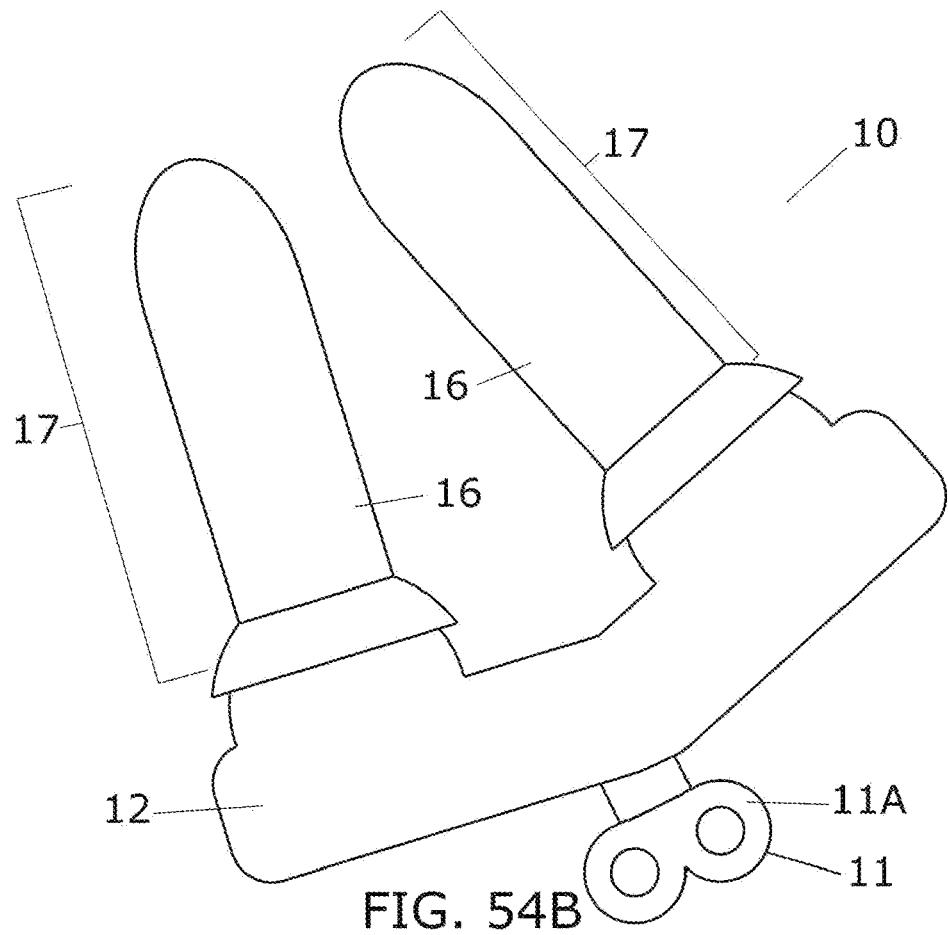
FIG. 54B illustrates a front view of the device 10 with two shafts 17 at their minimum girth size according to an embodiment of the device 10.

In another embodiment as illustrated in FIG. 54, the device 10 may comprise a controller 11 having a third end 11G and a plurality of gears 11H, two threaded shafts 13, a housing 12, a plurality of modules 14 (not illustrated in FIG. 54), a plurality of shaft members 15 (not illustrated in FIG. 54), and two sheaths 16. In this embodiment, the housing 12 is configured to receive the controller 11 having a third end 11G and a plurality of gears 11H, two threaded shafts 13, and two sheaths 16. This embodiment allows the user to perform the adjustment of the device 10 in two body orifices at the same time, such as a vagina and an anus. FIG. 54A illustrates the connection between a part of the housing 12, two threaded shafts 13 and the controller 11 having a third end 11G and a plurality of gears 11H, in this embodiment. FIG. 54B illustrates the device 10 with two shafts 17 at their minimum girth size in this embodiment.

Figure 55A:
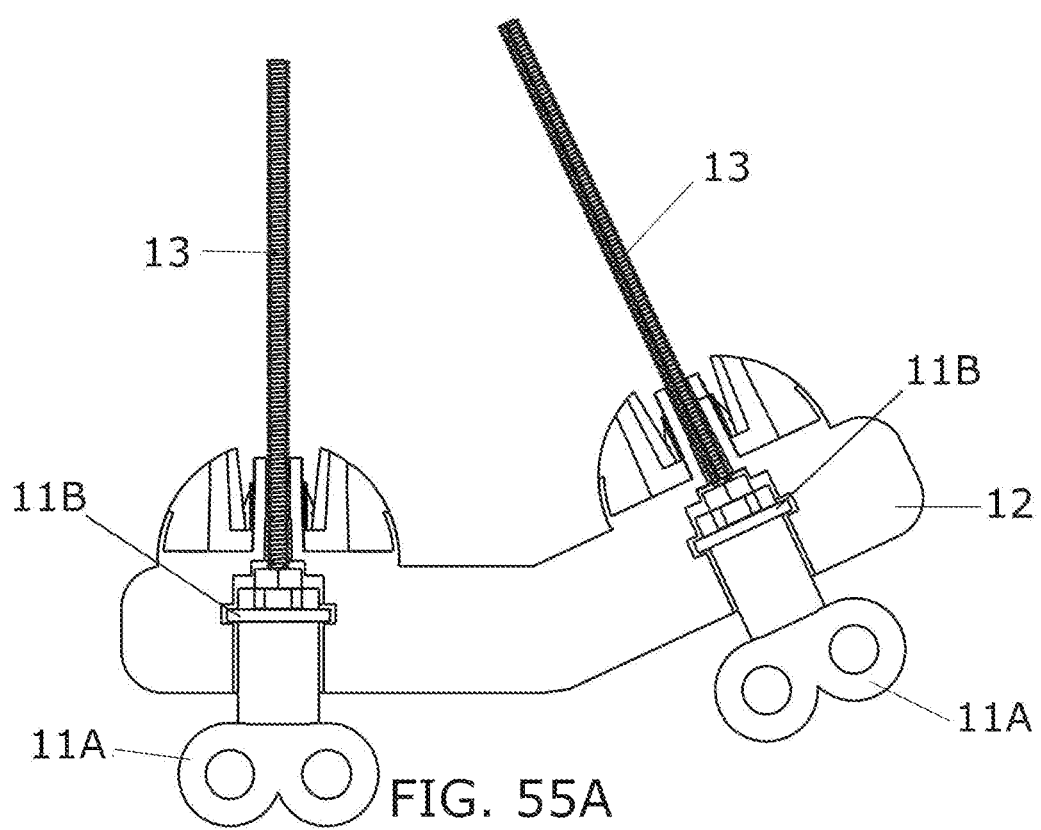
FIG. 55A illustrates a front view of the connection between two controllers 11, two threaded shafts 13 and a part of the housing 12 according to an embodiment of the device 10.
Figure 55B:
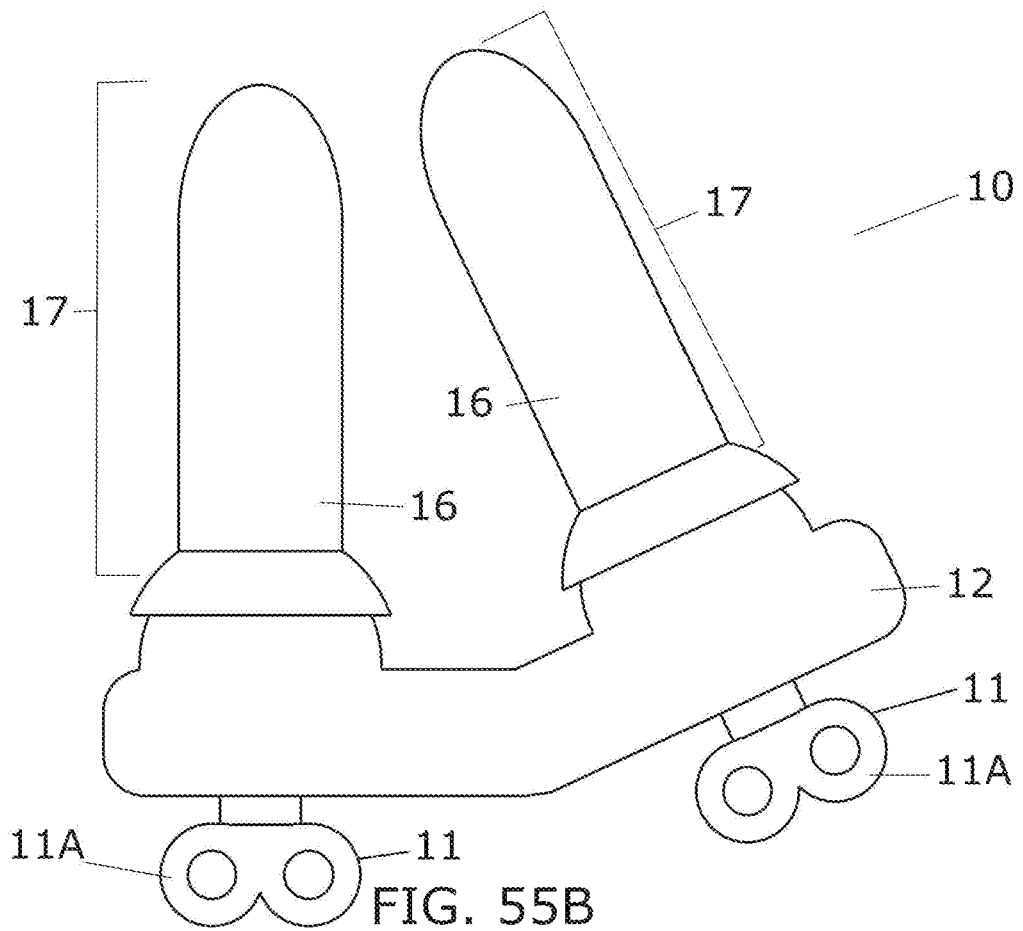
FIG. 55B illustrates a front view of the device 10 with two shafts 17 at their minimum girth size according to an embodiment of the device 10.

In another embodiment as illustrated in FIG. 55, the device 10 may comprise two controllers 11, two threaded shafts 13, a housing 12, a plurality of modules 14 (not illustrated in FIG. 55), a plurality of shaft members 15 (not illustrated in FIG. 55), and two sheaths 16. In this embodiment the housing 12 is configured to receive two controllers 11, two threaded shafts 13, a plurality of shaft members 15 and two sheaths 16. This embodiment allows the user to perform the adjustment of the device 10 in two body orifices at the same time, such as a vagina and an anus. FIG. 55A illustrates the connection between two controllers 11, two threaded shafts 13 and a part of the housing 12, in this embodiment. FIG. 55B illustrates the device 10 with two shafts 17 at their minimum girth size in this embodiment.

Alternative Embodiments of the Device

As illustrated in FIG. 56 (plurality of shaft members 15 and sheath 16 not illustrated in FIG. 56), an alternative embodiment of the device 10 is to configure the device 10 with at least one controller 11 having a first end 11A and a second end 11B, at least one threaded shaft 13 having a first end 13A, a middle section 13B, a second end 13C, and a longitudinal axis, a housing 12 having a controller first end 12A, a shaft member second end 12B having a plurality of shaft member grooves 12BA and a plurality of shaft member protrusions 12BB, a controller canal 12G, a housing canal 12H, at least one module 14 having at least one conical section with a slant height 14A and a module canal such as: a non-threaded canal, a threaded canal, a threaded canal having at least one fastener cavity, or a non-threaded canal having at least one fastener cavity 14CA, a plurality of shaft members having a first end 15A having at least one housing groove 15AA, a middle section 15B, at least one module cavity 15C with a sloped edge 15CA, and a tip end 15E, and at least one sheath 16 having a first end 16A, a middle section 16B, a tip end 16C, and a sheath girth. Preferably, the module canal passes through the conical section with a slant height 14A, from the apex to the center of the flat base. The module canal may be configured to not pass through the entire module 14 when the device 10 only has one module 14 or when the module 14 is located at second end of the threaded shaft 13. In this embodiment, the module 14 (or a plurality of modules 14) is secured to the threaded shaft 13, such that when the threaded shaft 13 is left-handed threaded and the apex of the conical section with a slant height 14A is in the direction of the housing 12 and when the user rotates the controller 11 clockwise, the controller 11 rotates and travels at the same time following the longitudinal axis of the threaded shaft 13 in a direction going from the shaft member second end 12B to the controller first end 12A of the housing 12 inside the controller canal 12G, the threaded shaft 13 connected to the controller 11 rotates clockwise and travels at the same time following the longitudinal axis of the threaded shaft 13 in a direction going from the shaft member second end 12B to the controller first end 12A of the housing 12 inside the housing canal 12H and the controller canal 12G, and the module 14 (or a plurality of modules 14) secured to the threaded shaft 13 rotates clockwise and travels at the same time following the longitudinal axis of the threaded shaft 13 in the direction of the housing 12, the slant height of the conical section with a slant height 14A of the module 14 slides against the sloped edge 15CA of the module cavity 150 of the shaft member 15 outside of the module cavity 15C of the shaft member 15, making each shaft member 15 travels perpendicularly to the longitudinal axis of the threaded shaft 13 in the opposite direction of the longitudinal axis of the threaded shaft 13, each longitudinal axis of each shaft member 15 is maintained approximatively or exactly parallel with the longitudinal axis of the threaded shaft 13, the sheath 16 made of a resilient material, deforms elastically from its original shape, the girth size of the shaft 17 increases, until the controller 11 is no longer rotated clockwise by the user, meaning that the user reached the desired girth size of the shaft 17, meaning that the threaded shaft 13 and the module 14 (or a plurality of modules 14) are no longer rotated and are stopped from traveling following the longitudinal axis of the threaded shaft 13, each shaft member 15 stopped from traveling perpendicularly to the longitudinal axis of the threaded shaft 13 in the opposite direction of the longitudinal axis of the threaded shaft 13, the sheath 16 stopped from deforming elastically, the girth size of the shaft 17 stopped from increasing. The girth size of the shaft 17 is sustained at this size. Then, when the user rotates the controller 11 counter-clockwise, the controller 11 rotates and travels at the same time following the longitudinal axis of the threaded shaft 13 in a direction going from the controller first end 12A to the shaft member second end 12B of the housing 12 inside the controller canal 12G, the threaded shaft 13 connected to the controller 11 rotates counter-clockwise and travels at the same time following the longitudinal axis of the threaded shaft 13 in a direction going from the controller first end 12A to the shaft member second end 12B of the housing 12 inside the housing canal 12H and the controller canal 12G, and the module 14 (or a plurality of modules 14) secured to the threaded shaft 13 rotates counter-clockwise and travels at the same time following the longitudinal axis of the threaded shaft 13 in the opposite direction of the housing 12, the sheath 16 retrieves its original shape, the slant height of the conical section with a slant height 14A of the module 14 slides back against the sloped edge 15CA of the module cavity 150 of the shaft member 15 inside of the module cavity 150 of the shaft member 15, making each shaft member 15 travel back perpendicularly to the longitudinal axis of the threaded shaft 13 in the direction of the longitudinal axis of the threaded shaft 13, each longitudinal axis of each shaft member 15 is maintained approximatively or exactly parallel with the longitudinal axis of the threaded shaft 13, the girth size of the shaft 17 decreases, until the controller 11 is no longer rotated clockwise by the user, meaning that the user reached the desired girth size of the shaft, meaning that the threaded shaft 13 and the module 14 (or a plurality of modules 14) are no longer rotated and are stopped from traveling, each shaft member 15 stopped from traveling perpendicularly to the longitudinal axis of the threaded shaft 13 in the direction of the longitudinal axis of the threaded shaft 13, the sheath 16 stopped from retrieving its original shape, the girth size of the shaft 17 stopped from decreasing. The girth size of the shaft 17 is sustained at this size, until the user rotates again the controller 11 clockwise or counter-clockwise. The controller 11 can no longer be rotated when the user reached the maximum girth size of the shaft 17 offered of the shaft 17 by the device 10, meaning that the threaded shaft 13 can no longer be rotated due to the fact that at least one module 14 is stopped from traveling by pressing against at least one edge of the housing 12, and/or at least one maximum translation stopper 13E (maximum translation stopper 13E not illustrated in FIG. 56) presses against at least one edge of the housing 12, and/or that at least one shaft member 15 is stopped from traveling perpendicularly to the longitudinal axis of the threaded shaft 13 in the opposite direction of the longitudinal axis of the threaded shaft 13 by pressing against at least one edge of the housing 12. The controller 11 can no longer be rotated when the user reached the minimum girth size of the shaft 17 offered by the device 10, meaning that the threaded shaft 13 can no longer be rotated due to the fact that at least one module 14 is stopped from traveling by pressing against at least one edge of the module cavity 15C of the shaft member 15, and/or at least one minimum translation stopper 13F (minimum translation stopper 13F not illustrated in FIG. 56) presses against at least one edge of the housing 12. Preferably in this embodiment, the controller canal 12G is a non-threaded canal and the housing canal 12H is such as: a threaded canal, a threaded canal having at least one fastener cavity, and a non-threaded canal having at least one fastener cavity. In this embodiment, the module 14 (or plurality of modules 14) is secured to threaded shaft 13 by such as but not limited to: welding, and gluing. In this embodiment, the function of the housing canal 12H is to interact mechanically with the threaded shaft 13 when the threaded shaft 13 rotates, to make the threaded shaft 13 travel following the longitudinal axis of the threaded shaft 13. When the housing canal 12H is threaded, the mechanical interaction between the housing canal 12H and the threaded shaft 13 is direct, when the housing canal 12H is non-threaded having at least one fastener cavity, in which the fastener cavity includes at least one fastener such as but not limited to: a nut fastener, and/or a wing nut fastener, the mechanical interaction between the housing canal 12H and the threaded shaft 13 is via the fastener inserted inside the fastener cavity, and when the housing canal 12H is threaded having at least one fastener cavity, in which the fastener cavity includes at least one fastener such as but not limited to: a nut fastener, and/or a wing nut fastener, the mechanical interaction between the housing canal 12H and the threaded shaft 13 is direct and via the fastener inserted inside the fastener cavity.

Figure 57E:
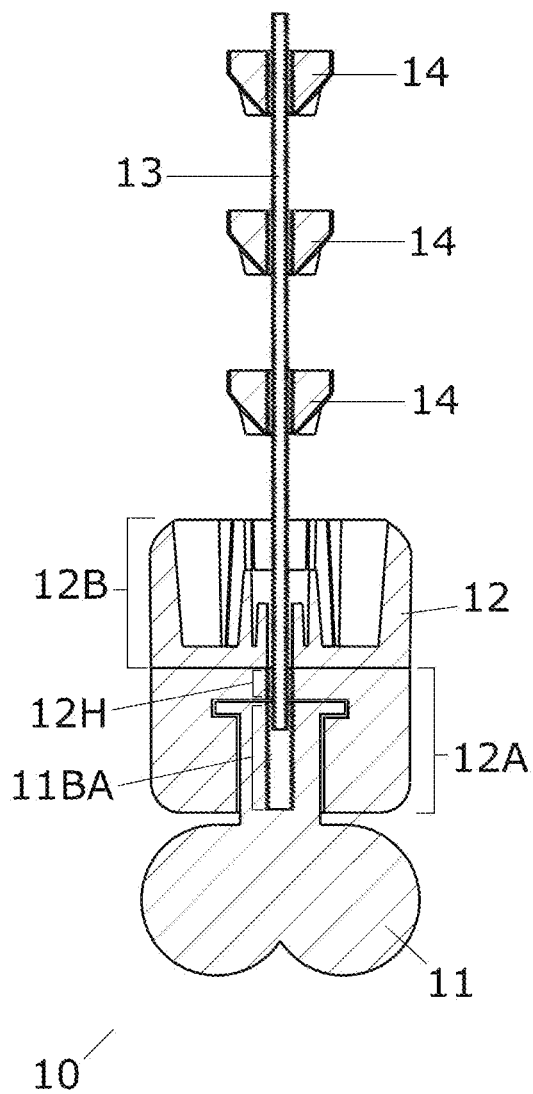
FIG. 57E illustrates a section view of FIG. 57O.
Figure 57F:
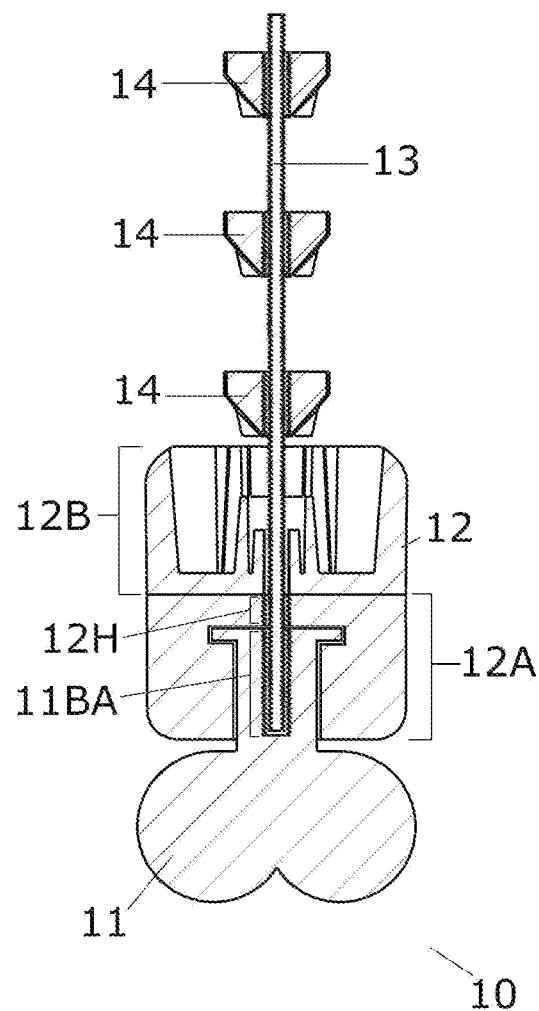
FIG. 57F illustrates a section view of FIG. 57D.
Figure 58A:
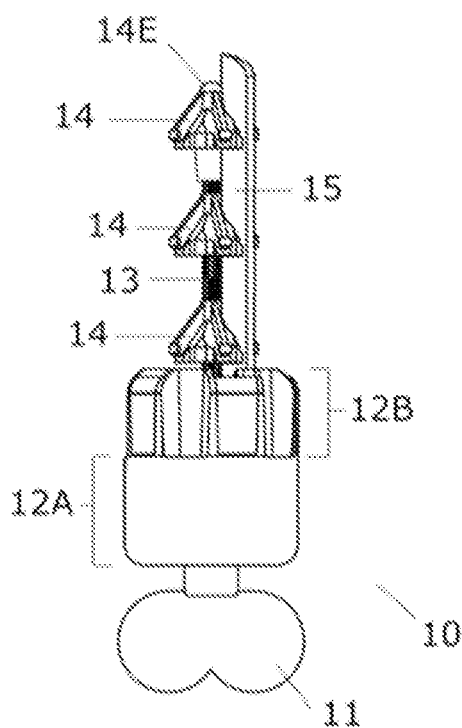
FIG. 58A illustrates a front view of the device 10 with the shaft 17 at its minimum girth size according to an embodiment of the device 10 (sheath 16 not illustrated in FIG. 58A, and only one shaft member 15 illustrated in FIG. 58A).
Figure 58B:
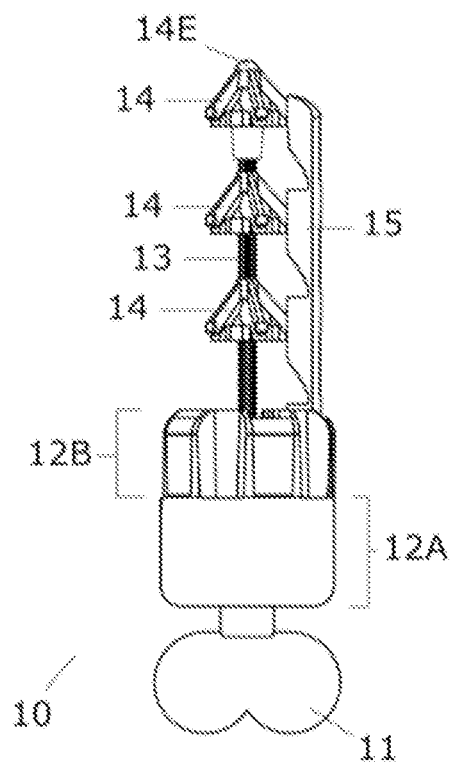
FIG. 58B illustrates a front view of the device 10 with the shaft 17 at its maximum girth size according to an embodiment of the device 10 (sheath 16 not illustrated in FIG. 58B, and only one shaft member 15 illustrated in FIG. 58B).
Figure 58C:
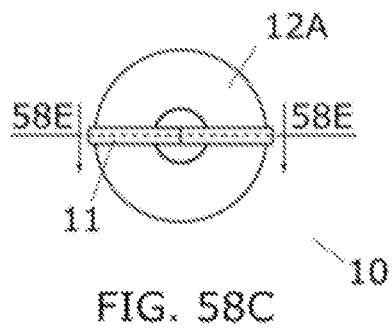
FIG. 58C illustrates a bottom view of FIG. 58A.
Figure 58D:
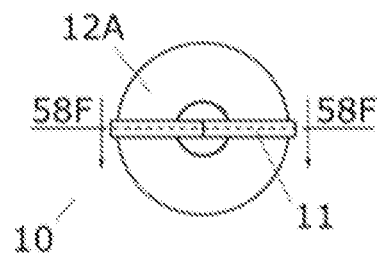
FIG. 58D illustrates a bottom view of FIG. 58B.
Figure 58E:
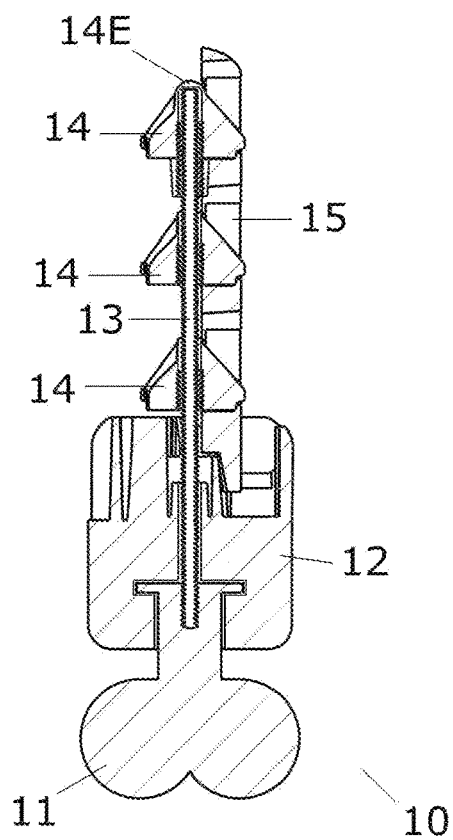
FIG. 58E illustrates a section view of FIG. 58C.
Figure 58F:
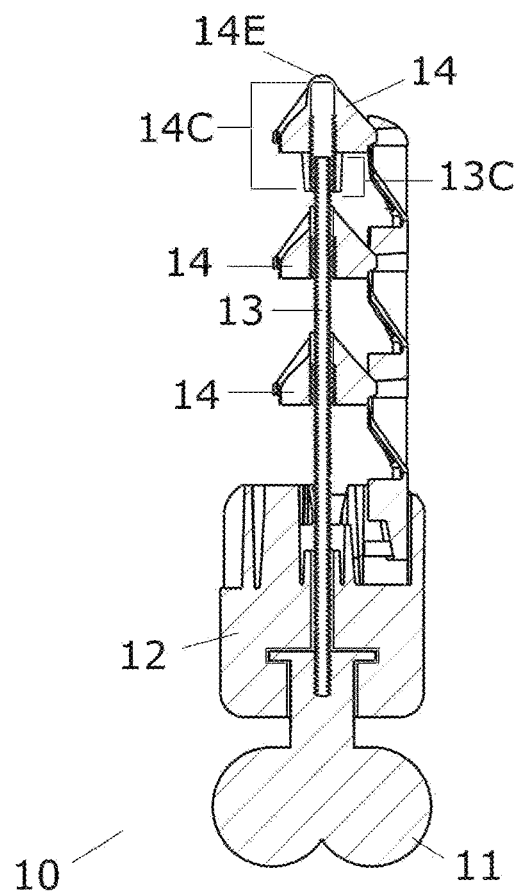
FIG. 58F illustrates a section view of FIG. 58D.

As illustrated in FIG. 57 (plurality of shaft members 15 and sheath 16 not illustrated in FIG. 57), an alternative embodiment of the device 10 is to configure the device 10 with at least one controller 11 having a first end 11A and a second end 11B having a threaded shaft canal 11BA, at least one threaded shaft 13 having a first end 13A, a middle section 13B, a second end 13C, and a longitudinal axis, a housing 12 having a controller first end 12A, a shaft member second end 12B having a plurality of shaft member grooves 12BA and a plurality of shaft member protrusions 12BB, and a non-threaded canal 12C, at least one module 14 having at least one conical section with a slant height 14A, at least one anti-rotation connector selected from a group consisting of: a linear anti-rotation connector 14B, a capital letter T shape anti-rotation connectors 24 and an inclined capital letter T shape anti-rotation connector 25, and a module canal such as: a non-threaded canal, a threaded canal, a threaded canal having at least one fastener cavity, or a non-threaded canal having at least one fastener cavity 140A, a plurality of shaft members having a first end 15A having at least one housing groove 15AA, a middle section 15B, at least one module cavity 150 with a sloped edge 15CA, at least one module connector groove 15D, and a tip end 15E, and at least one sheath 16 having a first end 16A, a middle section 16B, a tip end 160, and a sheath girth. Preferably, the module canal passes through the conical section with a slant height 14A, from the apex to the center of the flat base. The module canal may be configured to not pass through the entire module 14 when the device 10 only has one module 14 or when the module 14 is located at second end of the threaded shaft 13. In this embodiment, the module 14 (or a plurality of modules 14) is secured to the threaded shaft 13, such that when the threaded shaft 13 is right-handed threaded, and the apex of the conical section with a slant height 14A is in the direction of the housing 12 and when the user rotates the controller 11 clockwise, the threaded shaft 13 (prevented from rotating around the longitudinal axis of the threaded shaft 13 by the module 14) travels in a direction going from the shaft member second end 12B to the controller first end 12A of the housing 12 inside the threaded shaft canal 11BA, and the module 14 (or a plurality of modules 14) secured to the threaded shaft 13 and prevented from rotating around the longitudinal axis of the threaded shaft 13 by the anti-rotation connector of the module 14 slidably connected to the module connector groove 15D of the shaft member 15 travels following the longitudinal axis of the threaded shaft 13 in the direction of the housing 12, the slant height of the conical section with a slant height 14A of the module 14 slides against the sloped edge 15CA of the module cavity 15C of the shaft member 15 outside of the module cavity 15C of the shaft member 15, making each shaft member 15 travels perpendicularly to the longitudinal axis of the threaded shaft 13 in the opposite direction of the longitudinal axis of the threaded shaft 13, each longitudinal axis of each shaft member 15 is maintained approximatively or exactly parallel with the longitudinal axis of the threaded shaft 13, the sheath 16 made of a resilient material, deforms elastically from its original shape, the girth size of the shaft 17 increases, until the controller 11 is no longer rotated clockwise by the user, meaning that the user reached the desired girth size of the shaft 17, meaning that the threaded shaft 13 is no longer rotated, the module 14 (or a plurality of modules 14) stopped from traveling, each shaft member 15 stopped from traveling perpendicularly to the longitudinal axis of the threaded shaft 13 in the opposite direction of the longitudinal axis of the threaded shaft 13, the sheath 16 stopped from deforming elastically, the girth size of the shaft 17 stopped from increasing. The girth size of the shaft 17 is sustained at this size. Then, when the user rotates the controller 11 counter-clockwise, the threaded shaft 13 travels back in a direction going from the controller first end 12A to the shaft member second end 12B of the housing 12 inside the threaded shaft canal 11BA, and the module 14 (or a plurality of modules 14) travels back following the longitudinal axis of the threaded shaft 13 in the opposite direction of the housing 12, the sheath 16 retrieves its original shape, the slant height of the conical section with a slant height 14A of the module 14 slides back against the sloped edge 15CA of the module cavity 15C of the shaft member 15 inside of the module cavity 15C of the shaft member 15, making each shaft member 15 travel back perpendicularly to the longitudinal axis of the threaded shaft 13 in the direction of the longitudinal axis of the threaded shaft 13, each longitudinal axis of each shaft member 15 is maintained approximatively or exactly parallel with the longitudinal axis of the threaded shaft 13, the girth size of the shaft 17 decreases, until the controller 11 is no longer rotated counter-clockwise by the user, meaning that the user reached the desired girth size of the shaft 17, meaning that the threaded shaft 13 is no longer rotated, the module 14 (or a plurality of modules 14) stopped from traveling, each shaft member 15 stopped from traveling perpendicularly to the longitudinal axis of the threaded shaft 13 in the direction of the longitudinal axis of the threaded shaft 13, the sheath 16 stopped from retrieving its original shape, the girth size of the shaft 17 stopped from decreasing. The girth size of the shaft 17 is sustained at this size, until the user rotates again the controller 11 clockwise or counter-clockwise. The controller 11 can no longer be rotated when the user reached the maximum girth size of the shaft 17 offered by the device 10, meaning that the threaded shaft 13 can no longer be rotated due to the fact that at least one module 14 is stopped from traveling by pressing against at least one edge of the housing 12, and/or by pressing against at least one edge of the module connector groove 15D of at least one shaft member 15, and/or at least one maximum translation stopper 13E (maximum translation stopper 13E not illustrated in FIG. 57) presses against one edge of the housing 12 and/or one edge of the controller 11, and/or that at least one shaft member 15 is stopped from traveling perpendicularly to the longitudinal axis of the threaded shaft 13 in the opposite direction of the longitudinal axis of the threaded shaft 13 by pressing against at least one edge of the housing 12. The controller 11 can no longer be rotated when the user reached the minimum girth size of the shaft 17 offered by the device 10, meaning that the threaded shaft 13 can no longer be rotated due to the fact that at least one module 14 is stopped from traveling by pressing against at least one edge of the module cavity 15C, and/or at least one minimum translation stopper 13F (minimum translation stopper 13F not illustrated in FIG. 57) presses against one edge of the housing 12 and/or one edge of the controller 11. The threaded shaft canal 11BA is such as: a threaded canal, a threaded canal having at least one fastener cavity, and a non-threaded canal having at least one fastener cavity. In this embodiment, the module 14 (or plurality of modules 14) is secured to threaded shaft 13 by such as but not limited to: welding, and gluing. In this embodiment, the function of the threaded shaft canal 11BA is to interact mechanically with the threaded shaft 13 when the controller 11 rotates, to make the threaded shaft 13 (prevented from rotating around the longitudinal axis of the threaded shaft 13) travel following the longitudinal axis of the threaded shaft 13. When the threaded shaft canal 11BA is threaded, the mechanical interaction between the threaded shaft canal 11BA and the threaded shaft 13 is direct, when the threaded shaft canal 11BA is non-threaded having at least one fastener cavity, in which the fastener cavity includes at least one fastener such as but not limited to: a nut fastener, and/or a wing nut fastener, the mechanical interaction between the threaded shaft canal 11BA and the threaded shaft 13 is via the fastener inserted inside the fastener cavity, and when the threaded shaft canal 11BA is threaded having at least one fastener cavity, in which the fastener cavity includes at least one fastener such as but not limited to: a nut fastener, and/or a wing nut fastener, the mechanical interaction between the threaded shaft canal 11BA and the threaded shaft 13 is direct and via the fastener inserted inside the fastener cavity. In this embodiment, the housing 12 may comprise a housing canal 12H (as illustrated in FIG. 57E and FIG. 57F). The function of the housing canal 12H is to interact mechanically with the threaded shaft 13 when the controller 11 rotates, to make the threaded shaft 13 (prevented from rotating around the longitudinal axis of the threaded shaft 13) travel following the longitudinal axis of the threaded shaft 13. When the housing canal 12H is threaded, the mechanical interaction between the housing canal 12H and the threaded shaft 13 is direct, when the housing canal 12H is non-threaded having at least one fastener cavity, in which the fastener cavity includes at least one fastener such as but not limited to: a nut fastener, and/or a wing nut fastener, the mechanical interaction between the housing canal 12H and the threaded shaft 13 is via the fastener inserted inside the fastener cavity, and when the housing canal 12H is threaded having at least one fastener cavity, in which the fastener cavity includes at least one fastener such as but not limited to: a nut fastener, and/or a wing nut fastener, the mechanical interaction between the housing canal 12H and the threaded shaft 13 is direct and via the fastener inserted inside the fastener cavity.

An alternative embodiment of the device 10 (not illustrated) is to configure the device 10 with at least one controller 11 having a first end 11A and a second end 11B, at least one threaded shaft 13 having a first end 13A, a middle section 13B, a second end 13C, and a longitudinal axis, a housing 12 having a controller first end 12A, a shaft member second end 12B having a plurality of shaft member grooves 12BA and a plurality of shaft member protrusions 12BB, at least one module anti-rotation protrusion 12F, and a non-threaded canal 120, at least one module 14 having at least one conical section with a slant height 14A, at least one housing anti-rotation cavity 14D, and a canal 140, a plurality of shaft members having a first end 15A having at least one housing groove 15AA, a middle section 15B, at least one module cavity 150 with a sloped edge 150A, and a tip end 15E, and at least one sheath 16 having a first end 16A, a middle section 16B, a tip end 160, and a sheath girth. Attention to the fact that it is also possible to locate the housing anti-rotation cavity 140 on the housing 12, and the module anti-rotation protrusion 12F on the module 14. In this embodiment, the device 10 may comprise at least one maximum translation stopper 13E and/or at least one minimum translation stopper 13F to stop the rotation of the controller 11.

An alternative embodiment of the device 10 (not illustrated) is to configure the device 10 with at least one controller 11 having a first end 11A and a second end 11B having a threaded shaft canal 11BA, at least one threaded shaft 13 having a first end 13A, a middle section 13B, a second end 13C, and a longitudinal axis, a housing 12 having a controller first end 12A, a shaft member second end 12B having a plurality of shaft member grooves 12BA and a plurality of shaft member protrusions 12BB, at least one module anti-rotation protrusion 12F, and a non-threaded canal 12C, at least one module 14 having at least one conical section with a slant height 14A, at least one housing anti-rotation cavity 14D, and a module canal such as: a non-threaded canal, a threaded canal, a threaded canal having at least one fastener cavity, or a non-threaded canal having at least one fastener cavity 14CA, a plurality of shaft members having a first end 15A having at least one housing groove 15AA, a middle section 15B, at least one module cavity 15C with a sloped edge 15CA, and a tip end 15E, and at least one sheath 16 having a first end 16A, a middle section 16B, a tip end 16C, and a sheath girth. Attention to the fact that it is also possible to locate the housing anti-rotation cavity 14D on the housing 12, and the module anti-rotation protrusion 12F on the module 14. Preferably, the module canal passes through the conical section with a slant height 14A, from the apex to the center of the flat base. The module canal may be configured to not pass through the entire module 14 when the device 10 only has one module 14 or when the module 14 is located at second end of the threaded shaft 13. In this embodiment, the device 10 may comprise at least one maximum translation stopper 13E and/or at 1935 least one minimum translation stopper 13F.

Multiple Combination of Element

Attention being called to the fact that it is considered obvious that the device 10 may be configured with in any combination of the features, parts, members, elements and components presented in this document.

I claim:

1. A girth adjustable device comprising:
   a. at least one controller having a first end, and a second end;
   b. at least one threaded shaft having a first end, a middle section, a second end, and a longitudinal axis, wherein said first end of said threaded shaft is connected to said second end of said controller;
   c. a housing having a controller first end, a shaft member second end having a plurality of shaft member grooves and a plurality of shaft member protrusions, and a non-threaded canal, wherein said non-threaded canal receives said first end of said threaded shaft, wherein said housing encloses at least said second end of said controller and said first end of said threaded shaft;
   d. at least one module having at least one conical section with a slant height, at least one anti-rotation connector selected from a group consisting of: a linear anti-rotation connector, a capital letter T shape anti-rotation connector, and an inclined capital letter T shape anti-rotation connector, and a canal selected from a group consisting of: a threaded canal, a threaded canal having at least one fastener cavity, and a non-threaded canal having at least one fastener cavity, wherein said canal receives said threaded shaft;
   e. a plurality of shaft members having a first end having at least one housing groove, a middle section, at least one module cavity with a sloped edge, at least one module connector groove, and a tip end, wherein said plurality of shaft members surrounds said threaded shaft and said module, wherein said shaft member second end having a plurality of shaft member grooves and a plurality of shaft member protrusions of said housing slidably receives said first end of said shaft member, wherein said module cavity with a sloped edge of said shaft member slidably receives said conical section with a slant height of said module, wherein said module connector groove of said shaft member slidably receives said anti-rotation connector of said module; and
   f. at least one sheath having a first end, a middle section, a tip end, and a sheath girth, wherein said sheath surrounds at least said plurality of shaft members, wherein said sheath is made of a resilient material, wherein when said controller rotates in the direction of increase of said sheath girth, said threaded shaft rotates, said module prevented from rotating around said longitudinal axis of said threaded shaft by said anti-rotation connector of said module slidably connected to said module connector groove of said shaft member travels along said threaded shaft, said conical section with a slant height of said module slides against said sloped edge of said module cavity with a sloped edge of said shaft member outside said module cavity with a sloped edge of said shaft member, each said shaft member of said plurality of shaft members travels perpendicularly to said longitudinal axis of said threaded shaft in the opposite direction of said longitudinal axis of said threaded shaft, said sheath deforms elastically from its original shape, and girth size of said sheath girth increases, when girth size of said sheath girth increased, when said controller rotates in the direction of decrease of said sheath girth, said threaded shaft rotates, said module prevented from rotating around said longitudinal axis of said threaded shaft by said anti-rotation connector of said module slidably connected to said module connector groove of said shaft member travels back along said threaded shaft, said sheath retrieves its original shape, said conical section with a slant height of said module slides back against said sloped edge of said module cavity with a sloped edge of said shaft member inside said module cavity with a sloped edge of said shaft member, each said shaft member of said plurality of shaft members travels back perpendicularly to said longitudinal axis of said threaded shaft in the direction of said longitudinal axis of said threaded shaft, and girth size of said sheath girth decreases, wherein increase of girth size of said sheath girth and decrease of girth size of said sheath girth are repeatable.

2. A girth adjustable device comprising:
   a. at least one controller having a first end, and a second end;
   b. at least one threaded shaft having a first end, a middle section, a second end, and a longitudinal axis, wherein said first end of said threaded shaft is connected to said second end of said controller;
   c. a housing having a controller first end, a shaft member second end having a plurality of shaft member grooves and a plurality of shaft member protrusions, a controller canal, and a housing canal selected from a group consisting of: a threaded canal, a threaded canal having at least one fastener cavity, and a non-threaded canal having at least one fastener cavity, wherein said controller canal receives said second end of said controller and said first end of said threaded shaft, wherein said housing canal receives said first end of said threaded shaft, wherein said housing encloses at least said second end of said controller and said first end of said threaded shaft;
   d. at least one module having at least one conical section with a slant height, and a module canal selected from a group consisting of: a non-threaded canal, a threaded canal, a threaded canal having at least one fastener cavity, and a non-threaded canal having at least one fastener cavity, wherein said module canal receives said threaded shaft, wherein said module is secured to said threaded shaft;
   e. a plurality of shaft members having a first end having at least one housing groove, a middle section, at least one module cavity with a sloped edge, and a tip end, wherein said plurality of shaft members surrounds said threaded shaft and said module, wherein said shaft member second end having a plurality of shaft member grooves and a plurality of shaft member protrusions of said housing slidably receives said first end of said shaft member, wherein said module cavity with a sloped edge of said shaft member slidably receives said conical section with a slant height of said module; and
   f. at least one sheath having a first end, a middle section, a tip end, and a sheath girth, wherein said sheath surrounds at least said plurality of shaft members, wherein said sheath is made of a resilient material, wherein when said controller rotates in the direction of increase of said sheath girth, said controller, said threaded shaft, and said module rotate and travel following said longitudinal axis of said threaded shaft, said conical section with a slant height of said module slides against said sloped edge of said module cavity with a sloped edge of said shaft member outside said module cavity with a sloped edge of said shaft member, each said shaft member of said plurality of shaft members travels perpendicularly to said longitudinal axis of said threaded shaft in the opposite direction of said longitudinal axis of said threaded shaft, said sheath deforms elastically from its original shape, and girth size of said sheath girth increases, wherein when girth size of said sheath girth increased, when said controller rotates in the direction of decrease of said sheath girth, said controller, said threaded shaft, and said module rotate and travel back following said longitudinal axis of said threaded shaft, said sheath retrieves its original shape, said conical section with a slant height of said module slides back against said sloped edge of said module cavity with a sloped edge of said shaft member inside said module cavity with a sloped edge of said shaft member, each said shaft member of said plurality of shaft members travels back perpendicularly to said longitudinal axis of said threaded shaft in the direction of said longitudinal axis of said threaded shaft, and girth size of said sheath girth decreases, wherein increase of girth size of said sheath girth and decrease of girth size of said sheath girth are repeatable.

3. A girth adjustable device comprising:
a. at least one controller having a first end, and a second end having a threaded shaft canal selected from a group consisting of: a threaded canal, a threaded canal having at least one fastener cavity, and a non-threaded canal having at least one fastener cavity;
b. at least one threaded shaft having a first end, a middle section, a second end, and a longitudinal axis, wherein said threaded shaft canal of said second end of said controller receives said first end of said threaded shaft;
c. a housing having a controller first end, a shaft member second end having a plurality of shaft member grooves and a plurality of shaft member protrusions, and a non-threaded canal, wherein said non-threaded canal receives said first end of said threaded shaft, wherein said housing encloses at least said second end of said controller and said first end of said threaded shaft;
d. at least one module having at least one conical section with a slant height, at least one anti-rotation connector selected from a group consisting of: a linear anti-rotation connector, a capital letter T shape anti-rotation connector, and an inclined capital letter T shape anti-rotation connector, and a module canal selected from a group consisting of: a non-threaded canal, a threaded canal, a threaded canal having at least one fastener cavity, and a non-threaded canal having at least one fastener cavity, wherein said module canal receives said threaded shaft, wherein said module is secured to said threaded shaft;
e. a plurality of shaft members having a first end having at least one housing groove, a middle section, at least one module cavity with a sloped edge, at least one module connector groove, and a tip end, wherein said plurality of shaft members surrounds said threaded shaft and said module, wherein said shaft member second end having a plurality of shaft member grooves and a plurality of shaft member protrusions of said housing slidably receives said first end of said shaft member, wherein said module cavity with a sloped edge of said shaft member slidably receives said conical section with a slant height of said module, wherein said module connector groove of said shaft member slidably receives said anti-rotation connector of said module; and
f. at least one sheath having a first end, a middle section, a tip end, and a sheath girth, wherein said sheath surrounds at least said plurality of shaft members, wherein said sheath is made of a resilient material, wherein when said controller rotates in the direction of increase of said sheath girth, said threaded shaft and said module prevented from rotating around said longitudinal axis of said threaded shaft by said anti-rotation connector of said module slidably connected to said module connector groove of said shaft member travel following said longitudinal axis of said threaded shaft, said conical section with a slant height of said module slides against said sloped edge of said module cavity with a sloped edge of said shaft member outside said module cavity with a sloped edge of said shaft member, each said shaft member of said plurality of shaft members travels perpendicularly to said longitudinal axis of said threaded shaft in the opposite direction of said longitudinal axis of said threaded shaft, said sheath deforms elastically from its original shape, and girth size of said sheath girth increases, wherein when girth size of said sheath girth increased, when said controller rotates in the direction of decrease of said sheath girth, said threaded shaft and said module prevented from rotating around said longitudinal axis of said threaded shaft by said anti-rotation connector of said module slidably connected to said module connector groove of said shaft member travel back following said longitudinal axis of said threaded shaft, said sheath retrieves its original shape, said conical section with a slant height of said module slides back against said sloped edge of said module cavity with a sloped edge of said shaft member inside said module cavity with a sloped edge of said shaft member, each said shaft member of said plurality of shaft members travels back perpendicularly to said longitudinal axis of said threaded shaft in the direction of said longitudinal axis of said threaded shaft, and girth size of said sheath girth decreases, wherein increase of girth size of said sheath girth and decrease of girth size of said sheath girth are repeatable.

4. A girth adjustable device comprising:
a. at least one controller having a first end, and a second end;
b. at least one threaded shaft having a first end, a middle section, a second end, and a longitudinal axis, wherein said first end of said threaded shaft is connected to said second end of said controller;
c. a housing having a controller first end, a shaft member second end having a plurality of shaft member grooves and a plurality of shaft member protrusions, at least one module anti-rotation protrusion, and a non-threaded canal, wherein said non-threaded canal receives said first end of said threaded shaft, wherein said housing encloses at least said second end of said controller and said first end of said threaded shaft;
d. at least one module having at least one conical section with a slant height, at least one housing anti-rotation cavity, and a canal selected from a group consisting of: a threaded canal, a threaded canal having at least one fastener cavity, and a non-threaded canal having at least one fastener cavity, wherein said housing anti-rotation cavity of said module slidably receives said module anti-rotation protrusion of said housing, wherein said canal receives said threaded shaft;
e. a plurality of shaft members having a first end having at least one housing groove, a middle section, at least one module cavity with a sloped edge, and a tip end, wherein said plurality of shaft members surrounds said threaded shaft and said module, wherein said shaft member second end having a plurality of shaft member grooves and a plurality of shaft member protrusions of said housing slidably receives said first end of said shaft member, wherein said module cavity with a sloped edge of said shaft member slidably receives said conical section with a slant height of said module; and f. at least one sheath having a first end, a middle section, a tip end, and a sheath girth, wherein said sheath surrounds at least said plurality of shaft members, wherein said sheath is made of a resilient material, wherein when said controller rotates in the direction of increase of said sheath girth, said threaded shaft rotates, said module prevented from rotating around said longitudinal axis of said threaded shaft by said module anti-rotation protrusion of said housing slidably connected to said housing anti-rotation cavity of said module travels along said threaded shaft, said conical section with a slant height of said module slides against said sloped edge of said module cavity with a sloped edge of said shaft member outside said module cavity with a sloped edge of said shaft member, each said shaft member of said plurality of shaft members travels perpendicularly to said longitudinal axis of said threaded shaft in the opposite direction of said longitudinal axis of said threaded shaft, said sheath deforms elastically from its original shape, and girth size of said sheath girth increases, wherein when girth size of said sheath girth increased, when said controller rotates in the direction of decrease of said sheath girth, said threaded shaft rotates, said module prevented from rotating around said longitudinal axis of said threaded shaft by said module anti-rotation protrusion of said housing slidably connected to said housing anti-rotation cavity of said module travels back along said threaded shaft, said sheath retrieves its original shape, said conical section with a slant height of said module slides back against said sloped edge of said module cavity with a sloped edge of said shaft member inside said module cavity with a sloped edge of said shaft member, each said shaft member of said plurality of shaft members travels back perpendicularly to said longitudinal axis of said threaded shaft in the direction of said longitudinal axis of said threaded shaft, and girth size of said sheath girth decreases, wherein increase of girth size of said sheath girth and decrease of girth size of said sheath girth are repeatable.

5. A girth adjustable device comprising:
a. at least one controller having a first end, and a second end having a threaded shaft canal selected from a group consisting of: a threaded canal, a threaded canal having at least one fastener cavity, and a non-threaded canal having at least one fastener cavity;
b. at least one threaded shaft having a first end, a middle section, a second end, and a longitudinal axis, wherein said threaded shaft canal of said second end of said controller receives said first end of said threaded shaft;
c. a housing having a controller first end, a shaft member second end having a plurality of shaft member grooves and a plurality of shaft member protrusions, at least one module anti-rotation protrusion, and a non-threaded canal, wherein said non-threaded canal receives said first end of said threaded shaft, wherein said housing encloses at least said second end of said controller and said first end of said threaded shaft;
d. at least one module having at least one conical section with a slant height, at least one housing anti-rotation cavity, and a module canal selected from a group consisting of: a non-threaded canal, a threaded canal, a threaded canal having at least one fastener cavity, and a non-threaded canal having at least one fastener cavity, wherein said housing anti-rotation cavity of said module slidably receives said module anti-rotation protrusion of said housing, wherein said module canal receives said threaded shaft, wherein said module is secured to said threaded shaft;
e. a plurality of shaft members having a first end having at least one housing groove, a middle section, at least one module cavity with a sloped edge, and a tip end, wherein said plurality of shaft members surrounds said threaded shaft and said module, wherein said shaft member second end having a plurality of shaft member grooves and a plurality of shaft member protrusions of said housing slidably receives said first end of said shaft member, wherein said module cavity with a sloped edge of said shaft member slidably receives said conical section with a slant height of said module; and
f. at least one sheath having a first end, a middle section, a tip end, and a sheath girth, wherein said sheath surrounds at least said plurality of shaft members, wherein said sheath is made of a resilient material, wherein when said controller rotates in the direction of increase of said sheath girth, said threaded shaft and said module prevented from rotating around said longitudinal axis of said threaded shaft by said module anti-rotation protrusion of said housing slidably connected to said housing anti-rotation cavity of said module travel following said longitudinal axis of said threaded shaft, said conical section with a slant height of said module slides against said sloped edge of said module cavity with a sloped edge of said shaft member outside said module cavity with a sloped edge of said shaft member, each said shaft member of said plurality of shaft members travels perpendicularly to said longitudinal axis of said threaded shaft in the opposite direction of said longitudinal axis of said threaded shaft, said sheath deforms elastically from its original shape, and girth size of said sheath girth increases, wherein when girth size of said sheath girth increased, when said controller rotates in the direction of decrease of said sheath girth, said threaded shaft and said module prevented from rotating around said longitudinal axis of said threaded shaft by said module anti-rotation protrusion of said housing slidably connected to said housing anti-rotation cavity of said module travel back following said longitudinal axis of said threaded shaft, said sheath retrieves its original shape, said conical section with a slant height of said module slides back against said sloped edge of said module cavity with a sloped edge of said shaft member inside said module cavity with a sloped edge of said shaft member, each said shaft member of said plurality of shaft members travels back perpendicularly to said longitudinal axis of said threaded shaft in the direction of said longitudinal axis of said threaded shaft, and girth size of said sheath girth decreases, wherein increase of girth size of said sheath girth and decrease of girth size of said sheath girth are repeatable.

6. A girth adjustable device as recited in claim 1, 2, 3, 4, or 5, wherein said sheath is secured to said plurality of shaft members and/or said housing.

7. A girth adjustable device as recited in claim 1, 2, 3, 4, or 5, wherein said sheath is removably secured to said plurality of shaft members or said plurality of shaft members and said housing.

8. A girth adjustable device as recited in claim 1, 2 or 4, further comprising at least one controller-connector.

9. A girth adjustable device as recited in claim 1, 2, 3, 4, or 5, wherein said threaded shaft further comprises at least one maximum translation stopper.

10. A girth adjustable device as recited in claim 1, 2, 3, 4, or 5, wherein said threaded shaft further comprises at least one minimum translation stopper.

11. A girth adjustable device as recited in claim 1 or 3, further comprising at least one housing anti-rotation cavity.

12. A girth adjustable device as recited in claim 11, further comprising at least one module anti-rotation protrusion.

13. A girth adjustable device as recited in claim 1, 2, 3, 4, or 5, wherein said housing further comprises at least one bearing, wherein said bearing receives said first end of said threaded shaft, and/or said second end of said controller.

14. A girth adjustable device as recited in claim 1, 2, 3, 4, or 5, further comprising at least one friction reducer.

15. A girth adjustable device as recited in claim 1, 2, 3, 4, or 5, wherein said housing further comprises at least one said shaft member protrusion configured as a cantilever snap-fit.

16. A girth adjustable device as recited in claim 3 or 5, wherein said housing further comprises a housing canal selected from a group consisting of: a threaded canal, a threaded canal having at least one fastener cavity, and a non-threaded canal having at least one fastener cavity, wherein said housing canal receives said threaded shaft.

17. A girth adjustable device as recited in claim 2, wherein said housing further comprises said controller canal selected from a group consisting of: a threaded canal, a threaded canal having at least one fastener cavity, and a non-threaded canal having at least one fastener cavity.

18. A girth adjustable device as recited in claim 17, wherein said second end of said controller is threaded, wherein said controller canal receives said second end of said controller.

19. A girth adjustable device as recited in claim 1, 2, 3, 4, or 5, wherein said plurality of shaft members further comprises at least one side extension.

20. A girth adjustable device as recited in claim 1, 2, 3, 4, or 5, wherein said plurality of shaft members further comprises at least one side extension having at least one groove.

21. A girth adjustable device as recited in claim 20, wherein said plurality of shaft members further comprises at least one side extension groove connector.

22. A girth adjustable device as recited in claim 1, 2, 3, 4, or 5, wherein said controller further comprises at least one handle having a bearing.

23. A girth adjustable device as recited in claim 1, 2, 3, 4, or 5, further comprising at least one shaft member orifice stimulation protrusion.

24. A girth adjustable device as recited in claim 1, 2, 3, 4, or 5, further comprising at least one sheath orifice stimulation protrusion.

25. A girth adjustable device as recited in claim 1, 2, 3, 4, or 5, further comprising at least one prostate stimulation protrusion.

26. A girth adjustable device as recited in claim 1, 2, 3, 4, or 5, further comprising at least one housing external protrusion.

27. A girth adjustable device as recited in claim 1, 2, 3, 4, or 5, further comprising at least one sheath external protrusion.

28. A girth adjustable device as recited in claim 1, 2, 3, 4, or 5, further comprising at least one girth adjustment indicator.

29. A girth adjustable device as recited in claim 1, 2, 3, 4, or 5, further comprising at least one strap.

30. A girth adjustable device as recited in claim 1, 2, 3, 4, or 5, further comprising at least one grip.

31. A girth adjustable device as recited in claim 1, 2, 3, 4, or 5, further comprising at least one magnet.

32. A girth adjustable device as recited in claim 1, 2, 3, 4, or 5, further comprising at least one resilient band.

33. A girth adjustable device as recited in claim 1, 2, 3, 4, or 5, wherein said housing further comprises at least one spring.

34. A girth adjustable device as recited in claim 1, 2, 3, 4, or 5, further comprising at least one shaft spring.

35. A girth adjustable device as recited in claim 1, 2, 3, 4, or 5, further comprising at least one weight.

36. A girth adjustable device as recited in claim 1, 2, 3, 4, or 5, further comprising at least one penis ring.

37. A girth adjustable device as recited in claim 1, 2, 3, 4, or 5, further comprising at least one closure element.

38. A girth adjustable device as recited in claim 1, 2, 3, 4 or 5, further comprising at least one controller angular transmission.

39. A girth adjustable device as recited in claim 1, further comprising at least one threaded shaft angular transmission having a threaded shaft angular transmission housing.

40. A girth adjustable device as recited in claim 1, 2, 3, 4, or 5, wherein said controller further comprises a plurality of gears.

41. A girth adjustable device as recited in claim 40, wherein said controller further comprises a third end, wherein said plurality of gears connects said second end of said controller to said third end of said controller.

42. A girth adjustable device as recited in claim 1, 2, 3, 4, or 5, wherein said first end of said controller further comprises at least one male connection and at least one female connection, wherein said male connection removably fits into said female connection, wherein when said male connection is connected to said female connection and when said first end of said controller rotates, said second end of said controller rotates.

43. A girth adjustable device as recited in claim 42, wherein said controller further comprises at least one locking system.

44. A girth adjustable device as recited in claim 1, 2, 3, 4, or 5, further comprising at least one visual and/or tactile indication.

45. A girth adjustable device as recited in claim 1, 2, 3, 4, or 5, further comprising at least one color code.

46. A girth adjustable device as recited in claim 1, 2, 3, 4, or 5, further comprising at least one serial number.

47. A girth adjustable device as recited in claim 1, 2, 3, 4, or 5, wherein said controller is made of a rigid material.

48. A girth adjustable device as recited in claim 1, 2, 3, 4, or 5, wherein said controller is made of a semi-rigid material.

49. A girth adjustable device as recited in claim 1, 2, 3, 4, or 5, wherein said housing is made of a rigid material.

50. A girth adjustable device as recited in claim 1, 2, 3, 4, or 5, wherein said housing is made of a semirigid material.

51. A girth adjustable device as recited in claim 1, 2, 3, 4, or 5, wherein said threaded shaft is made of metal.

52. A girth adjustable device as recited in claim 1, 2, 3, 4, or 5, wherein said threaded shaft is made of plastic.

53. A girth adjustable device as recited in claim 1, 2, 3, 4, or 5, wherein said shaft member is made of plastic.

54. A girth adjustable device as recited in claim 1, 2, 3, 4, or 5, wherein said shaft member is made of metal.

55. A girth adjustable device as recited in claim 1, 2, 3, 4, or 5, wherein said module is made of plastic.

56. A girth adjustable device as recited in claim 1, 2, 3, 4, or 5, wherein said module is made of metal.

57. A girth adjustable device as recited in claim 1, 2, 3, 4, or 5, wherein said sheath is made of silicone.

58. A girth adjustable device as recited in claim 1, 2, 3, 4, or 5, wherein said sheath is made of rubber.

59. A girth adjustable device as recited in claim 1, 2, 3, 4, or 5, further comprising at least one electronic part having at least one electric component.

60. A girth adjustable device as recited in claim 59, further comprising at least one vibration motor.

61. A girth adjustable device as recited in claim 59, further comprising at least one heating element.

62. A girth adjustable device as recited in claim 59, further comprising at least one heart rate monitor.

63. A girth adjustable device as recited in claim 59, further comprising at least one electrical stimulation electrode.

64. A girth adjustable device as recited in claim 59, wherein said electronic part is secured to said girth adjustable device.

65. A girth adjustable device as recited in claim 59, wherein said electronic part is removably secured to said girth adjustable device.

66. A girth adjustable device as recited in claim 59, wherein said electronic part is operated via at least one electronic controller.

67. A girth adjustable device as recited in claim 59, wherein said electronic part is operated by voice.

68. A girth adjustable device as recited in claim 59, wherein said electronic part is operated via at least one computer program designed to run on a desktop computer.

69. A girth adjustable device as recited in claim 59, wherein said electronic part is operated via at least one computer program designed to run on a mobile device.

70. A girth adjustable device as recited in claim 59, further comprising at least one enclosed electric motor having at least one motor having a motor shaft, and a motor housing, wherein said motor shaft of said motor having a motor shaft of said enclosed electric motor is connected to said first end of said controller, wherein when said motor shaft of said motor having a motor shaft of said enclosed electric motor rotates, said first end of said controller and said second end of said controller rotate.

71. A girth adjustable device as recited in claim 70, wherein said motor housing of said enclosed electric motor is secured to said housing.

72. A girth adjustable device as recited in claim 70, wherein said motor housing of said enclosed electric motor is removably secured to said housing.

73. A girth adjustable device as recited in claim 70, wherein said motor shaft of said motor having a motor shaft is secured to said first end of said controller.

74. A girth adjustable device as recited in claim 70, wherein said motor shaft of said motor having a motor shaft is removably secured to said first end of said controller.

75. A girth adjustable device as recited in claim 70, wherein said enclosed electric motor further comprises at least one planetary gear system.

76. A girth adjustable device as recited in claim 70, wherein said enclosed electric motor further comprises a plurality of gears, wherein said plurality of gears connects said motor shaft of said motor having a motor shaft to said controller.

77. A girth adjustable device as recited in claim 1, 2, 3, 4, or 5, wherein the minimum girth size of said sheath girth is greater than 1.28 inch.

78. A girth adjustable device as recited in claim 1, 2, 3, 4, or 5, wherein the maximum girth size of said sheath girth is greater than 1.88 inch.

79. A girth adjustable device as recited in claim 1, 2, 3, 4, or 5, wherein the minimum girth size of said sheath girth is greater than 1.85 inch.

80. A girth adjustable device as recited in claim 1, 2, 3, 4, or 5, wherein the maximum girth size of said sheath girth is greater than 2.82 inch.

81. A girth adjustable device as recited in claim 1, 2, 3, 4, or 5, wherein the minimum girth size of said sheath girth is greater than 2.79 inch.

82. A girth adjustable device as recited in claim 1, 2, 3, 4, or 5, wherein the maximum girth size of said sheath girth is greater than 4.27 inch.

83. A girth adjustable device as recited in claim 1, 2, 3, 4, or 5, wherein the minimum girth size of said sheath girth is greater than 4.24 inch.

84. A girth adjustable device as recited in claim 1, 2, 3, 4, or 5, wherein the maximum girth size of said sheath girth is greater than 6.44 inch.

85. A girth adjustable device as recited in claim 1, 2, 3, 4, or 5, wherein the minimum girth size of said sheath girth is greater than 6.40 inch.

86. A girth adjustable device as recited in claim 1, 2, 3, 4, or 5, wherein the maximum girth size of said sheath girth is greater than 9.66 inch.

87. A girth adjustable device as recited in claim 1, 2, 3, 4, or 5, wherein the minimum girth size of said sheath girth is greater than 9.62 inch.

88. A girth adjustable device as recited in claim 1, 2, 3, 4, or 5, wherein the maximum girth size of said sheath girth is greater than 14.8 inch.

89. A girth adjustable device as recited in claim 1, 2, 3, 4, or 5, wherein said threaded shaft further comprises less than 161 threads per inch.

90. A girth adjustable device as recited in claim 1, 2, 3, 4, or 5, wherein said threaded shaft further comprises less than 81 threads per inch.

91. A girth adjustable device as recited in claim 1, 2, 3, 4, or 5, wherein said threaded shaft further comprises less than 65 threads per inch.

92. A girth adjustable device as recited in claim 1, 2, 3, 4, or 5, wherein said threaded shaft further comprises less than 41 threads per inch.

93. A girth adjustable device as recited in claim 1, 2, 3, 4, or 5, wherein said module further comprises a module cap.

94. A girth adjustable device as recited in claim 1, 2, 3, 4, or 5, wherein said sheath further comprises at least one longitudinal protrusion.

95. A girth adjustable device as recited in claim 1, 2, 3, 4, or 5, wherein said tip end of at least one said shaft member of said plurality of shaft members is configured with a profiled shape.

96. A girth adjustable device as recited in claim 1, 2, 3, 4, or 5, wherein said controller further comprises at least one handy area.

97. A girth adjustable device as recited in claim 1, 2, 3, 4, or 5, wherein said sheath further comprises at least one liquid channel.

98. A girth adjustable device as recited in claim 1, 2, 3, 4, or 5, further comprising a flexible shaft.

99. A girth adjustable device as recited in claim 42, wherein said male connection and/or said female connection of said controller are made of a ferromagnetic material.

100. A girth adjustable device as recited in claim 42, wherein said controller further comprises a flexible shaft.

101. A girth adjustable device as recited in claim 70, wherein said first end of said controller further comprises at least one male connection and at least one female connection, wherein said male connection removably fits into said female connection, wherein when said male connection is connected to said female connection and when said first end of said controller rotates, said second end of said controller rotates.

102. A girth adjustable device as recited in claim 101, wherein said male connection and/or said female connection of said controller are made of a ferromagnetic material.

103. A girth adjustable device as recited in claim 101, wherein said controller further comprises a flexible shaft.

104. A girth adjustable device as recited in claim 101, wherein said controller further comprises at least one locking system.

105. A girth adjustable device as recited in claim 8, wherein said controller-connector further comprises at least one wing nut fastener.

106. A girth adjustable device as recited in claim 1, 2, 3, 4, or 5, wherein said sheath further comprises an additive.

107. A girth adjustable device as recited in claim 1, 2, 3, 4, or 5, wherein said first end of said controller is configured as a coupling nut.

108. A girth adjustable device as recited in claim 1, 2, 3, 4, or 5, wherein said first end of said controller is configured as a motor shaft coupler.

109. A girth adjustable device as recited in claim 1, 2, 3, 4, or 5, wherein said first end of said controller is configured as a crank.

110. A girth adjustable device as recited in claim 1, 2, 3, 4, or 5, wherein said housing further comprises at least one said shaft member protrusion configured as a fastener.

111. A girth adjustable device as recited in claim 1, 2, or 4, wherein said controller is manufactured with said threaded shaft.

112. A girth adjustable device as recited in claim 4, wherein said plurality of shaft members further comprises at least one module connector groove.

113. A girth adjustable device as recited in claim 112, further comprising at least one module having at least one conical section with a slant height, at least one anti-rotation connector selected from a group consisting of: a linear anti-rotation connector, a capital letter T shape anti-rotation connector, and an inclined capital letter T shape anti-rotation connector, and a canal selected from a group consisting of: a threaded canal, a threaded canal having at least one fastener cavity, and a non-threaded canal having at least one fastener cavity, wherein said canal receives said threaded shaft, wherein said module connector groove of said shaft member slidably receives said anti-rotation connector of said module having at least one conical section with a slant height, at least one anti-rotation connector selected from a group consisting of: a linear anti-rotation connector, a capital letter T shape anti-rotation connector, and an inclined capital letter T shape anti-rotation connector, and a canal selected from a group consisting of: a threaded canal, a threaded canal having at least one fastener cavity, and a non-threaded canal having at least one fastener cavity.

114. A girth adjustable device as recited in claim 5, wherein said plurality of shaft members further comprises at least one module connector groove.

115. A girth adjustable device as recited in claim 114, further comprising at least one module having at least one conical section with a slant height, at least one anti-rotation connector selected from a group consisting of: a linear anti-rotation connector, a capital letter T shape anti-rotation connector, and an inclined capital letter T shape anti-rotation connector, and a canal selected from a group consisting of: a non-threaded canal, a threaded canal, a threaded canal having at least one fastener cavity, and a non-threaded canal having at least one fastener cavity, wherein said canal receives said threaded shaft, wherein said module connector groove of said shaft member slidably receives said anti-rotation connector of said module having at least one conical section with a slant height, at least one anti-rotation connector selected from a group consisting of: a linear anti-rotation connector, a capital letter T shape anti-rotation connector, and an inclined capital letter T shape anti-rotation connector, and a canal selected from a group consisting of: a non-threaded canal, a threaded canal, a threaded canal having at least one fastener cavity, and a non-threaded canal having at least one fastener cavity, wherein said module having at least one conical section with a slant height, at least one anti-rotation connector selected from a group consisting of: a linear anti-rotation connector, a capital letter T shape anti-rotation connector, and an inclined capital letter T shape anti-rotation connector, and a canal selected from a group consisting of: a non-threaded canal, a threaded canal, a threaded canal having at least one fastener cavity, and a non-threaded canal having at least one fastener cavity is secured to said threaded shaft.

116. A girth adjustable device as recited in claim 1, 2, 3, 4, or 5, wherein the girth size of said sheath girth incrementally increases by less than 0.03937 inch when the controller rotates in the direction of increase of said sheath girth.

117. A girth adjustable device as recited in claim 1, 2, 3, 4, or 5, wherein the girth size of said sheath girth incrementally increases by more than 0.03937 inch when the controller rotates in the direction of increase of said sheath girth.

118. A girth adjustable device as recited in claim 1, 2, 3, 4, or 5, wherein the girth size of said sheath girth incrementally decreases by less than 0.03937 inch when the controller rotates in the direction of decrease of said sheath girth.

119. A girth adjustable device as recited in claim 1, 2, 3, 4, or 5, wherein the girth size of said sheath girth incrementally decreases by more than 0.03937 inch when the controller rotates in the direction of decrease of said sheath girth.

120. A girth adjustable device as recited in claim 1, 2, 3, 4, or 5, wherein said controller is made of a magnetized metal.

121. A girth adjustable device as recited in claim 1, 2, 3, 4, or 5, wherein said threaded shaft is made of a magnetized metal.

122. A girth adjustable device as recited in claim 1, 2, 3, 4, or 5, wherein said housing is made of a magnetized metal.

123. A girth adjustable device as recited in claim 1, 2, 3, 4, or 5, wherein said module is made of a magnetized metal.

124. A girth adjustable device as recited in claim 1, 2, 3, 4, or 5, wherein said shaft member is made of a magnetized metal.

125. A girth adjustable device as recited in claim 37, wherein said closure element further comprises at least one connector.

126. A girth adjustable device as recited in claim 39, wherein said threaded shaft angular transmission housing of said threaded shaft angular transmission further comprises at least one angular transmission connector.

127. A girth adjustable device as recited in claim 1, 2, 3, 4, or 5, further comprising at least one body skin protection element.

* * * * *